US011931059B2

(12) United States Patent
Black et al.

(10) Patent No.: US 11,931,059 B2
(45) Date of Patent: Mar. 19, 2024

(54) SURGICAL INSTRUMENT WITH A CARRIER KART AND VARIOUS COMMUNICATION CABLE ARRANGEMENTS

(71) Applicant: Cilag GmbH International, Zug (CH)

(72) Inventors: Brian D. Black, Loveland, OH (US); Andrew T. Beckman, Cincinnati, OH (US); Matthew T. Stone, Mason, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 305 days.

(21) Appl. No.: 17/077,373

(22) Filed: Oct. 22, 2020

(65) Prior Publication Data
US 2022/0125473 A1   Apr. 28, 2022

(51) Int. Cl.
*A61B 17/32* (2006.01)
*A61B 17/295* (2006.01)
(Continued)

(52) U.S. Cl.
CPC .... *A61B 17/320092* (2013.01); *A61B 17/295* (2013.01); *A61B 34/30* (2016.02);
(Continued)

(58) Field of Classification Search
CPC .... A61B 17/320092; A61B 17/320068; A61B 17/295; A61B 90/03; A61B 2017/320074; A61B 2017/320094; A61G 13/101
See application file for complete search history.

(56) References Cited

U.S. PATENT DOCUMENTS 7,354,440 B2   4/2008   Truckai et al.
7,381,209 B2   6/2008   Truckai et al.
(Continued)

FOREIGN PATENT DOCUMENTS

CN   111358561 A   7/2020
WO   WO 2021/259845 A2   12/2021

OTHER PUBLICATIONS

European Communication dated Apr. 14, 2023, for Application No. 21806360.0, 10 pages.
(Continued)

*Primary Examiner* — Sarah A Long
(74) *Attorney, Agent, or Firm* — Frost Brown Todd LLP

(57) ABSTRACT

An ultrasonic surgical instrument including an end effector having an ultrasonic blade, a shaft assembly that defines a longitudinal axis proximally extending from the end effector and an ultrasonic transducer assembly proximally extending from an acoustic waveguide in communication with the ultrasonic blade. The ultrasonic surgical instrument also includes a housing proximally projecting from the shaft assembly such that the ultrasonic transducer assembly is positioned within the housing and a carrier moveably supports the ultrasonic transducer assembly along the longitudinal axis. The carrier collectively moves the ultrasonic transducer assembly, the acoustic waveguide, and the end effector relative to the housing from a proximal, retracted position to a distal, extended position, for inserting the ultrasonic blade into a patient. The ultrasonic surgical instrument also includes an electrical cable extending through the housing at a cable port that transmits electrical communication with the ultrasonic transducer assembly.

17 Claims, 62 Drawing Sheets

(51) Int. Cl.
- *A61B 34/30* (2016.01)
- *A61B 90/00* (2016.01)
- *A61G 13/10* (2006.01)
- *A61B 17/072* (2006.01)
- *A61B 17/29* (2006.01)

(52) U.S. Cl.
CPC ............ *A61B 90/03* (2016.02); *A61G 13/101* (2013.01); *A61B 2017/07285* (2013.01); *A61B 2017/2943* (2013.01); *A61B 2017/320074* (2017.08); *A61B 2017/320094* (2017.08); *A61B 2034/303* (2016.02)

(56) References Cited

U.S. PATENT DOCUMENTS

| | | |
|---|---|---|
| 8,663,220 B2 | 3/2014 | Wiener et al. |
| 9,351,754 B2* | 5/2016 | Vakharia ........ A61B 17/320092 |
| 9,949,785 B2 | 4/2018 | Price et al. |
| 10,349,939 B2 | 7/2019 | Shelton, IV et al. |
| 11,457,945 B2 | 10/2022 | Hunter et al. |
| 11,471,181 B2 | 10/2022 | Hunter et al. |
| 11,612,409 B2 | 3/2023 | Black et al. |
| 11,660,093 B2 | 5/2023 | Bakos et al. |
| 11,690,642 B2 | 7/2023 | Black et al. |
| 11,712,261 B2 | 8/2023 | Hunter et al. |
| 2006/0079874 A1 | 4/2006 | Faller et al. |
| 2007/0191713 A1 | 8/2007 | Eichmann et al. |
| 2007/0239028 A1 | 10/2007 | Houser et al. |
| 2008/0200940 A1 | 8/2008 | Eichmann et al. |
| 2011/0087212 A1 | 4/2011 | Aldridge et al. |
| 2017/0056051 A1* | 3/2017 | Dickerson .............. A61B 90/03 |
| 2017/0072561 A1 | 3/2017 | Schlegel et al. |
| 2017/0172608 A1 | 6/2017 | Madan et al. |
| 2018/0049795 A1 | 2/2018 | Swayze et al. |
| 2018/0333187 A1 | 11/2018 | Sawhney |
| 2019/0029712 A1 | 1/2019 | Stoddard et al. |
| 2019/0125360 A1 | 5/2019 | Shelton, IV et al. |
| 2019/0201136 A1 | 7/2019 | Shelton, IV et al. |
| 2019/0206569 A1 | 7/2019 | Shelton, IV et al. |
| 2019/0314099 A1 | 10/2019 | Grover et al. |
| 2019/0380734 A1* | 12/2019 | Cowley .......... A61B 17/320092 |
| 2020/0100830 A1 | 4/2020 | Henderson et al. |
| 2020/0345406 A1* | 11/2020 | Kato ............ A61B 2018/00607 |
| 2021/0015572 A1 | 1/2021 | Gomez et al. |
| 2021/0022815 A1 | 1/2021 | Abbott |
| 2021/0393340 A1 | 6/2021 | Beckman et al. |
| 2021/0378773 A1* | 12/2021 | Heiliger ................. A61B 41/10 |
| 2021/0401523 A1* | 12/2021 | Suresh et al. .......... A61B 34/71 |
| 2022/0125460 A1 | 4/2022 | Black et al. |
| 2022/0125461 A1 | 4/2022 | Black et al. |
| 2022/0125463 A1 | 4/2022 | Black et al. |
| 2022/0125464 A1 | 4/2022 | Black et al. |
| 2022/0125465 A1 | 4/2022 | Beckman et al. |
| 2022/0125466 A1 | 4/2022 | Beckman et al. |
| 2022/0125467 A1 | 4/2022 | Black et al. |
| 2022/0125468 A1 | 4/2022 | Scheib et al. |
| 2022/0125469 A1 | 4/2022 | Black et al. |
| 2022/0125470 A1 | 4/2022 | Black et al. |
| 2022/0125471 A1 | 4/2022 | Black et al. |
| 2022/0125472 A1 | 4/2022 | Beckman et al. |

OTHER PUBLICATIONS

International Search Report and Written Opinion dated Mar. 23, 2022, for International Application No. PCT/IB2021/059599, 25 pages.

U.S. Appl. No. 62/930,638, entitled "Articulation Joint with Helical Lumen," filed Nov. 5, 2019.

U.S. Appl. No. 63/018,555, entitled "Latchless Obturator with Interference Fit Feature," filed May 1, 2020.

U.S. Appl. No. 63/018,664, entitled "Stabilizer for Surgical Shafts or Cannulas," filed May 1, 2020.

* cited by examiner

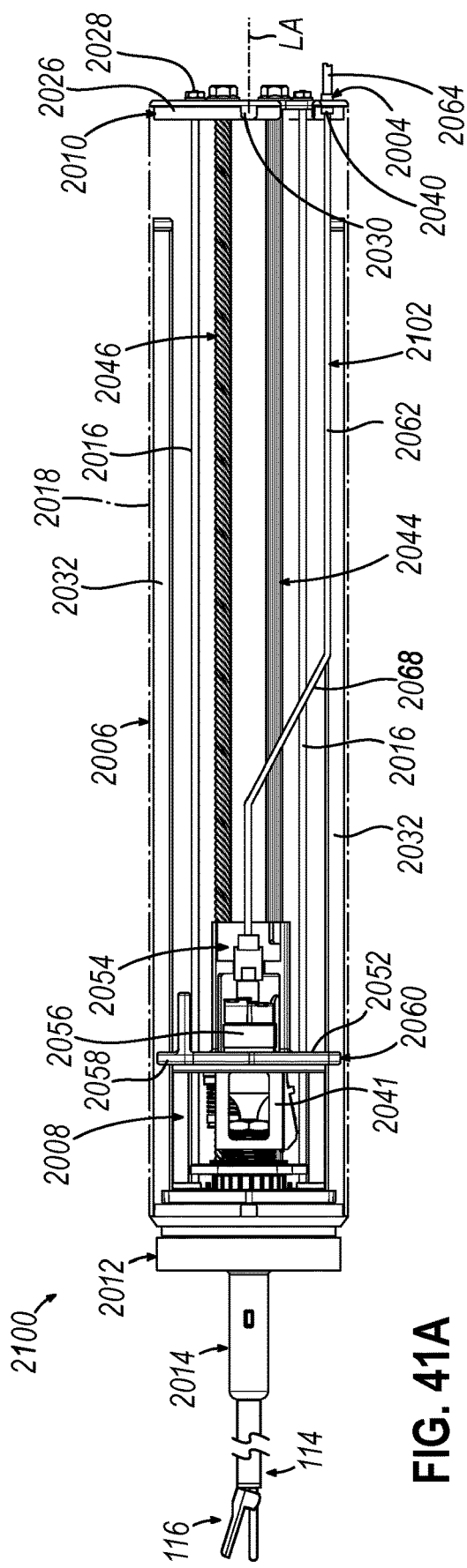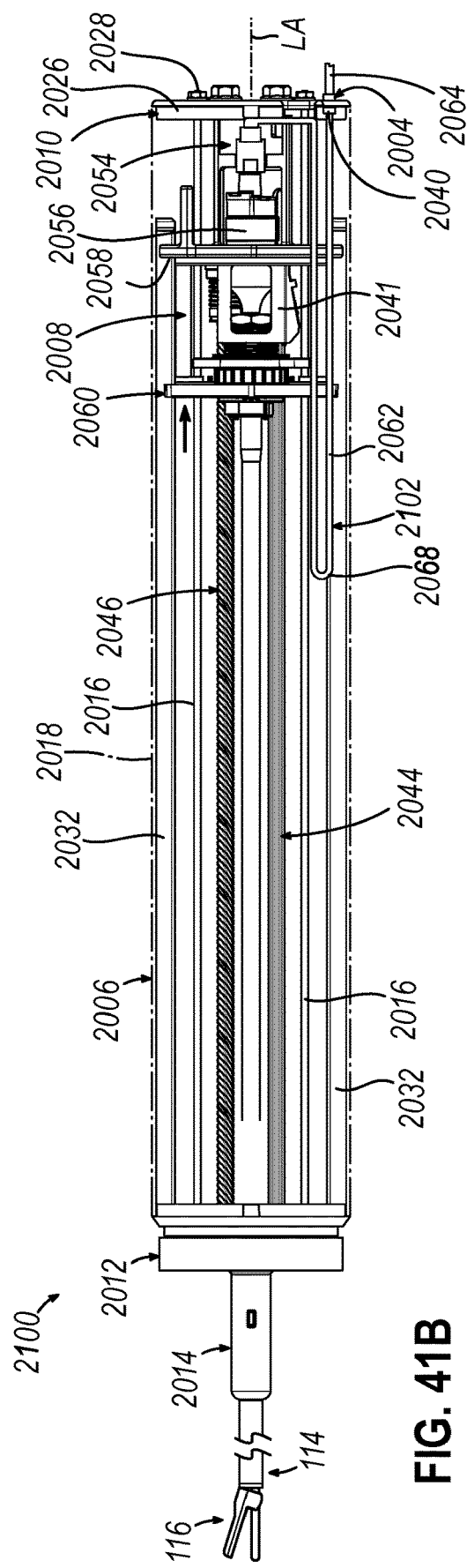
FIG. 41A
FIG. 41B

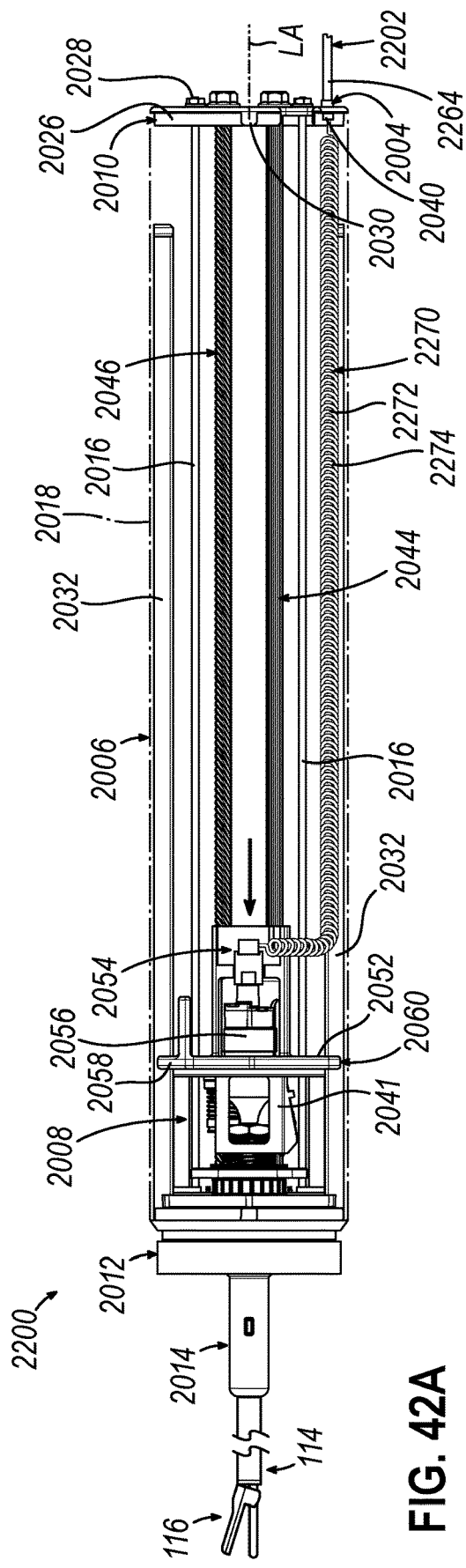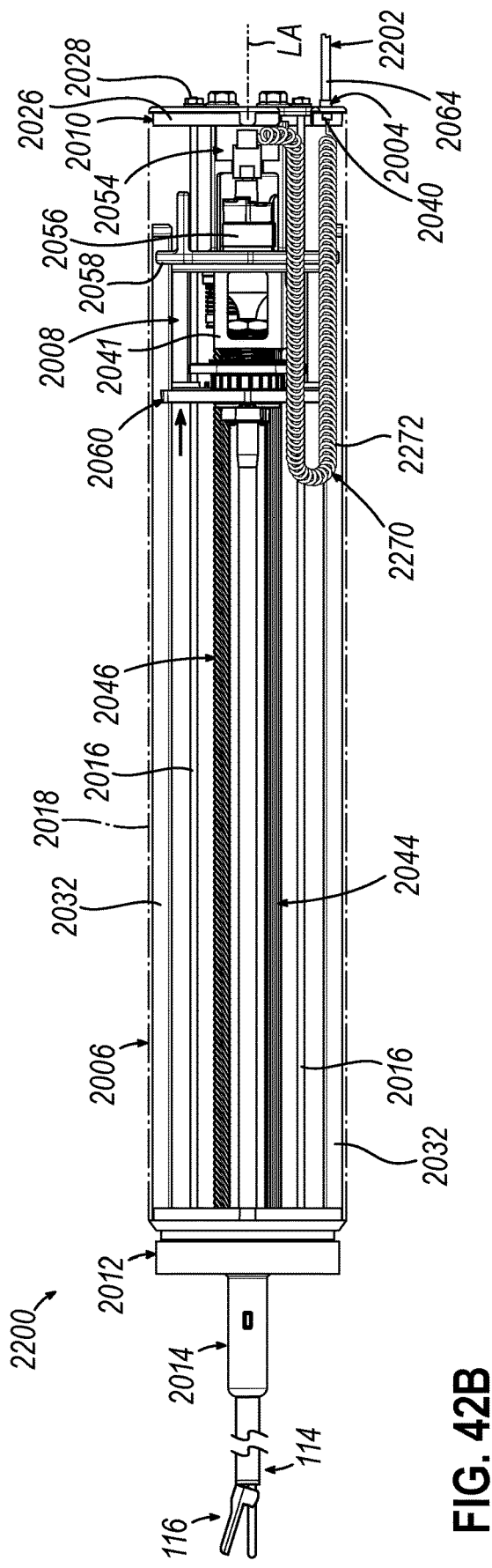
FIG. 42A
FIG. 42B

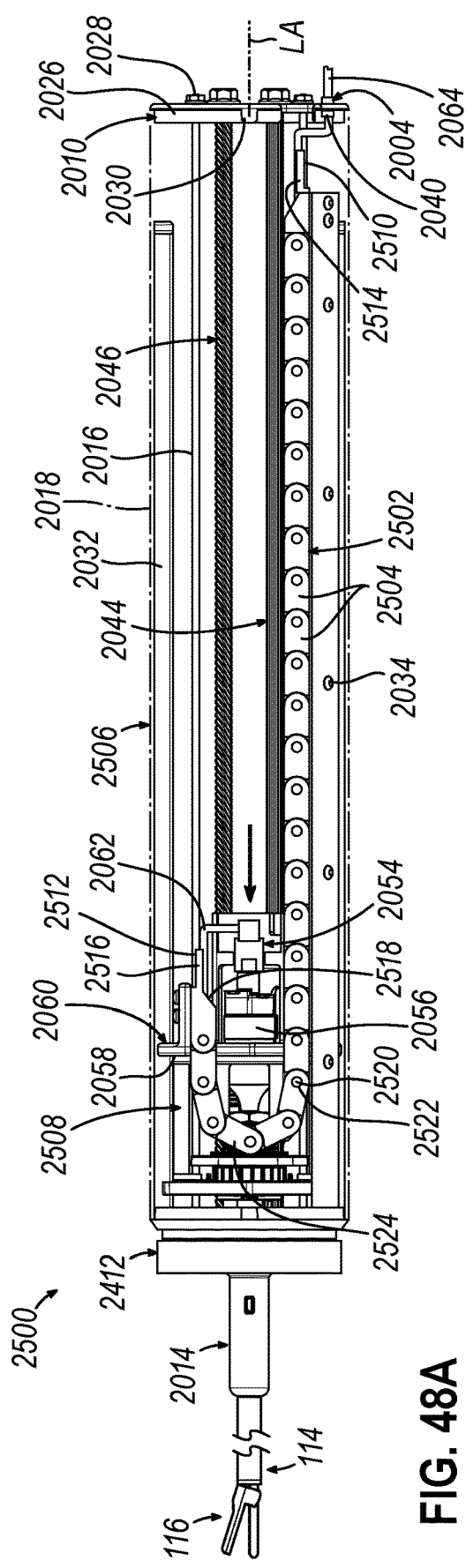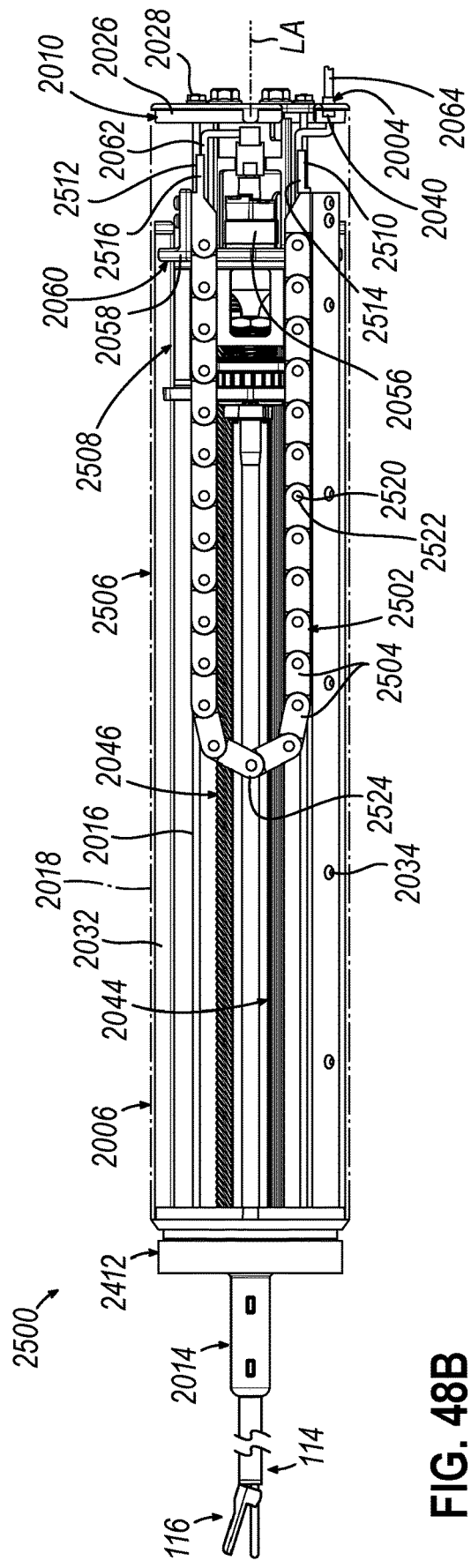
FIG. 48A
FIG. 48B

SURGICAL INSTRUMENT WITH A CARRIER KART AND VARIOUS COMMUNICATION CABLE ARRANGEMENTS

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

In one example, the end effector of the surgical instrument includes a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; and U.S. Pub. No. 2008/0200940, entitled "Ultrasonic Device for Cutting and Coagulating," published Aug. 21, 2008, now abandoned, the disclosure of which is incorporated by reference herein.

Examples of robotic systems, at least some of which have ultrasonic features and/or associated articulatable portions, include U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, issued as U.S. Pat. No. 11,612,409 on Mar. 28, 2023; U.S. patent application Ser. No. 16/556,625, entitled "Ultrasonic Surgical Instrument with Axisymmetric Clamping," filed on Aug. 30, 2019, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, issued as U.S. Pat. No. 11,457,945 on Oct. 4, 2022; U.S. patent application Ser. No. 16/556,727, entitled "Rotatable Linear Actuation Mechanism," filed on Aug. 30, 2019, issued as U.S. Pat. No. 11,712,261 on Aug. 1, 2023; and/or U.S. Pat. App. Ser. No. 62/930,638, entitled "Articulation Joint with Helical Lumen," filed on Nov. 5, 2019. The disclosure of each of these applications is incorporated by reference herein.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 41A depicts a side view of another exemplary surgical instrument with a tubular sidewall of a housing removed for added clarity having a carriage of a carrier KART distally positioned and a flex circuit ribbon extending distally between the carrier KART and an electrical cable attached to a proximal portion of the housing;

FIG. 41B depicts the side view of the surgical instrument similar to FIG. 41A, but with the carriage of the carrier KART proximally positioned and the flex circuit ribbon in a folded state;

FIG. 42A depicts a side view of another exemplary surgical instrument with a tubular sidewall of a housing removed for added clarity having a carriage of a carrier KART distally positioned and a helical cord in an expanded state attached between the carriage of the carrier KART and an electrical cable at a proximal portion of the housing;

FIG. 42B depicts the side view of the surgical instrument similar to FIG. 42A, but with the carriage of the carrier KART proximally positioned and the helical cord in a compressed state;

FIG. 48A depicts a side view of another exemplary surgical instrument with a tubular sidewall of a housing removed for added clarity having a carriage of a carrier KART distally positioned and a cable guide in an extended position attached between the carriage of the carrier KART and a proximal portion of the housing;

FIG. 48B depicts the side view of the surgical instrument similar to FIG. 48A, but with the carriage of the carrier KART in a proximal position and with the cable guide in a folded position;

Figure 1:
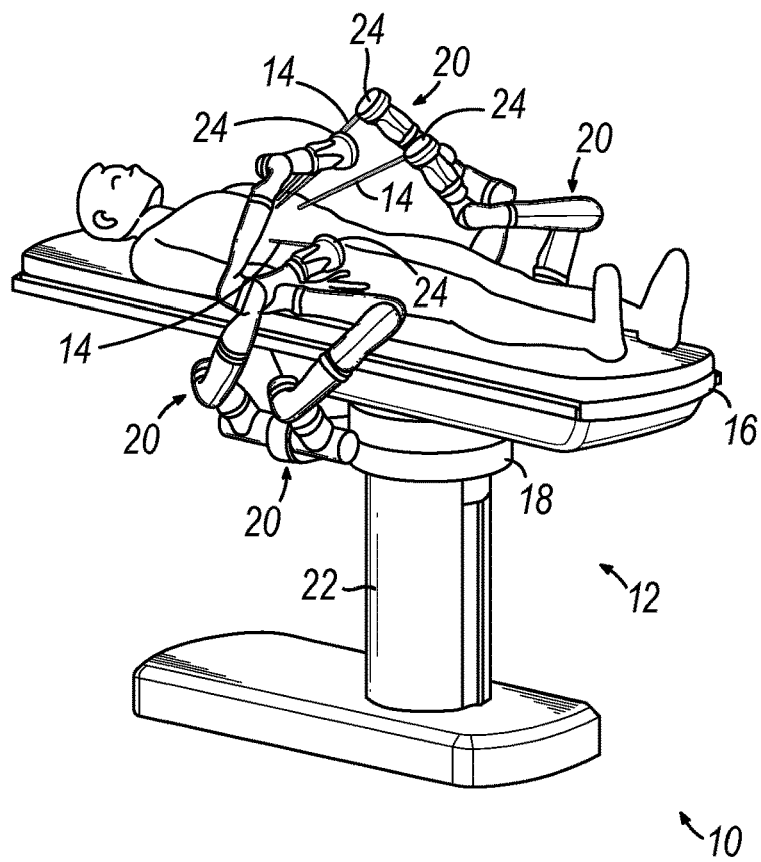
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," "transverse," "underside," "inner," "outer," "upper," "interior," and "exterior" also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. EXEMPLARY ROBOTICALLY-ENABLED MEDICAL SYSTEM

FIG. 1 shows an exemplary robotically-enabled medical system, including a first example of a table-based robotic system (10). Table-based robotic system (10) of the present example includes a table system (12) operatively connected to an instrument for a diagnostic and/or therapeutic procedure in the course of treating a patient. Such procedures may include, but are not limited, to bronchoscopy, ureteroscopy, a vascular procedure, and a laparoscopic procedure. To this end, the instrument illustrated in the present example is an ultrasonic surgical instrument (14) configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein. As described therein and as will be described in greater detail below, ultrasonic surgical instrument (14) is operable to cut tissue and seal or weld tissue (e.g., a blood vessel, etc.) substantially simultaneously. While one or more examples incorporates various ultrasonic features, such as ultrasonic surgical instrument (14), the invention is not intended to be unnecessarily limited to the ultrasonic features described herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate ultrasonic surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as ultrasonic surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
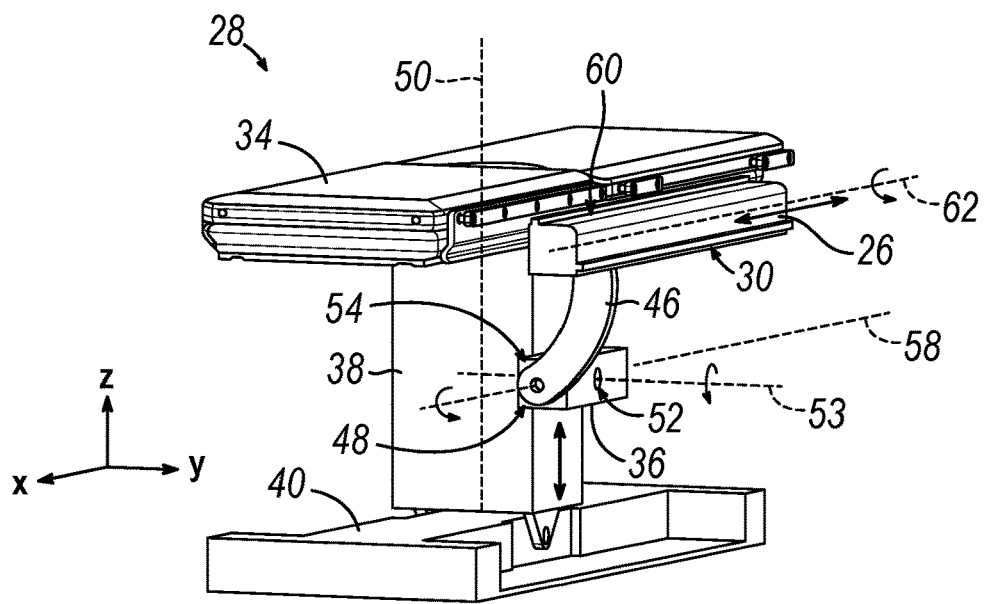
FIG. 2 depicts a perspective view of a second example of a table-based robotic system.
Figure 3:
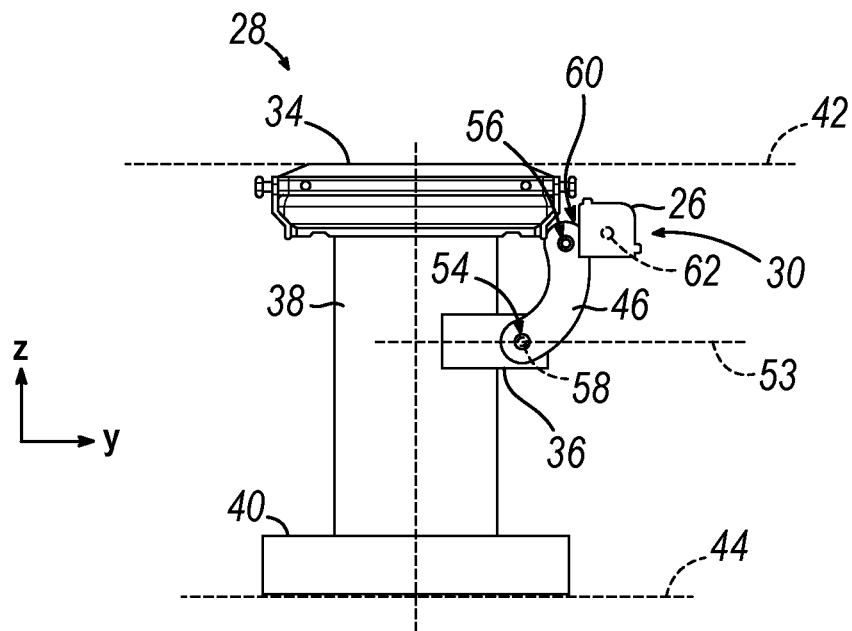
FIG. 3 depicts an end elevational view of the table-based robotic system of FIG. 2.
Figure 4:
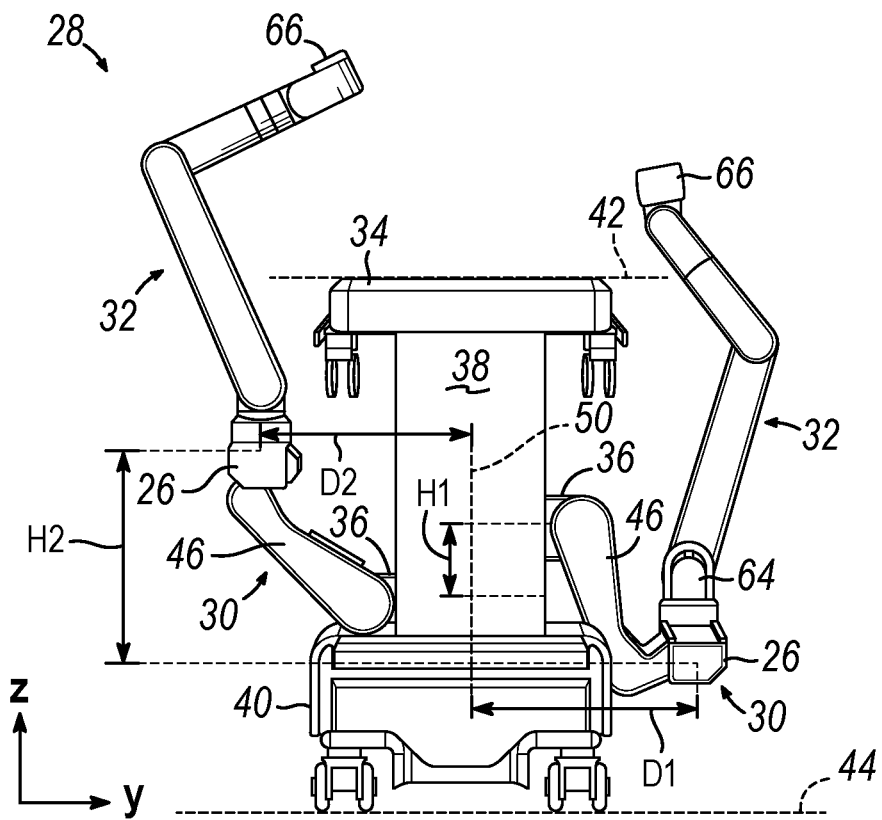
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as ultrasonic surgical instrument (14) (see FIG. 6A), the instrument includes an instrument-based insertion architecture.

Figure 5:
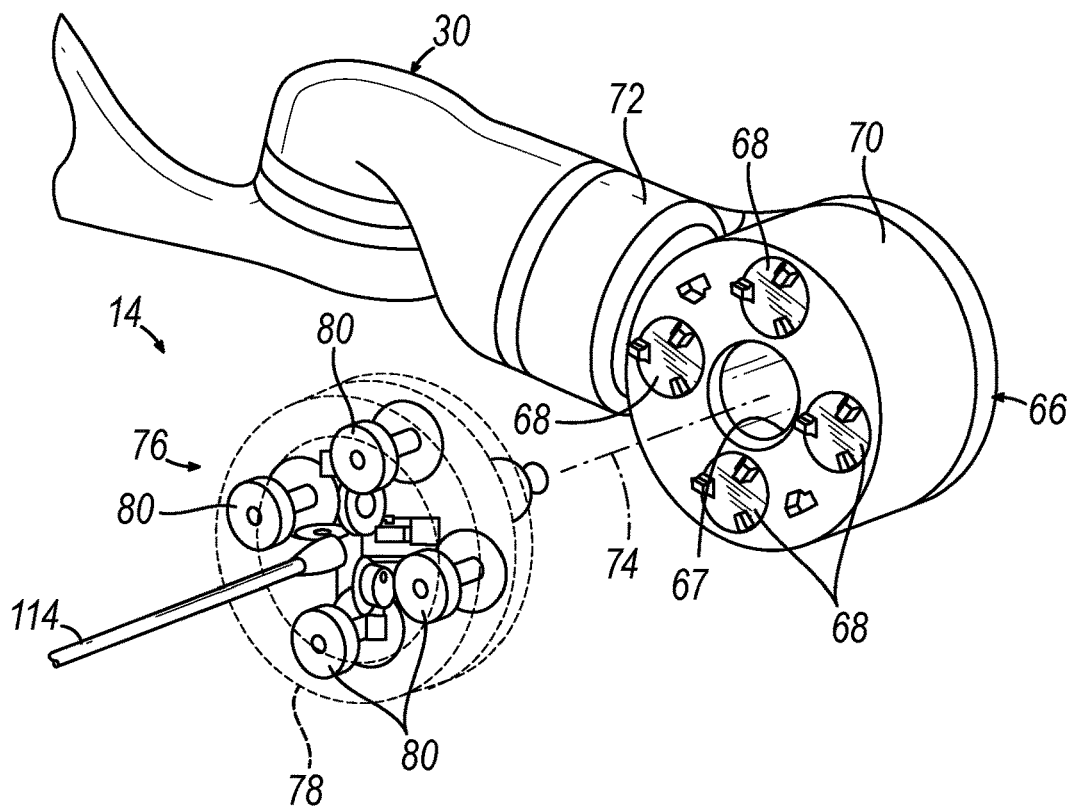
FIG. 5 depicts a partially exploded perspective view of the robotic arm of FIG. 4 having an instrument driver and a first exemplary surgical instrument.

FIG. 5 shows one example of instrument driver (66) in greater detail with ultrasonic surgical instrument (14) removed therefrom. Given the present instrument-based insertion architecture shown with reference to ultrasonic surgical instrument (14), instrument driver (66) further includes a clearance bore (67) extending entirely therethrough so as to movably receive a portion of ultrasonic surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of ultrasonic surgical instrument (14). Instrument driver (66) and ultrasonic surgical instrument (14) of the present example are aligned such that the axes of each drive output (68) are parallel to the axis ultrasonic surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with ultrasonic surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. First Exemplary Ultrasonic Surgical Instrument

Figure 6A:
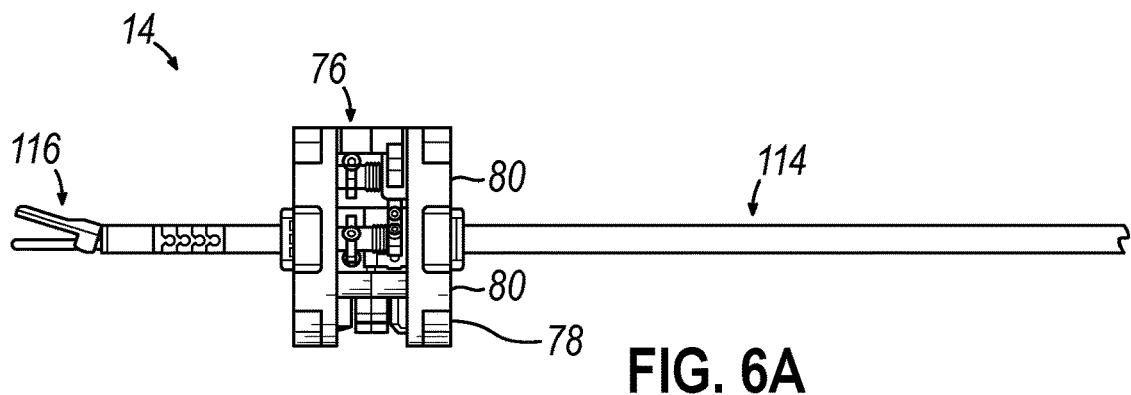
FIG. 6A depicts a side elevational view of the surgical instrument of FIG. 5 in a retracted position.
Figure 6B:
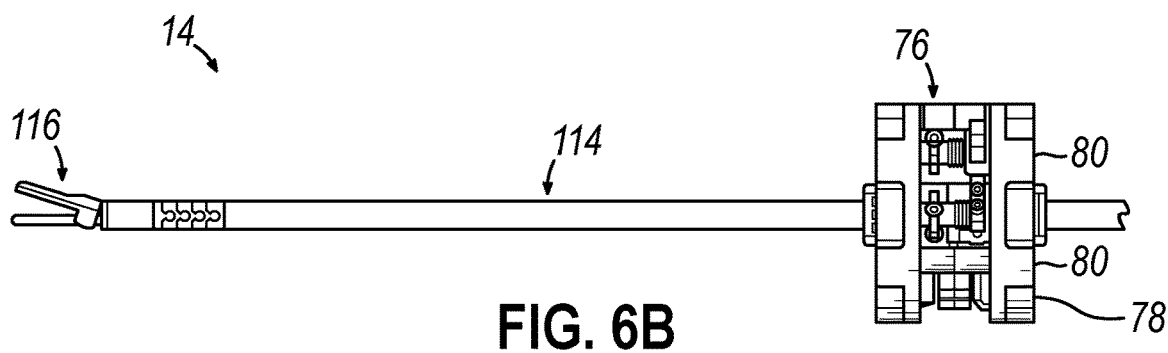
FIG. 6B depicts the side elevational view the surgical instrument similar to FIG. 6A, but in an extended position.

With respect to FIGS. 5-6B and in cooperation with instrument driver (66) discussed above, ultrasonic surgical instrument (14) includes an elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of instrument base (76) with an axis substantially parallel to the axes of the drive inputs (80) as discussed briefly above. With shaft assembly (114) positioned at the center of instrument base (76), shaft assembly (114) is coaxial with instrument driver axis (74) when attached and movably received in clearance bore (67). Thus, rotation of rotational assembly (70) causes shaft assembly (114) of ultrasonic surgical instrument (14) to rotate about its own longitudinal axis while clearance bore (67) provides space for translation of shaft assembly (114) during use.

To this end, FIGS. 5-6B show ultrasonic surgical instrument (14) having the instrument-based insertion architecture as discussed briefly above. Ultrasonic surgical instrument (14) includes elongated shaft assembly (114), the end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly (70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, ultrasonic surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

i. First Exemplary End Effector and Acoustic Drivetrain

Figure 7A:
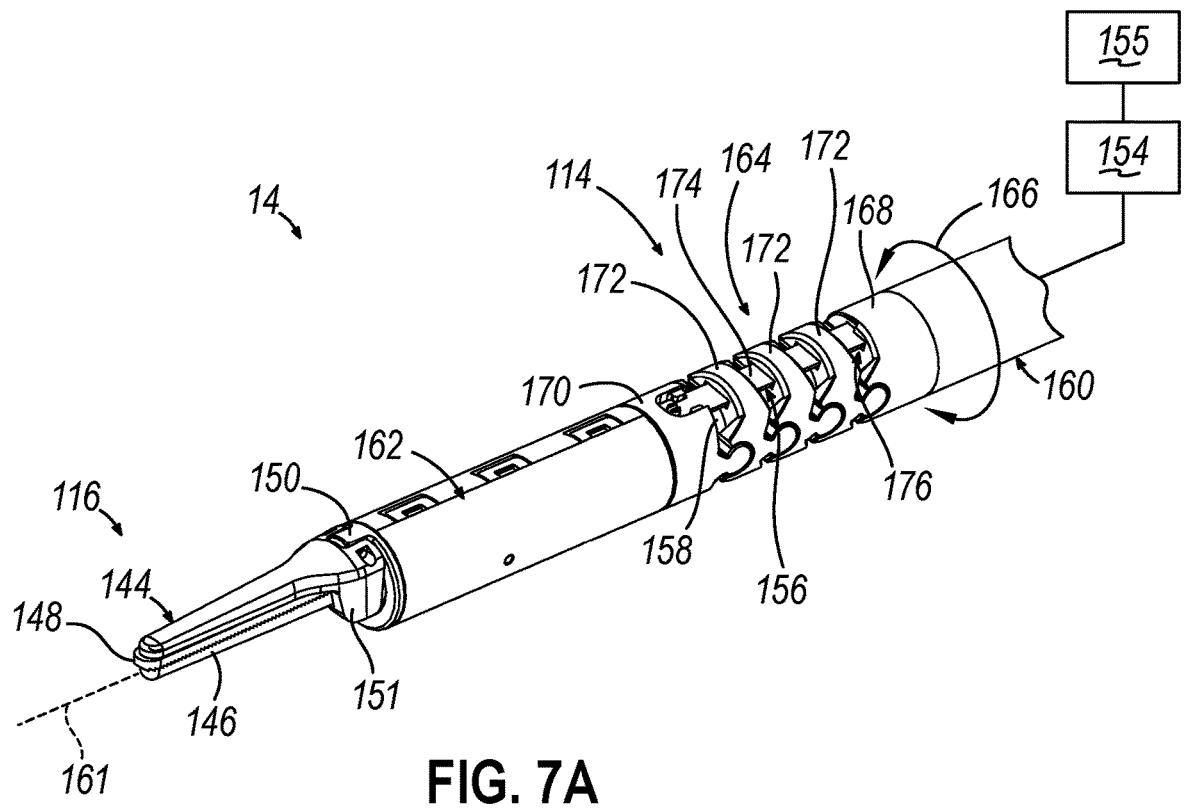
FIG. 7A depicts an enlarged perspective view of the surgical instrument of FIG. 6A with an end effector in a closed position and a shaft assembly in a straight configuration.
Figure 7B:
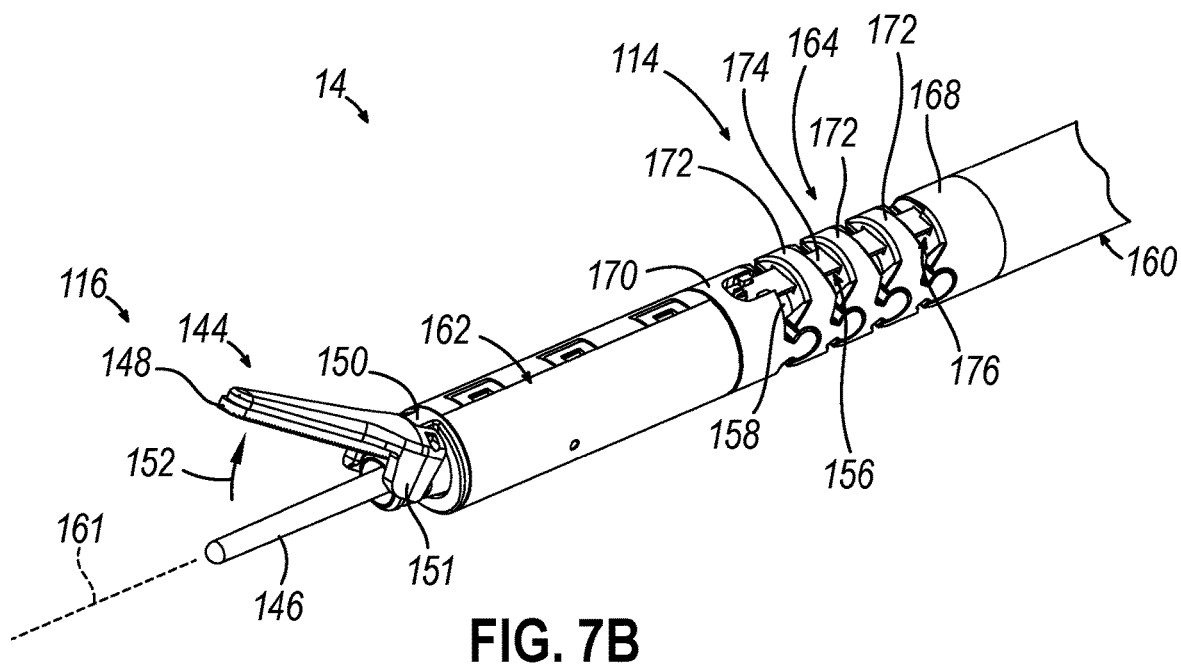
FIG. 7B depicts the enlarged perspective view of the surgical instrument similar to FIG. 7A, but showing the end effector in an open position.

As best seen in FIGS. 7A-7B, end effector (116) of the present example includes a clamp arm (144) and an ultrasonic blade (146). Clamp arm (144) has a clamp pad (148) secured to an underside of clamp arm (144), facing blade (146). Clamp arm (144) is pivotally secured to a distally projecting tongue (150) of shaft assembly (114). Clamp arm (144) is operable to selectively pivot toward and away from blade (146) to selectively clamp tissue between clamp arm (144) and blade (146). A pair of arms (151) extend transversely from clamp arm (144) and are pivotally secured to another portion of shaft assembly (114) configured to longitudinally slide to pivot clamp arm (144) as indicated by an arrow (152) between a closed position shown in FIG. 7A and an open position shown in FIG. 7B.

Blade (146) of the present example is operable to vibrate at ultrasonic frequencies in order to effectively cut through and seal tissue, particularly when the tissue is being compressed between clamp pad (148) and blade (146). Blade (146) is positioned at a distal end of an acoustic drivetrain. This acoustic drivetrain includes a transducer assembly (154) and an acoustic waveguide (156), which includes a flexible portion (158) discussed below in greater detail.

Transducer assembly (154) is further connected to a generator (155) of the acoustic drivetrain. More particularly, transducer assembly (154) is coupled with generator (155) such that transducer assembly (154) receives electrical power from generator (155). Piezoelectric elements (not shown) in transducer assembly (154) convert that electrical power into ultrasonic vibrations. By way of example only, generator (155) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

When transducer assembly (154) of the present example is activated, mechanical oscillations are transmitted through waveguide (156) to reach blade (146), thereby providing oscillation of blade (146) at a resonant ultrasonic frequency (e.g., 55.5 kHz). Thus, when tissue is secured between blade (146) and clamp pad (148), the ultrasonic oscillation of blade (146) may simultaneously sever the tissue and denature the proteins in adjacent tissue cells, thereby providing a coagulative effect with relatively little thermal spread.

ii. First Exemplary Shaft Assembly and Articulation Section

As shown in FIGS. 7A-7B, shaft assembly (114) includes a proximal shaft portion (160) extending along a longitudinal axis (161), a distal shaft portion (162) distally projecting relative to proximal shaft portion (160), and an articulation section (164) extending between proximal and distal shaft portions (160, 162). Shaft assembly (114) is configured to rotate about longitudinal axis (161) as indicated by an arrow (166). In one example, shaft assembly (114) rotates in the clockwise or counterclockwise directions completely around longitudinal axis (161) and may be selectively fixed in any rotational position about longitudinal axis (161) for positioning articulation section (164) and/or end effector (116) about longitudinal axis (161).

Articulation section (164) is configured to selectively position end effector (116) at various lateral deflection angles relative to longitudinal axis (161) defined by proximal shaft portion (160). Articulation section (164) may take a variety of forms. In the present example, articulation section (164) includes a proximal link (168), a distal link (170), and a plurality of intermediate links (172) connected in series between proximal and distal links (168, 170). Articulation section (164) further includes a pair of articulation bands (174) extending along a pair of respective channels (176) collectively defined through links (168, 170, 172). Links (168, 170, 172) are generally configured to pivot relative to each other upon actuation of articulation bands (174) to thereby bend articulation section (164) with flexible portion (158) of waveguide (156) therein to achieve an articulated state.

Figure 8A:
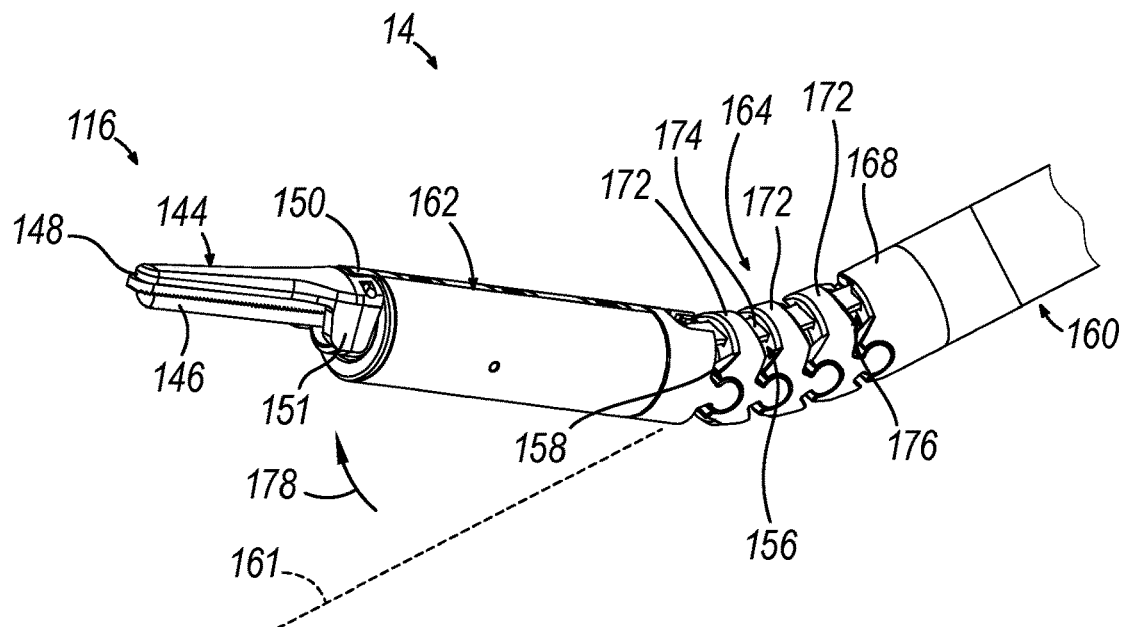
FIG. 8A depicts an enlarged perspective view of the surgical instrument of FIG. 6A with the end effector in a closed position and the shaft assembly in a first articulated configuration.
Figure 8B:
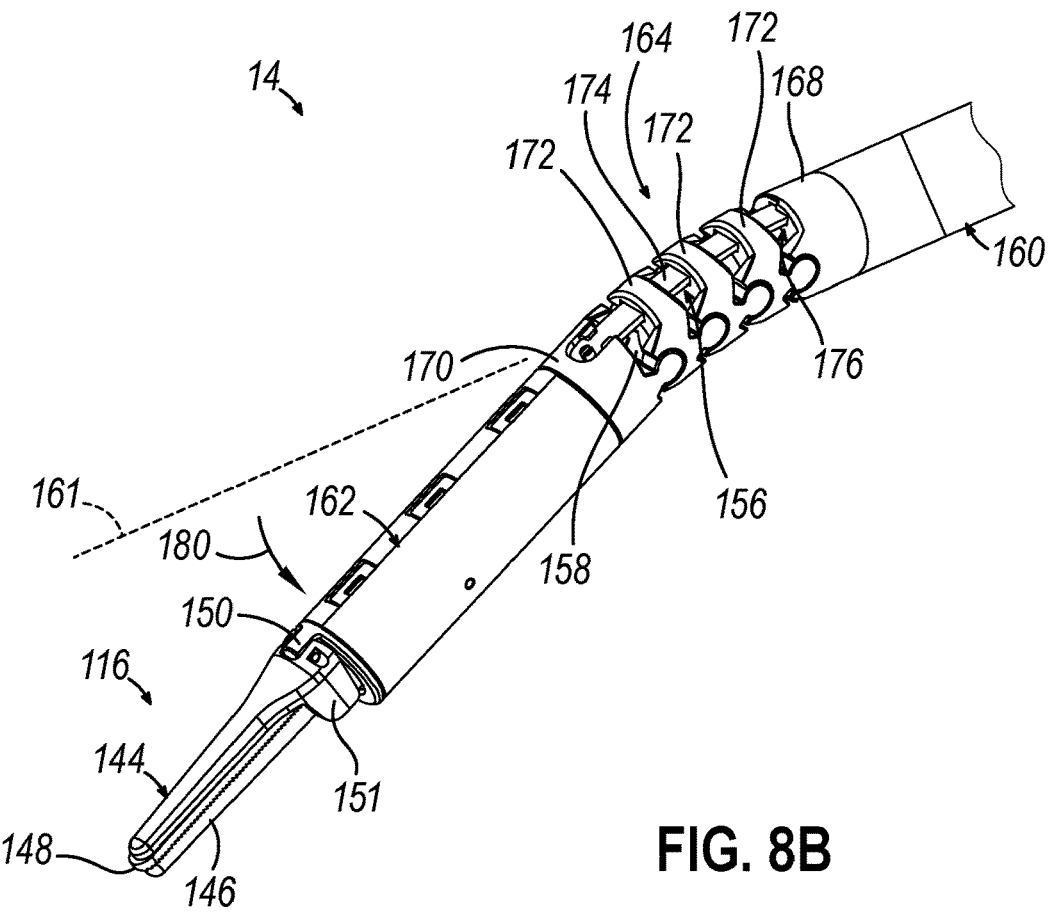
FIG. 8B depicts the enlarged perspective view of the surgical instrument similar to FIG. 8A, but with the shaft assembly in a second articulated configuration.

Links (168, 170, 172) shown in FIGS. 7B-8B pivotally interlock to secure distal shaft portion (162) relative to proximal shaft portion (160) while allowing for deflection of distal shaft portion (162) relative to longitudinal axis (161). Thus, as a pair of articulation bands (174) translate longitudinally in an opposing fashion, this will cause articulation section (164) to bend via links (168, 170, 172) thereby laterally deflecting end effector (116) away from the longitudinal axis (161) of proximal shaft portion (160) from a straight configuration as shown in FIG. 7B to a first articulated configuration as shown in FIG. 8A and indicated by an arrow (178) or a second articulated configuration as shown in FIG. 8B and indicated by an arrow (180). Furthermore, flexible acoustic waveguide (156) is configured to effectively communicate ultrasonic vibrations from waveguide (156) to blade (146) even when articulation section (164) is in an articulated configuration as shown in FIGS. 8A-8B.

II. SECOND EXEMPLARY SURGICAL INSTRUMENT

A. Overview

In some instances, it may be desirable to use various alternative surgical instruments with robotic systems (10, 28) described above in addition to, or in lieu of, surgical instrument (14) described above. Such alternative surgical instruments may be desirable to provide improved operability when used with robotic systems (10, 28). For instance, as described above, surgical instrument (14) may move between a retracted position and extended position. Additionally, it may be beneficial to translate a portion of surgical instrument (14) along a support structure to provide increased surgical access without increasing the dimensions of surgical instrument (14). As also described above, use of rotational assembly (70) of robotic arm (20, 32) may enable rotation of the entire surgical instrument (14), rather than specific structures of surgical instrument (14) being rotatable.

Figure 23:
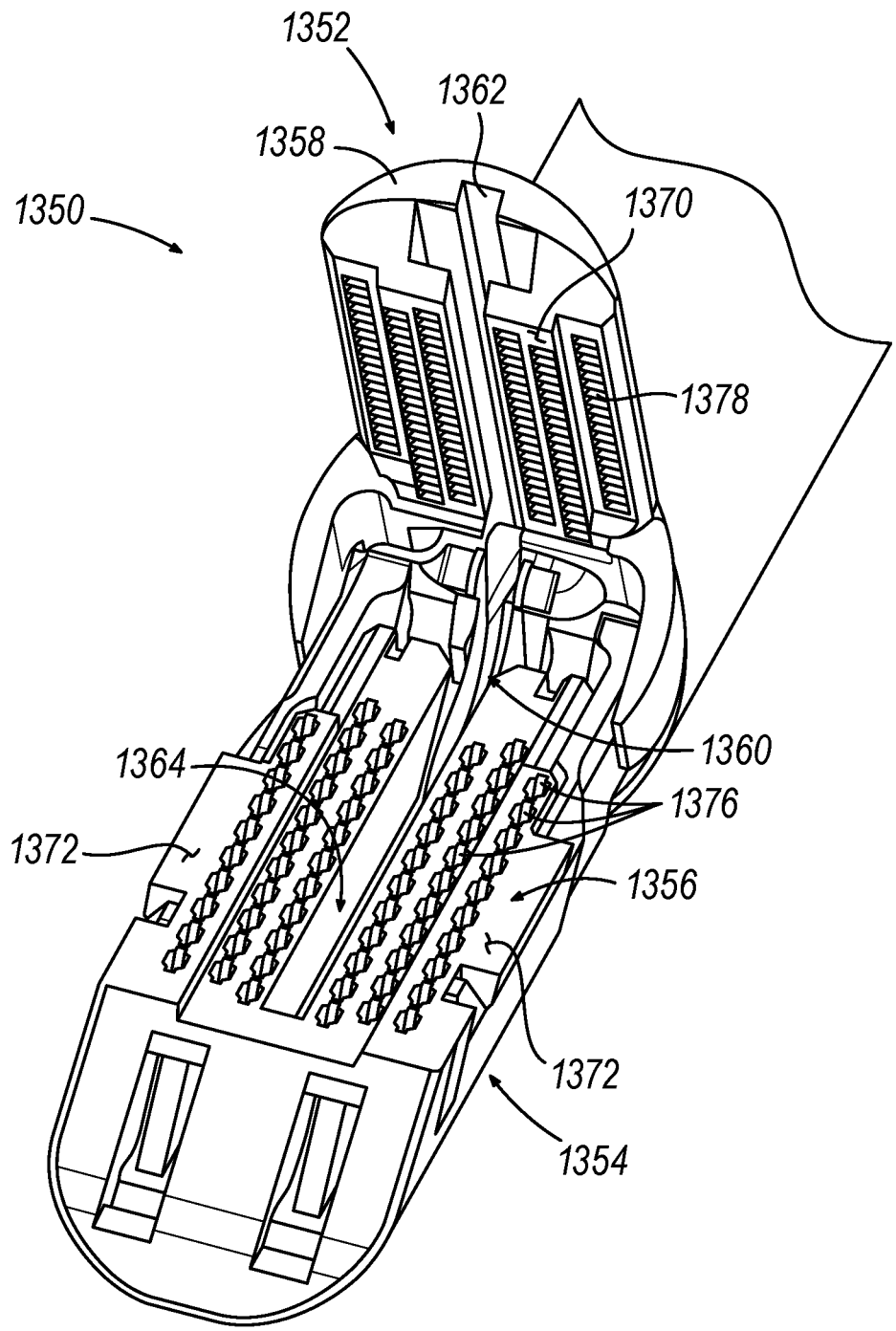
FIG. 23 depicts a third exemplary end effector and a shaft assembly configured for use with the surgical instrument of FIG. 9 with first and second jaws in an open state.
Figure 24:
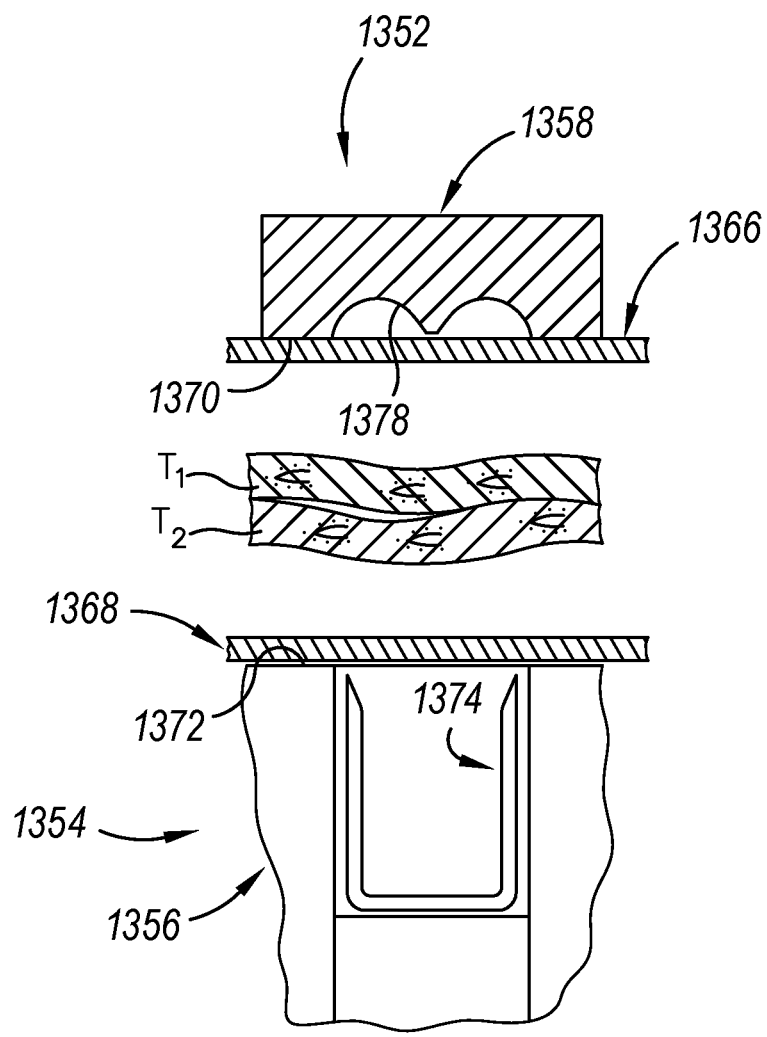
FIG. 24 depicts a sectional end view of a portion of the end effector of FIG. 23 with first and second jaws in the open state and an exemplary pair of buttress assemblies applied to the first and second jaws of the end effector of FIG. 23.

FIGS. 9-20 show a second exemplary alternative surgical instrument (1010) that is configured to be used with robotic systems (10, 28) described above. Surgical instrument (1010) of the present example is shown as an ultrasonic surgical instrument that uses ultrasonic energy to treat tissue. Alternatively, it is envisioned that surgical instrument (1010) may be modified to treat tissue in other manners. For example, it is envisioned that surgical instrument (1010) may be modified to cut and staple tissue using end effector (1350) as shown in FIGS. 23-24, or include one or more radiofrequency electrodes to apply radiofrequency energy to treat tissue. Some surgical instruments are operable to seal tissue by applying radiofrequency (RF) electrosurgical energy to the tissue. Examples of such surgical instruments and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Figure 9:
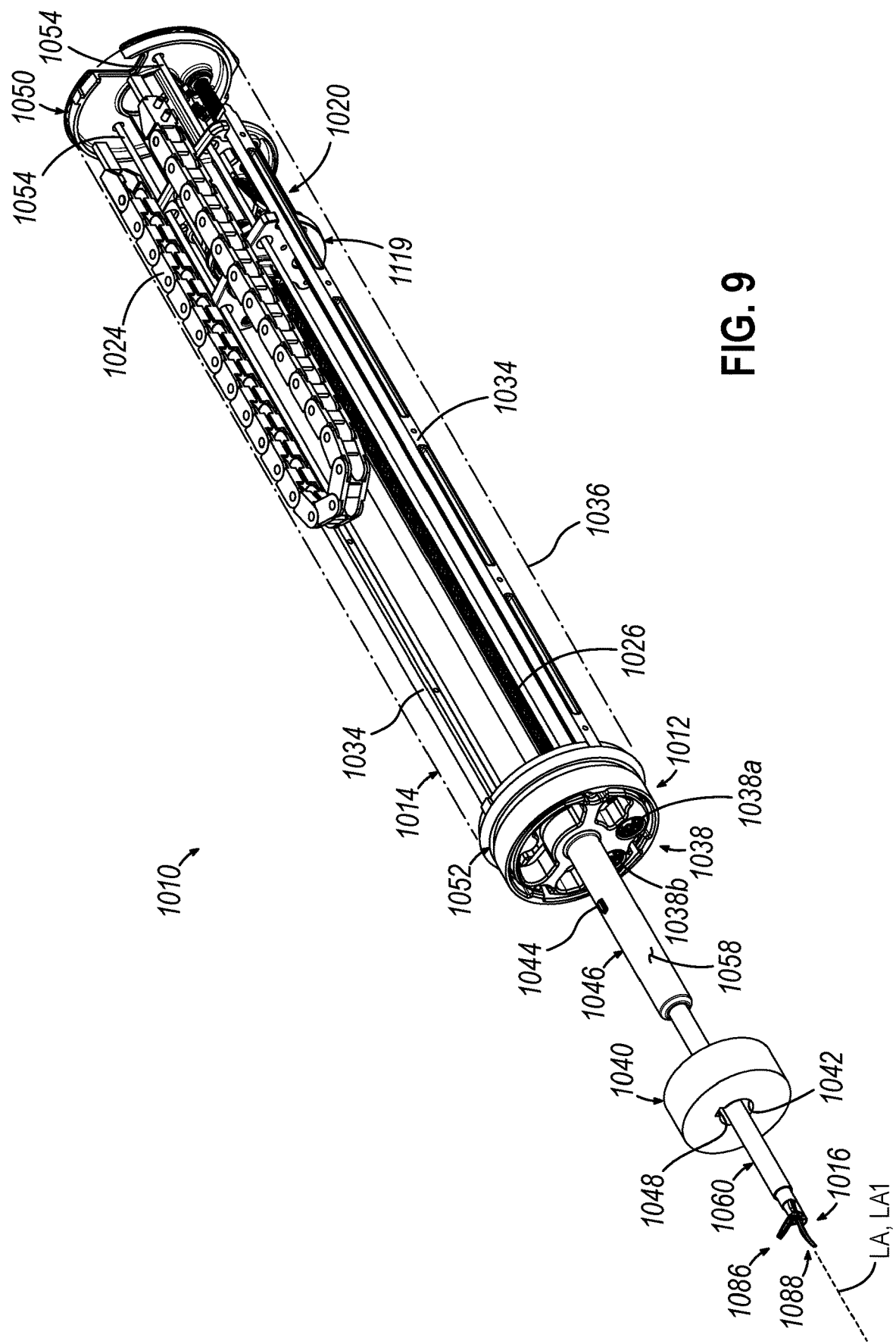
FIG. 9 depicts a perspective view of a second exemplary surgical instrument and a sterile adapter shown schematically prior to being coupled with the surgical instrument, where a housing of the surgical instrument is shown in broken lines to expose a carrier, a shaft assembly, and a second exemplary end effector.
Figure 10:
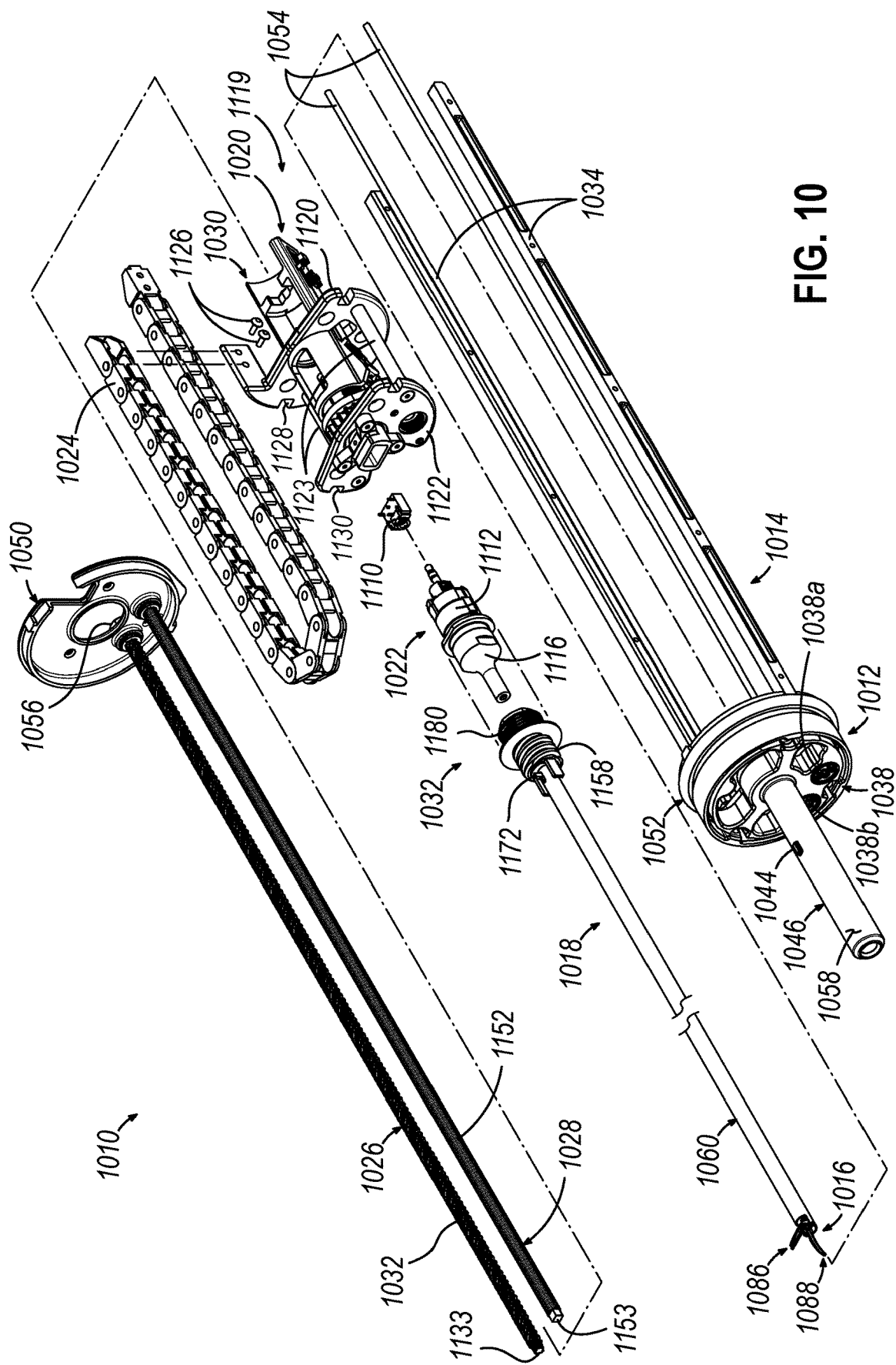
FIG. 10 depicts an exploded perspective view of the surgical instrument of FIG. 9 with the housing removed.

FIG. 9 shows a perspective view of surgical instrument (1010) and a schematic sterile adapter (1040) prior to being coupled with surgical instrument (1010), with a housing (shown as cylindrical housing (1036)) of surgical instrument (1010) being shown in broken lines to expose internal components of surgical instrument (1010). FIG. 10 shows an exploded perspective view of surgical instrument (1010) of FIG. 9 with cylindrical housing (1036) removed. As shown, surgical instrument (1010) includes an attachment interface (1012), a support structure (1014), an end effector (1016), a shaft assembly (1018), a carrier (1020), an ultrasonic transducer assembly (1022), and a flexible cable guide (1024). As shown in FIGS. 9-11B and described in in greater detail with reference to FIGS. 15-20 and 27-29D, carrier (1020) includes a translation driver (1026), an actuation driver (1028), a carriage (1030), an actuation assembly (1032), and one or more guide rails (1034). In the present example, the combination of translation driver (1026), actuation driver (1028), carriage (1030), actuation assembly (1032), and guide rails (1034) may collectively, and more particularly, be referred to as a kinetic articulating rotating tool (KART) or a carrier KART, although it will be appreciated that any features configured to movably support one or more portions of the acoustic drivetrain may generally be referred as "carrier" such that the term "carrier" is not intended to unnecessarily limit the invention to specific aspects of the KART herein.

B. Exemplary Attachment Interface

Similar to surgical instrument (14), surgical instrument (1010) includes attachment interface (1012) similar to attachment interface (78) described above. Attachment interface (1012) is configured to operatively couple with robotic arm (32) of robotic system (10, 28). Attachment interface (1012) includes a plurality of drive inputs (1038) (which include first and second rotational drive inputs (1038a-b)) that face distally and are configured to operatively engage proximally facing drive outputs (68). As shown in FIG. 9, sterile adapter (1040) may be disposed between robotic arm (32) and attachment interface (1012). For example, sterile adapter (1040) may be disposed between drive outputs (68) of robotic arm (32) and drive inputs (1038). Sterile adapter (1040) may allow for certain components of surgical instrument (1010) to remain sterile, and possibly be reused in later surgical procedures to reduce medical waste. Sterile adapter (1040) includes an inner channel (1042) configured to receive at least a portion of shaft assembly (1018). An aligning feature (1044) of a guide shaft (1046) may couple with an aligning feature (1048) of sterile adapter (1040) to secure guide shaft (1046) with sterile adapter (1040). In some versions, surgical instrument (1010) may self-align with sterile adapter (1040).

First and second rotational drive inputs (1038*a-b*) are generally configured to move, actuate, and/or drive various components of surgical instrument (1010). While first and second rotational drive inputs (1038*a-b*) are shown and described, it is envisioned that surgical instrument (1010) may include more or fewer drive inputs as desired. Additionally, the number of drive outputs (68) may not equal the number of drive inputs (1038). For example, the number of drive outputs (68) may be greater than the number of drive inputs (1038). As will be described in greater detail below, first and second rotational drive inputs (1038*a-b*) respectively operatively couple with corresponding drive outputs (68). Additionally, first rotational drive input (1038*a*) may be operatively coupled with translation driver (1026). As a result, first rotational drive input (1038*a*) is configured to actuate translation driver (1026) to translate carriage (1030) and ultrasonic transducer assembly (1022) along a longitudinal axis (LA). Second rotational drive input (1038*b*) may be operatively coupled with actuation driver (1028). Similarly, second rotational drive input (1038*b*) is configured to actuate translation driver (1026) to actuate end effector (1016) (e.g., between open and closed positions).

C. Exemplary Support Structure

Figure 18:
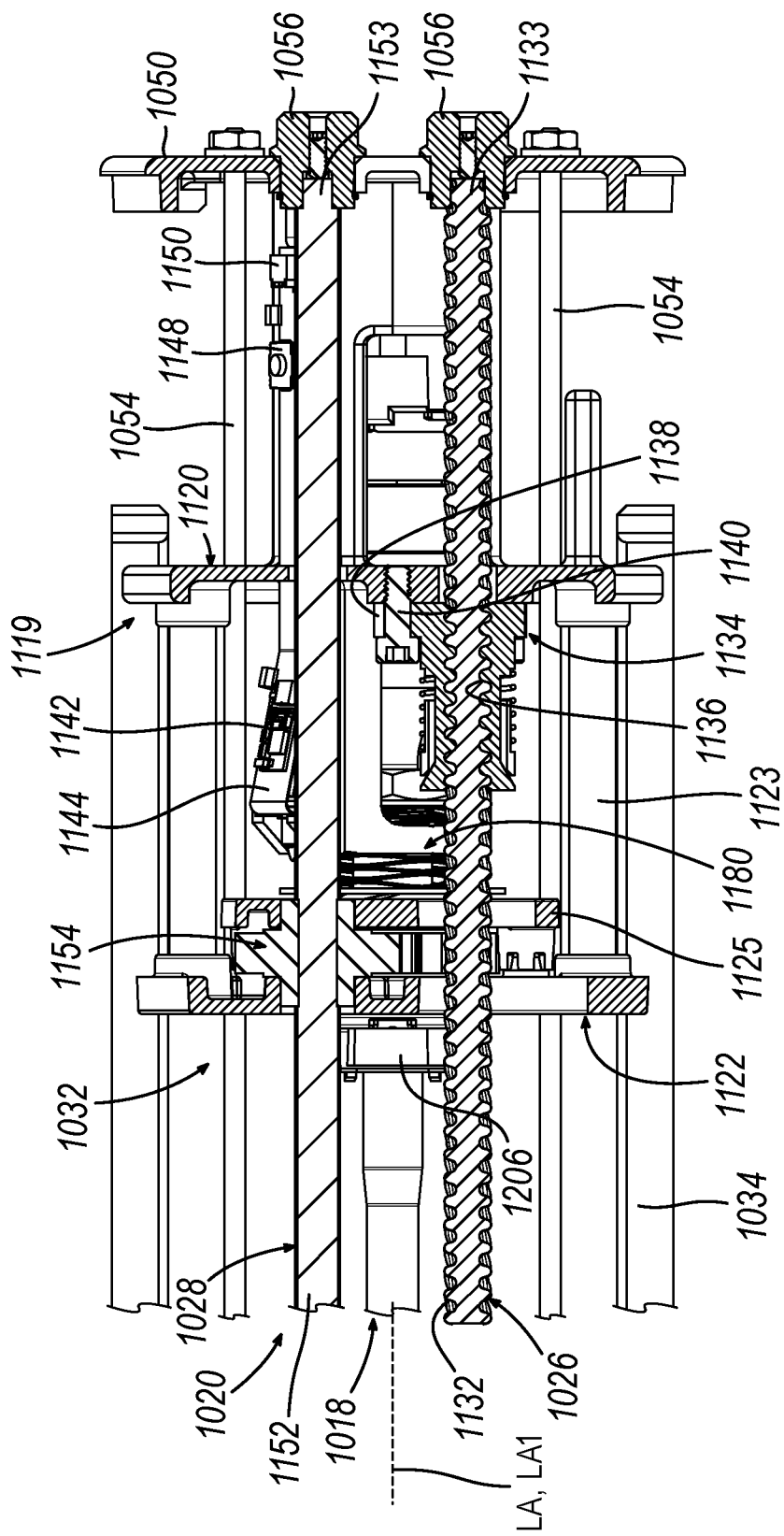
FIG. 18 depicts a cross-sectional view of the surgical instrument of FIG. 9, the cross-section being taken along section line 18-18 of FIG. 17.

As shown in FIGS. 9 through 11B, support structure (1014) is configured to guide carriage (1030) along longitudinal axis (LA). Support structure (1014) includes proximal and distal frame members (1050, 1052), at least one guide member (1054), and a distally extending guide shaft (1046). Distal frame member (1052) is spaced a distance along longitudinal axis (LA) from proximal frame member (1050). As shown in FIGS. 10 and 18, translation driver (1026) and actuation driver (1028) extend between proximal and distal frame members (1050, 1052) and are captured by corresponding fixation members (1056) at the proximal end. Fixation members (1056) allow for selective rotation of translation driver (1026) and actuation driver (1028). Fixation members (1056) also prevent translation of translation driver (1026) and actuation driver (1028) relative to proximal and distal frame members (1050, 1052). Guide members (1054), shown as cylindrical rods, extend between and are fixably coupled with proximal and distal frame members (1050, 1052). While two guide members (1054) are shown, more or fewer guide members (1054) are envisioned. Guide shaft (1046) is shown as extending distally from distal frame member (1052), which may include one or more coupled together components. As shown, an outer surface (1058) of guide shaft (1046) includes aligning feature (1044).

D. Exemplary Shaft Assembly

Surgical instrument (1010) includes shaft assembly (1018), which may be similar to shaft assembly (114) of surgical instrument (14). Shaft assembly (1018) is configured to extend from a center of instrument base (76) with an axis substantially parallel to the axes of the drive inputs (1038). With shaft assembly (1018) positioned at the center of instrument base (76), shaft assembly (1018) is coaxial with ultrasonic surgical instrument driver axis (74) when attached. Thus, rotation of rotational assembly (70) is configured to cause shaft assembly (1018) of surgical instrument (1010) to rotate about its own longitudinal axis. In other words, surgical instrument (1010) is configured to be rotated by rotational assembly (70) of robotic arm (32), such that individual components of surgical instrument (1010) (e.g., shaft assembly (1018)) do not need to rotate independently of other portions of surgical instrument (1010) Similar to surgical instrument (14), surgical instrument (1010) includes an instrument-based insertion architecture. Although not shown, it should be understood that in some examples, shaft assembly (1018) may include structures similar to articulation section (164) described above. As noted above, such structures may permit shaft assembly (1018) to bend or articulate at a predetermined point to promote greater flexibility in positioning shaft assembly (1018) within a patient. Of course, such structures for articulation of shaft assembly (1018) are merely optional and may be omitted in some examples.

Figure 12:
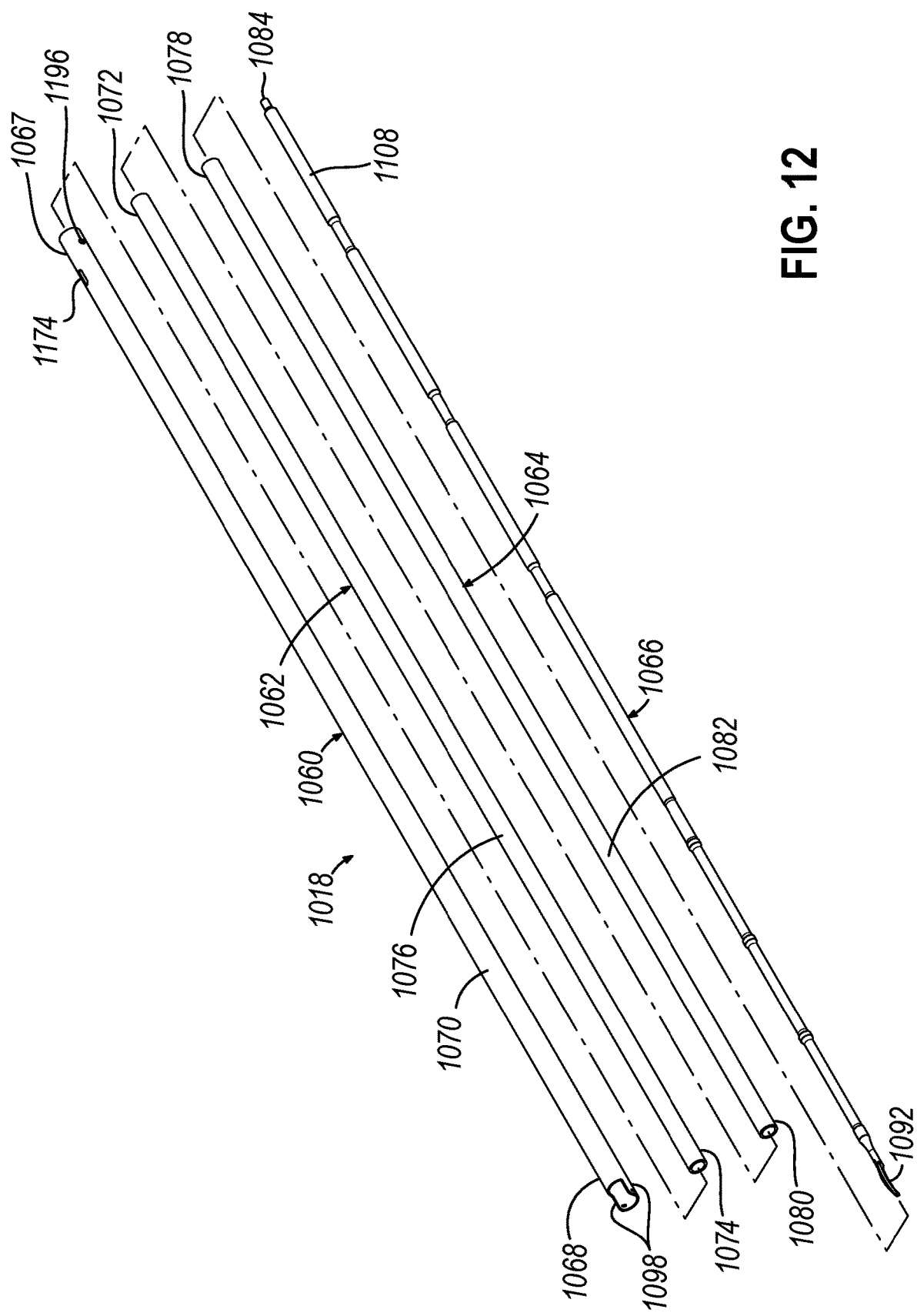
FIG. 12 depicts an exploded perspective view of the shaft assembly of FIG. 9.

As shown in FIG. 12, shaft assembly (1018) includes an outer shaft (1060), an inner shaft (1062), a sheath (1064), and an acoustic waveguide (1066). Acoustic waveguide (1066) extends at least partially within sheath (1064), and sheath (1064) extends at least partially within inner shaft (1062). Similarly, inner shaft (1062) extends at least partially within outer shaft (1060). Outer shaft (1060), also referred to as a closure member, includes proximal and distal ends (1067, 1068) and a hollow elongate body (1070) extending therebetween. Outer shaft (1060) extends along a longitudinal axis (LA1) that is shown as being coaxial with longitudinal axis (LA) defined by ultrasonic transducer assembly (1022). However, it is envisioned that longitudinal axis (LA) may be parallel to but offset a distance from longitudinal axis (LA1) or not be coaxial with longitudinal axis (LA1) in some versions. Inner shaft (1062) includes proximal and distal ends (1072, 1074), and a hollow elongate body (1076) extending therebetween. Similarly, sheath (1064) includes proximal and distal ends (1078, 1080), and a hollow elongate body (1082) extending therebetween. Acoustic waveguide (1066) includes threads (1084) disposed on a proximal end and ultrasonic blade (1092) disposed on a distal end which will now be described in greater detail.

E. Exemplary End Effector

Figure 13:
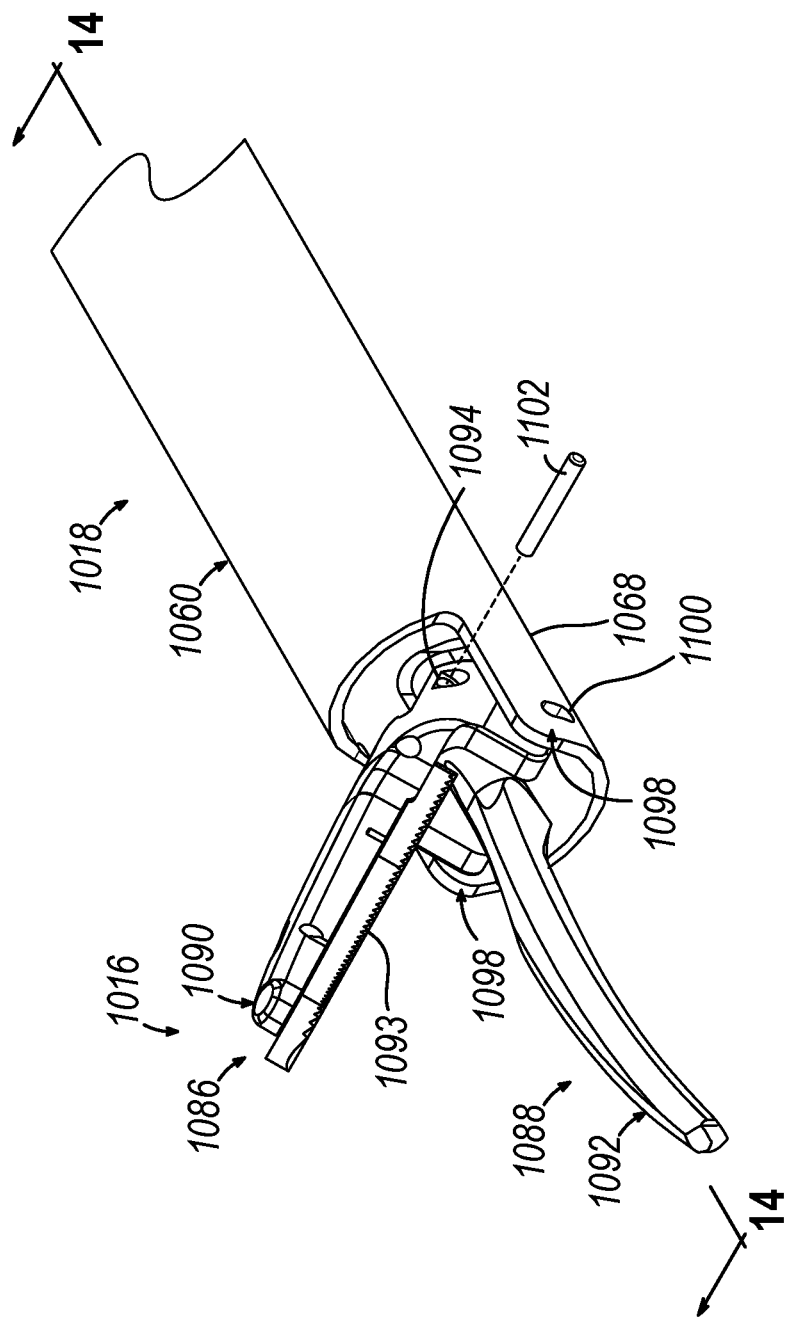
FIG. 13 depicts an enlarged perspective view of the end effector and the shaft assembly of FIG. 9.
Figure 14:
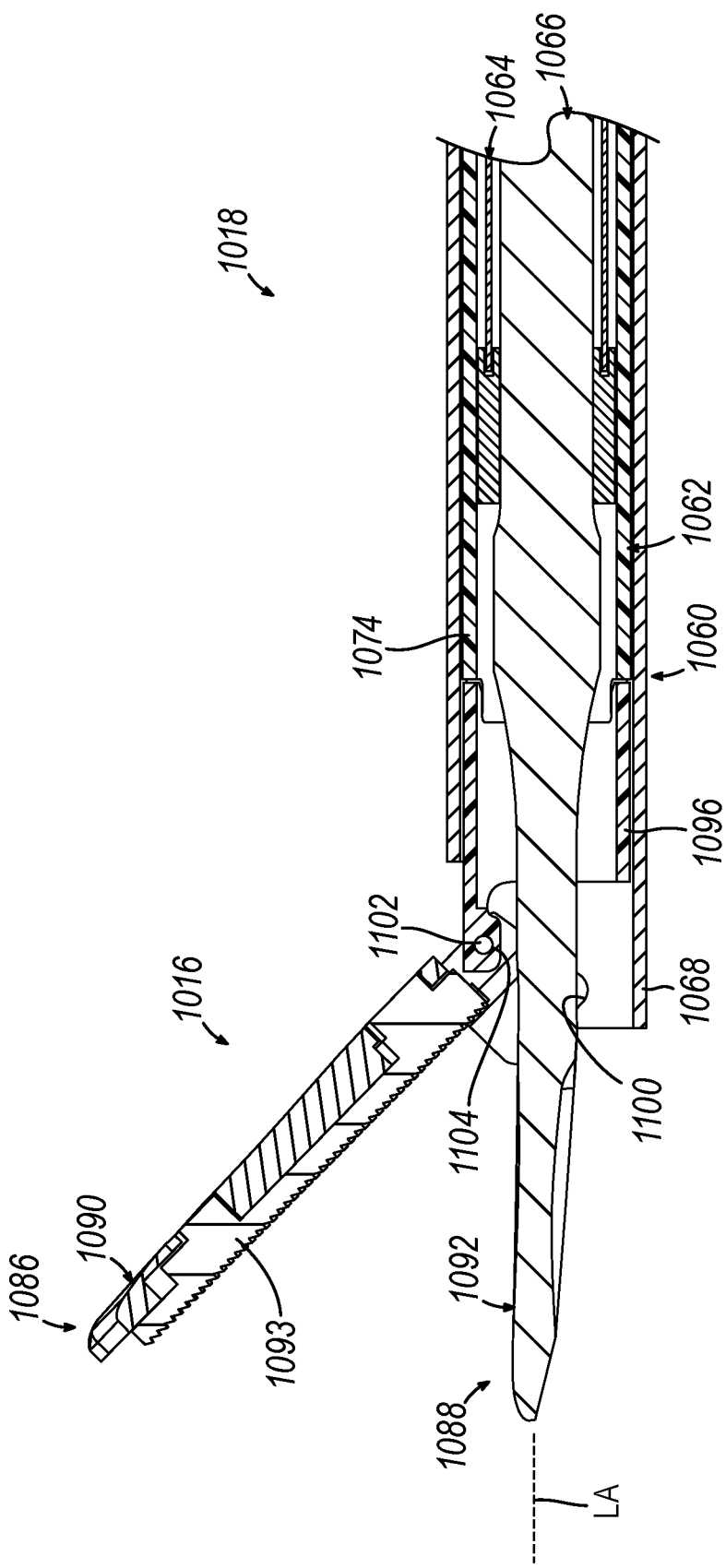
FIG. 14 depicts an enlarged cross-sectional view of the end effector and the shaft assembly of FIG. 13 taken along a centerline thereof.

End effector (1016) is shown and described in detail with reference to FIGS. 13-14, and may be similar to end effector (116) described above. Particularly, FIG. 13 shows end effector (1016) extending distally from shaft assembly (1018) of surgical instrument (1010) of FIG. 9, and FIG. 14 shows a cross-sectional view of end effector (1016) and shaft assembly (1018) of FIG. 13. At least one of first and second jaws (1086, 1088) is configured to pivot relative to the other of first and second jaws (1086, 1088) to compress tissue therebetween. Similar to end effector (116), first jaw (1086) includes a clamp arm (1090) and second jaw (1088) includes ultrasonic blade (1092). As will be described in greater detail below with reference to FIGS. 15-20, second rotational drive input (1038*b*) is configured to rotate actuation driver (1028) to actuate actuation assembly (1032) which translates outer shaft (1060) relative to inner shaft (1062) to selectively pivot clamp arm (1090) toward and away from ultrasonic blade (1092). Clamp arm (1090) selectively pivots to clamp tissue between clamp arm (1090) and ultrasonic blade (1092). Ultrasonic blade (1092) is operable to vibrate at ultrasonic frequencies in order to effectively cut through and seal tissue, particularly when the tissue is being compressed between the clamp pad (1093) and ultrasonic blade (1092). As such, ultrasonic blade (1092) is positioned at a distal end of the acoustic drivetrain. Similar to clamp arm (144) described above, clamp arm (1090) may include a clamp pad (1093) similar to clamp pad (148) described above. While ultrasonic blade (1092), clamp arm (1090), and clamp pad (1093) are shown as being arcuate (e.g., C-shaped) along longitudinal axis (LA), it is envisioned that one or more of ultrasonic blade (1092), clamp arm (1090), and clamp pad (1093) may extend along longitudinal axis (LA), similar to end effector (116) described above.

With continued reference to FIGS. 13-14, clamp arm (1090) may be pivotally coupled with inner shaft (1062) and outer shaft (1060). Clamp arm (1090) includes an upper recess (1094) extending perpendicular to the longitudinal axis (LA). As shown in FIGS. 13-14, clamp arm (1090) includes a pair of outwardly extending projections (1098) (one hidden) that interact with opposing pair of slots (1100) of outer shaft (1060). Distal end (1074) of inner shaft (1062) may be translatably coupled with a distal member (1096) that includes an upper recess (1104) configured to align with upper recess (1094) of clamp arm (1090) using a pivot pin (1102). In some versions, distal end (1074) of inner shaft (1062) may be directly coupled with clamp arm (1090). Pivot pin (1102) may be integrally formed together with clamp arm (1090) similar to outwardly extending projections (1098). Pivot pin (1102) may be disposed inside or be nested at least partially inside outer shaft (1060), instead of an arrangement where the distal end of clamp arm (1090) is disposed on the outside of outer shaft (1060). Pivot pin (1102) may be disposed within pair of slots (1100) of outer shaft (1060) (also referred to as the clamping tube) throughout the full range of motion of clamp arm (1090). Having pivot pin (1102) disposed inside or nested at least partially inside outer shaft (1060) may simplify the manufacturing of at least one of clamp arm (1090) and outer shaft (1060).

F. Exemplary Acoustic Drivetrain

Figure 16:
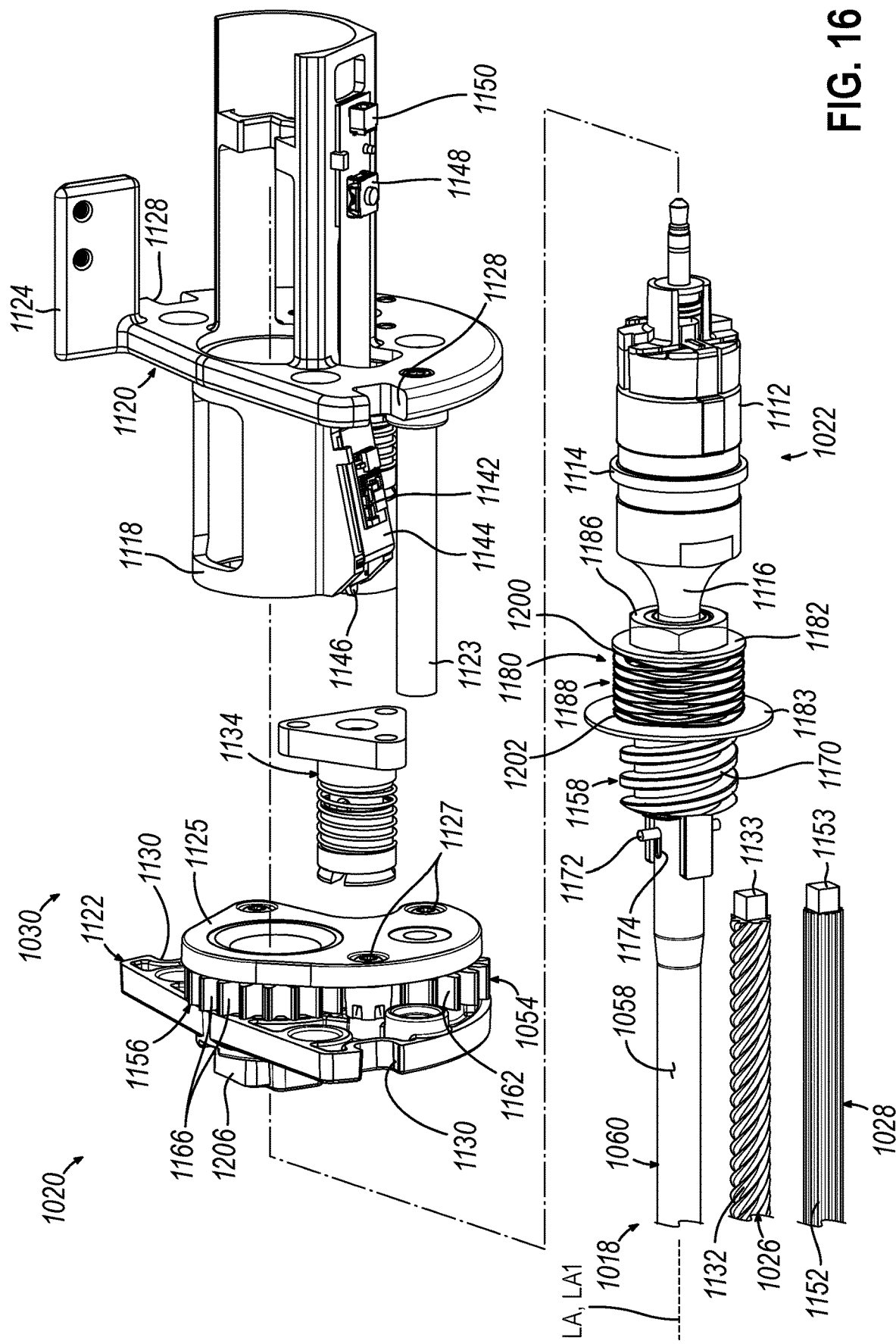
FIG. 16 depicts an exploded perspective view of the carrier of FIG. 15.
Figure 19:
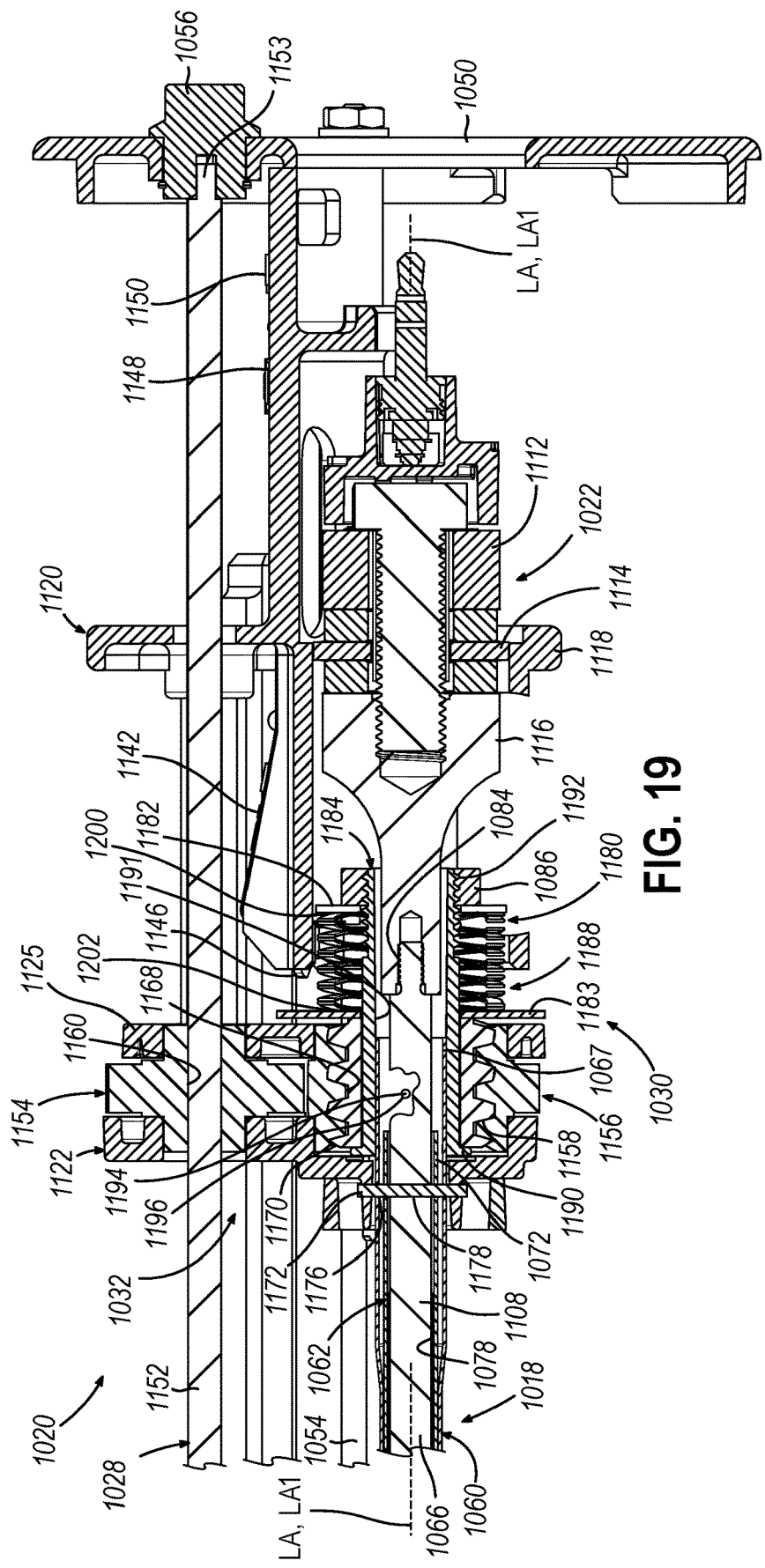
FIG. 19 depicts another cross-sectional view of the surgical instrument of FIG. 17, the cross-section being taken along section line 19-19 of FIG. 17.

As used herein, the acoustic drivetrain is intended to collectively refer to ultrasonic transducer assembly (1022) and acoustic waveguide (1066). Acoustic waveguide (1066) is in acoustic communication with ultrasonic blade (1092) of end effector (1016). At least a proximal portion (1108) of acoustic waveguide (1066) extends along a longitudinal axis (LA). Ultrasonic transducer assembly (1022) is coupled with a cable connector (1110) (see FIG. 10) and acoustic waveguide (1066) (see FIGS. 12 and 14). Ultrasonic transducer assembly (1022) is similar to ultrasonic transducer assembly (154) described above. As shown in FIGS. 10, 16, and 19, ultrasonic transducer assembly (1022) includes a transducer body (1112), an attachment flange (1114) extending outwardly from transducer body (1112), and a horn (1116) extending distally from transducer body (1112). Transducer body (1112) houses a plurality of piezoelectric elements (not shown). As shown in FIGS. 19 and 29A-29D, acoustic waveguide (1066) may be secured with the distal end of horn (1116). Attachment flange (1114) is generally configured to engage portions of transducer housing (1118) and/or proximal carriage frame member (1120) to fixedly secure transducer assembly (1022) with carriage (1030). However, ultrasonic transducer assembly (1022) may be coupled with transducer housing (1118) using a variety of suitable structures including one or more fasteners, or a press fit, or compression fit.

Exemplary embodiments of ultrasonic blade (1092), acoustic waveguide (1066) and/or ultrasonic transducer assembly (1022) are shown and described in detail in U.S. patent application Ser. No. 17/077,139, entitled "Ultrasonic Surgical Instrument with a Fixed Transducer Grounding," filed on Oct. 22, 2020, published as U.S. Pub. No. 2022/012471 on Apr. 28, 2022, the disclosure of which is incorporated by reference herein. Ultrasonic blade (1092), acoustic waveguide (1066), and ultrasonic transducer assembly (1022) may collectively comprise a fixed length. Additionally, sheath (1064) may acoustically insulate acoustic waveguide (1066). Similar to ultrasonic transducer assembly (154), ultrasonic transducer assembly (1022) of the present example may be connected with a generator (not shown) similar to generator (155) of the acoustic drivetrain. Thus, the generator may be used to apply electric power to transducer assembly (1022) to activate piezoelectric elements (not shown) in transducer assembly (1022) and thereby convert the electrical power into ultrasonic vibrations. By way of example only, as with generator (154) described above, suitable generators may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

G. Exemplary Carrier

Surgical instrument (1010) includes various drive components configured to move shaft assembly (1018) between a proximal position and a distal position and to actuate end effector (1016). Similar to surgical instrument (14), surgical instrument (1010) may use various features configured to facilitate movement between end effector (1016) and drive inputs (e.g., first and second rotational drive inputs (1038a-b)), such features may additionally or alternatively include pulleys, cables, carriers, such as a KART, and/or other structures configured to communicate movement along shaft assembly (1018). To facilitate instrument-based insertion, insertion of shaft assembly (1018) is grounded at instrument base (76) such that end effector (1016) is configured to selectively move longitudinally along longitudinal axis (LA) from the proximal position to the distal position, vice versa, and any desired longitudinal position therebetween.

Figure 11A:
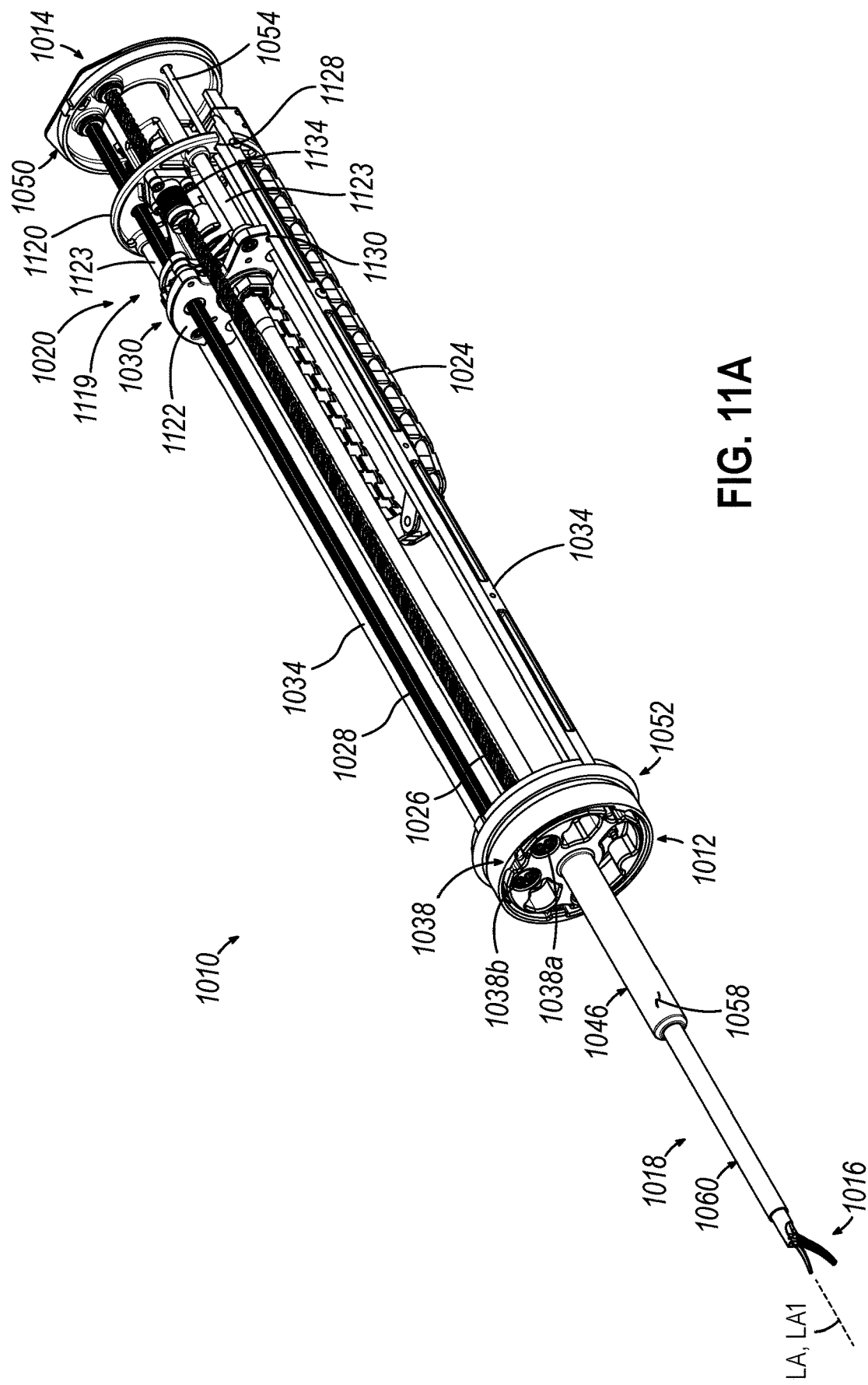
FIG. 11A depicts a perspective view of the surgical instrument of FIG. 9 with a carriage of the carrier and the shaft assembly of FIG. 9 in a proximal position.
Figure 11B:
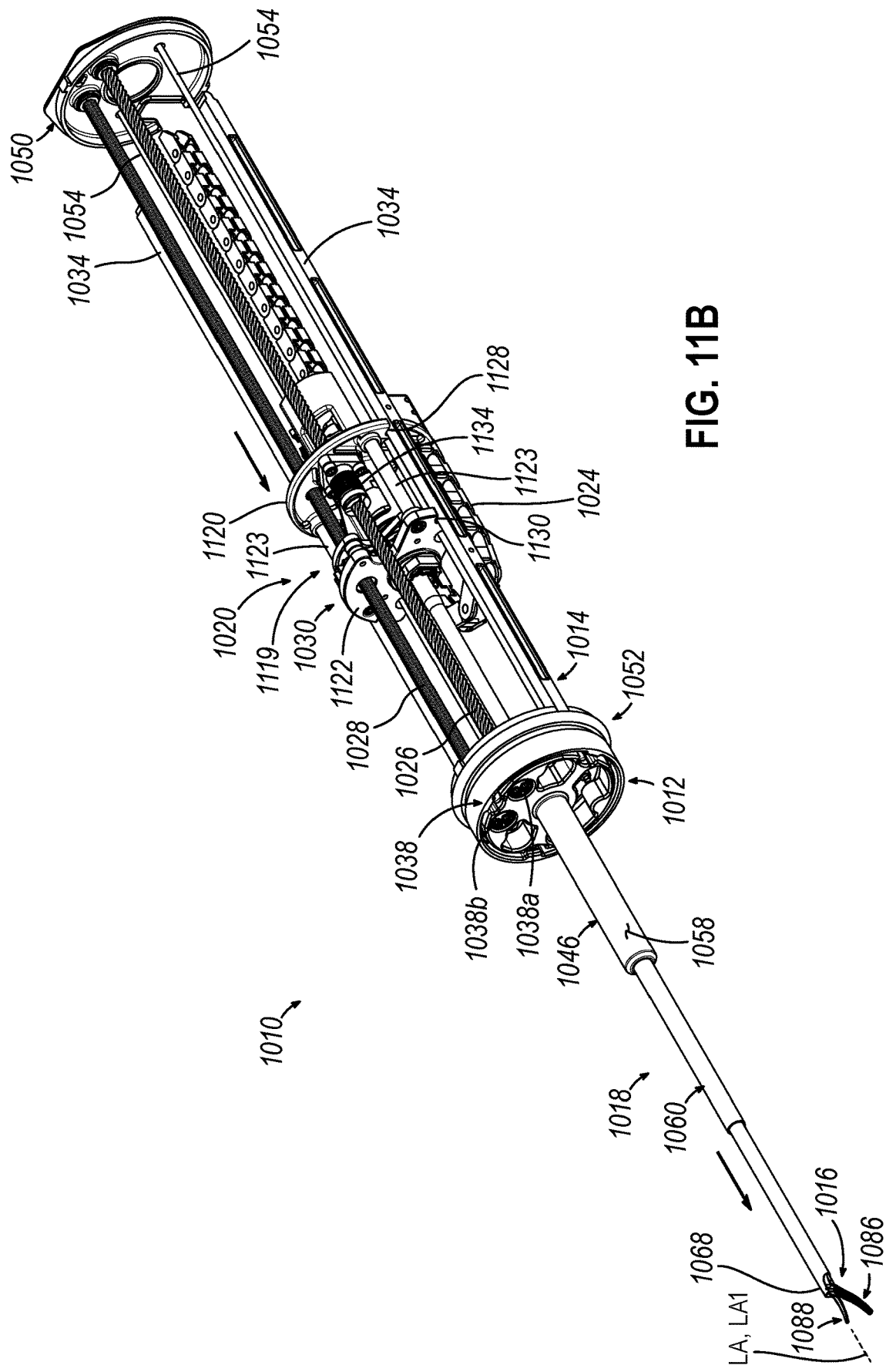
FIG. 11B depicts the perspective view of the surgical instrument similar to FIG. 11A, but with carriage and the shaft assembly of FIG. 9 extended to a distal position.

FIG. 11A shows a perspective view of surgical instrument (1010) of FIG. 9 with carriage (1030) of carrier (1020) and shaft assembly (1018) in an exemplary proximal position (also referred to as a retracted position). As shown, the proximal position places end effector (1016) relatively close and proximally toward instrument base (76). Conversely, FIG. 11B shows a perspective view of surgical instrument (1010) of FIG. 11A, but with carriage (1030) of carrier (1020) and shaft assembly (1018) extended to an exemplary distal position (also referred to as an extended position). As shown in FIG. 11B, the distal position places end effector (1016) relatively far and distally away from instrument base (76). While exemplary proximal and distal positions are shown, carriage (1030) may translate along the length of translation driver (1026) to place end effector (1016) at the desired position. For example, one or more intermediate positions, between the illustrated proximal and distal positions are envisioned but not shown. Additionally, while not shown, carriage (1030) may further translate distally to further distally advance shaft assembly (1018) and end effector (1016). Insertion into and withdrawal of end effector (1016) relative to the patient may be facilitated by surgical instrument (1010), although it will be appreciated that such insertion into and withdrawal may also occur via robotic arms (32) in one or more examples. As shown in the transition from FIG. 11A to FIG. 11B, translation driver (1026) translates carriage (1030) and ultrasonic transducer assembly (1022) along longitudinal axis (LA), so that ultrasonic transducer assembly (1022) moves from the proximal position along longitudinal axis (LA) to the distal position along longitudinal axis (LA) for inserting ultrasonic blade (1092) into the patient.

Figure 15:
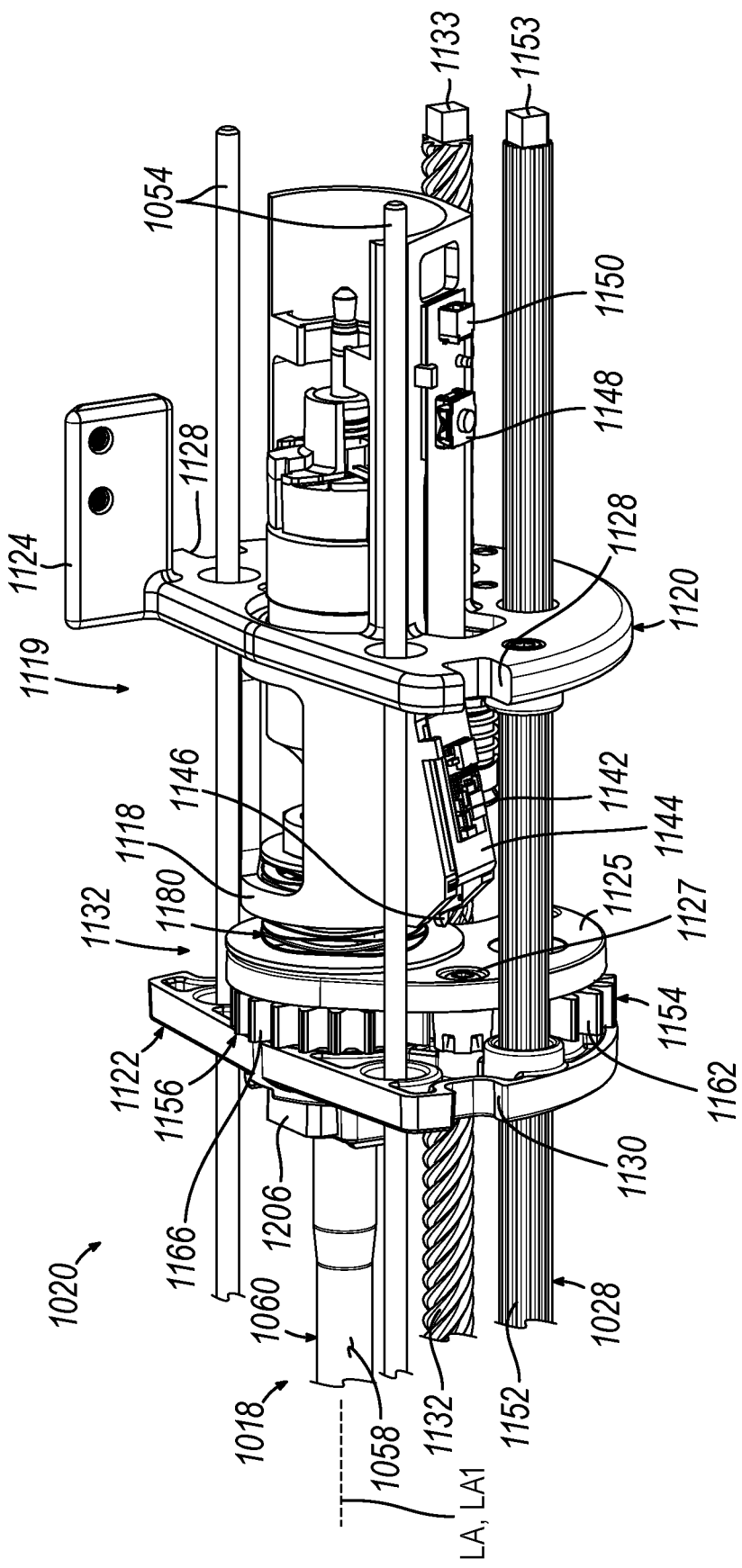
FIG. 15 depicts an enlarged perspective view of the carrier of FIG. 9.
Figure 17:
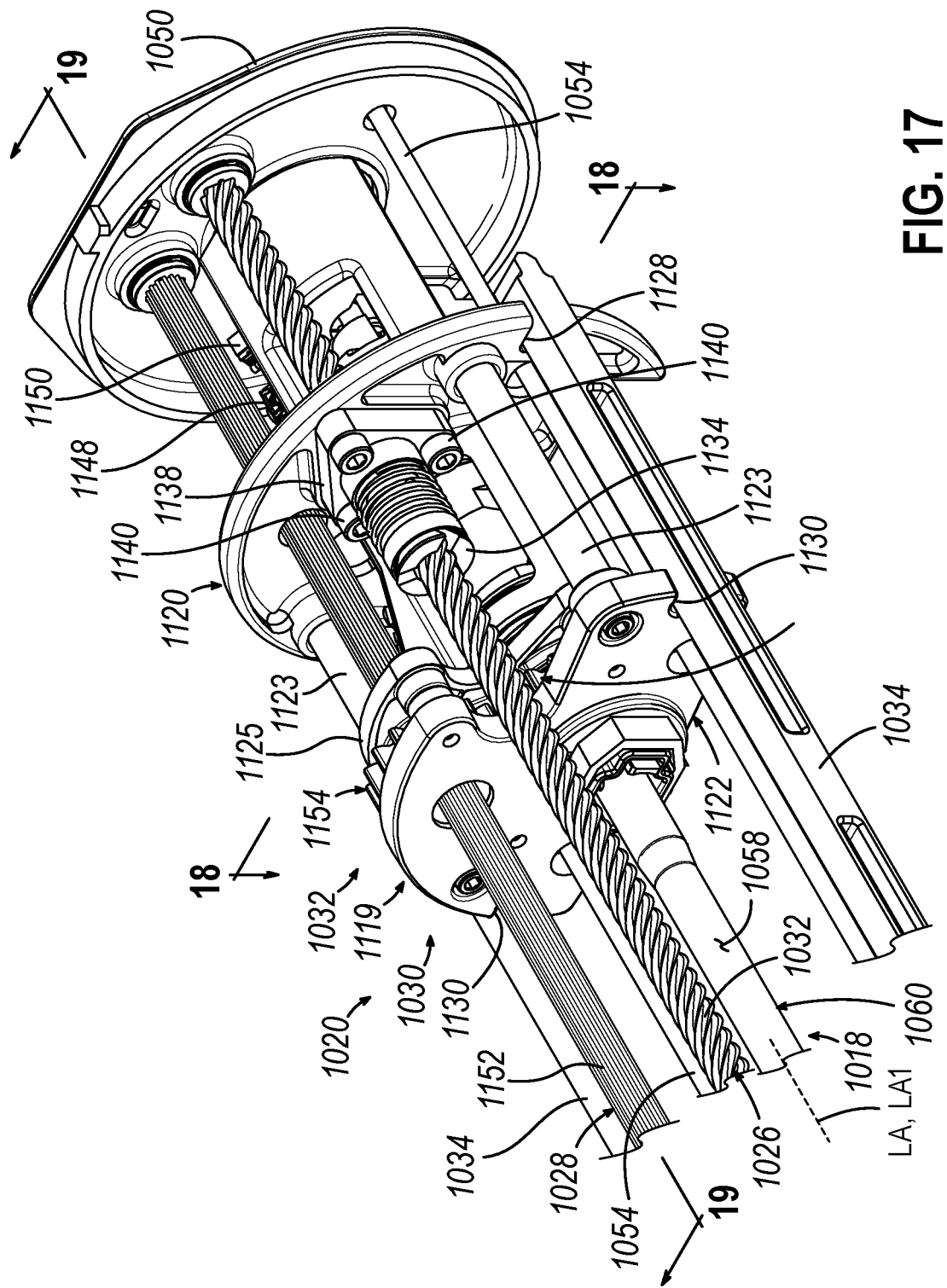
FIG. 17 depicts another enlarged perspective view of the carrier of FIG. 15.

Carrier (1020) is now described in greater detail with reference to FIGS. 15-20. As previously described, carrier (1020) includes translation driver (1026), actuation driver (1028), carriage (1030), and guide rails (1034). Particularly, FIGS. 15 and 17 show enlarged perspective views of carrier (1020) of FIG. 9, and FIG. 16 shows an exploded perspective view of carrier (1020) of FIG. 12. As previously described, carrier (1020) is translatably coupled with ultrasonic transducer assembly (1022). Carriage (1030) includes a carriage support structure (1119). Carriage support structure (1119) includes proximal and distal carriage frame members (1120, 1122) and one or more carriage guide members (1123) extending between and fixably coupled with proximal and distal carriage frame members (1120, 1122). Proximal carriage frame member (1120) is spaced a distance (D) along longitudinal axis (LA) from distal carriage frame member (1122). A flange (1124) of proximal carriage frame member (1120) may be coupled with flexible cable guide (1024) using one or more fasteners (1126). Proximal carriage frame member (1120) includes a transducer housing (1118) that includes a generally hollow cylindrical shape integral with, and extending distally from, proximal carriage frame member (1120). Transducer housing (1118) is generally configured to receive a portion of ultrasonic transducer assembly (1022). Transducer housing (1118) and/or portions of proximal carriage frame member (1120) are generally configured to act as a ground for ultrasonic transducer assembly (1022) relative to surgical instrument (1010). Carriage guide member (1123) is configured to guide carriage (1030) along longitudinal axis (LA). Carriage support structure (1119) may also include an intermediate carriage frame member (1125) disposed between proximal and distal carriage frame members (1120, 1122). Intermediate carriage frame member (1125) may be coupled with proximal carriage frame member (1120) using one or more fasteners (1127) to translatably fix first and second spur gears (1154, 1156) therebetween.

Carriage (1030) is positioned between guide rails (1034) such that carriage (1030) is generally configured to move axially along guide rails (1034) under the influence of translation driver (1026). Guide rails (1034) extend axially at least partially between proximal and distal frame members (1050, 1052). Proximal and distal carriage frame members (1120, 1122) include a plurality of guide slots (1128, 1130) configured to receive guide rails (1034). Thus, proximal and distal carriage frame members (1120, 1122) are both configured to confine movement of carriage (1030) along the path defined by guide rails (1034) via guide slots (1128, 1130) of respective proximal and distal carriage frame members (1120, 1122). Imbalanced loads may cause carriage (1030) to twist. Guide rails (1034) may provide structural stiffness to reduce the torsional forces exerted on proximal and distal carriage frame members (1120, 1122) due to rotation of actuation driver (1028). Although guide slots (1128, 1130) in the present example are configured as slots corresponding to the shape of guide rails (1034), it should be understood that in other examples, alternative forms of engagement between proximal and distal carriage frame members (1120, 1122) and guide rails (1034) may be used. For instance, in some examples, guide rails (1034) may include one or more slots, such as channels, while proximal and distal carriage frame members (1120, 1122) may include one or more protrusions configured for insertion into such slots or channels. Of course, various other forms of engagement may be used as will be apparent to those of ordinary skill in the art in view of the teachings herein. Guide rails (1034) may be supported by and coupled to cylindrical housing (1036) of surgical instrument (1010). Cylindrical housing (1036) may assist guide rails (1034) in providing structural stiffness to reduce torsional deflection of carriage (1030). Guide rails (1034) are generally configured to guide or otherwise direct movement of carrier (1020) along a predetermined axial path. To facilitate this functionality, guide rails (1034) of the present example are generally configured as elongate rails having a square or a rectangular cross-section. However, it should be understood that in other examples, guide rails (1034) may take on a variety of elongate rail forms such as cylindrical, C-shaped, I-shaped, etc.

i. Translation of End Effector Using Carrier

FIG. 17 shows a perspective view of carrier (1020) similar to FIG. 15 from another angle. Translation driver (1026) and actuation driver (1028) are described in greater detail with reference to FIG. 18. Particularly, FIG. 18 shows a cross-sectional view of surgical instrument (1010) of FIG. 17, where the cross-section is taken along section line 18-18 of FIG. 17. More specifically, the cross-section of FIG. 18 is taken along translation driver (1026) and along actuation driver (1028). Translation driver (1026) is generally configured to drive translation of carriage (1030) by rotating translation driver (1026) using drive output (68) of robotic arm (32). Translation driver (1026) is shown as including a threaded lead screw (1132), which may engage with one or more threaded components (e.g., a threaded receiver (1134)) associated with carriage (1030) to thereby convert rotary motion of translation driver (1026) into translation of carriage (1030). As shown in FIGS. 10 and 15, threaded lead screw (1132) includes end features (1133), shown as squared off proximal and distal ends, to receive first rotational input (1038a) and fixation member (1056). While threaded lead screw (1132) is shown and described in the present example, it should be understood that in other examples various alternative configurations of translation driver (1026) may be used in addition to or in lieu of threaded lead screw (1132). Suitable alternative configurations may include components such as cable and pulley combinations, gears, linear actuators, fluid or pneumatically actuated pistons, and/or etc.

The translation of end effector (1016) is now described in greater detail. Referring back to FIG. 9, drive output (68) of robotic arm (32) communicates rotary motion from robotic arm (32) to sterile adapter (1040). Sterile adapter (1040) transmits the rotary motion to first rotational drive input (1038a). First rotational drive input (1038a) then transmits the rotary motion to translation driver (1026). As shown in FIGS. 17-18, translation driver (1026) then transmits the rotary motion to threaded receiver (1134) which includes internal threads (1136). Threaded receiver (1134) is rotatably coupled with proximal carriage frame member (1120) using a distal frame attachment member (1138) and fasteners (1140). Since distal carriage frame member (1122) is prevented from rotating using at least guide rails (1034) and carriage guide members (1123), carriage (1030), which includes proximal and distal carriage frame members (1120, 1122), translates along translation driver (1026). Since distal carriage frame member (1122) is coupled with proximal carriage frame member (1120) using carriage guide members (1123), proximal carriage frame member (1120) pushes distal carriage frame member (1122) along during distal movement and pulls distal carriage frame member (1122) along during proximal movement. While not shown, proximal translation of translating member (1158) causes proximal translation of outer shaft (1060).

Since carriage (1030) translates along translation driver (1026), a number of components may also be translated together with carriage (1030). For example, carriage (1030) includes a circuit board (1142) operatively coupled with carriage (1030) using a support plate (1144), so that circuit board (1142) is configured to translate together with carriage (1030) along longitudinal axis (LA). An optional electronic switch (1146) may be electrically coupled with circuit board (1142). Carriage (1030) includes cable connector (1110) (see FIG. 10) configured to provide power to ultrasonic transducer assembly (1022). Likewise, cable connector (1110) is configured to translate together with carriage (1030) along longitudinal axis (LA). Referring back to FIG. 15, carriage (1030) also includes an activation device (1148), shown as a pushbutton, configured to activate surgical instrument (1010) and a connector switch (1150), both of which are configured to translate together with carriage (1030).

ii. Actuation of End Effector Using Carrier

Figure 20:
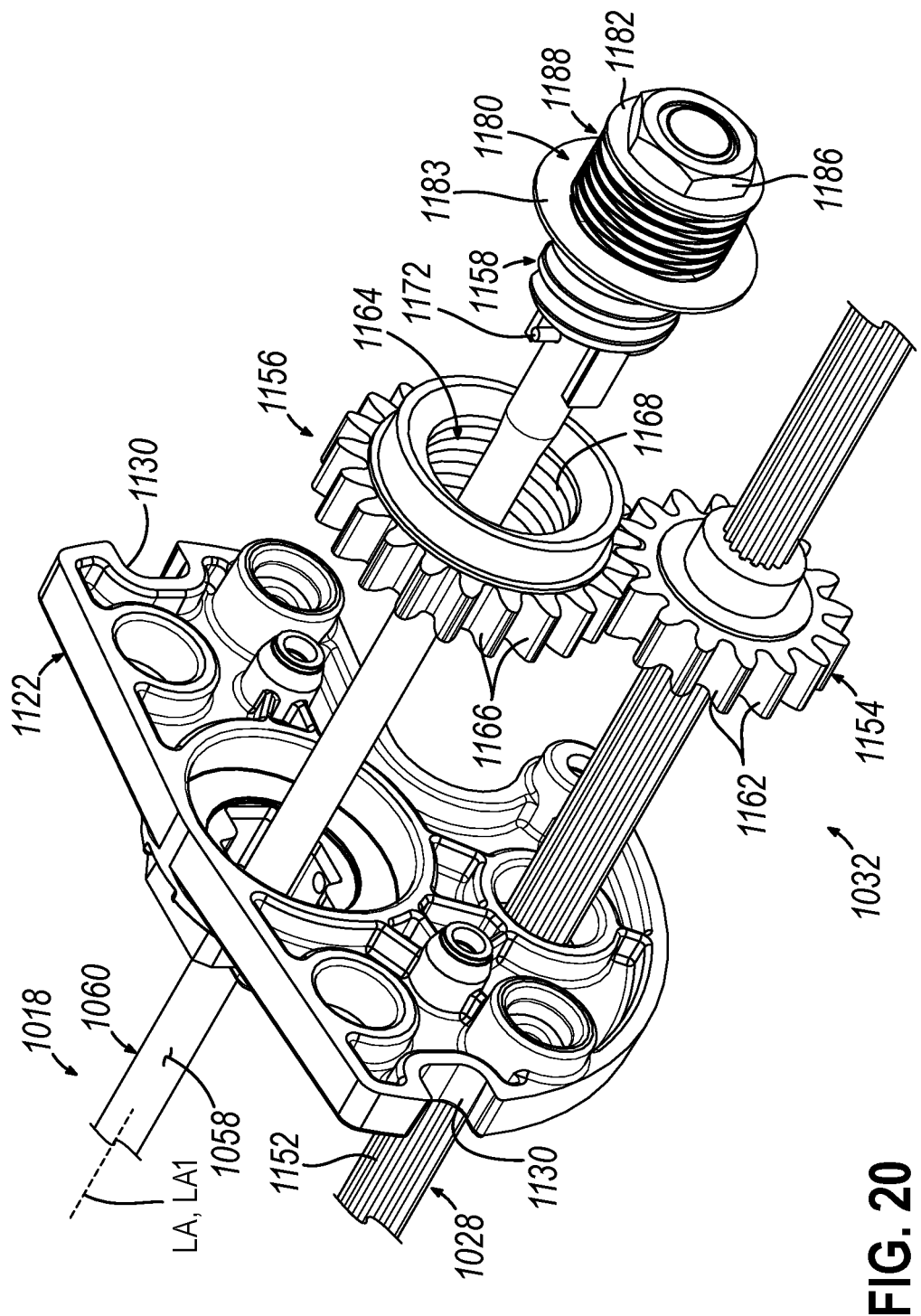
FIG. 20 depicts a perspective view of portions of the carrier and the shaft assembly of FIG. 9, with the carrier including an actuation assembly with a closure force adjusting mechanism.

As shown in FIGS. 15-20 and described in greater detail with reference to FIGS. 27-29D, actuation driver (1028) is generally configured to selectively drive various portions of surgical instrument (1010) from one or more drive outputs (68) of robotic arm (32). For instance, in the present example, actuation driver (1028) includes a splined shaft (1152) (i.e., an elongate spur gear) configured to drive rotation of various components within carriage (1030) as carriage (1030) is moved using actuation driver (1028). Rotation provided by actuation driver (1028) is used to actuate end effector (1016) between the open position and the closed position. As shown in FIGS. 15, 16, and 18, splined shaft (1152) includes end features (1153), shown as squared off proximal and distal ends to receive second rotational input (1038b) and fixation member (1056). FIG. 19 shows a cross-sectional view of surgical instrument (1010) of FIG. 17, where the cross-section is taken along section line 19-19 of FIG. 17. Additionally, FIG. 20 shows a perspective view of actuation assembly (1032) coupled with splined shaft (1152) of actuation driver (1028) and shaft assembly (1018). Actuation assembly (1032) is configured to translate a portion (e.g., outer shaft (1060)) of shaft assembly (1018) causing clamp arm (1090) to pivot relative to ultrasonic blade (1092) (see FIGS. 13-14).

As shown in FIGS. 15-20, actuation assembly (1032) includes a first spur gear (1154), a second spur gear (1156), and a translating member (1158). As shown in FIG. 18, first spur gear (1154) is rotatably coupled with splined shaft (1152). First spur gear (1154) includes an internal aperture (1160) having a corresponding spline pattern to rotatably couple with splined shaft (1152). First spur gear (1154) also includes a first plurality of gear teeth (1162). While first spur gear (1154) is shown as having 16 individual gear teeth (1162), more or fewer gear teeth are also envisioned. Second spur gear (1156) includes a central aperture (1164) and a second plurality of gear teeth (1166). While second spur gear (1156) is shown as having 21 individual gear teeth (1166), more or fewer gear teeth are also envisioned. At least a portion of central aperture (1164) of second spur gear (1156) includes internal threading (1168). Translating member (1158) (which may include a lead screw) includes external threading (1170). Rotation of internal threading (1168) of second spur gear (1156) relative to external threading (1170) of translating member (1158) is configured to translate translating member (1158) either proximally or distally. As shown in FIG. 19, a coupling pin (1172) may couple an elongate slot (1174) of outer shaft (1060), an aperture (1176) of inner shaft (1062), and a through bore (1178) of acoustic waveguide (1066). As shown, coupling pin (1172) may extend perpendicular to the longitudinal axis (LA).

As will be described in greater detail with reference to FIGS. 27-33, actuation assembly (1032) may include an optional closure force adjusting mechanism (1180), a proximal washer (1182), a distal washer (1183), a elongate shaft (1184), and a tuning member (1186). Closure force adjusting mechanism (1180) is configured to selectively adjust the closure force while compressing the tissue between first and second jaws (1086, 1088). According to an exemplary embodiment, closure force adjusting mechanism (1180) may include a resilient member (shown as a wave spring (1188)) configured to adjust the closure force between first and second jaws (1086, 1088). However, other closure force adjusting mechanisms (1180) are also envisioned. In some versions, wave spring (1188) may adjust the closure force of clamp arm (1090) when wave spring (1188) moves from a non-compressed state (see FIGS. 29A-29B) to a partially compressed state (see FIG. 29C) and to a fully compressed state (see FIG. 29D) when outer shaft (1060) is translated relative to second spur gear (1156).

Figure 28:
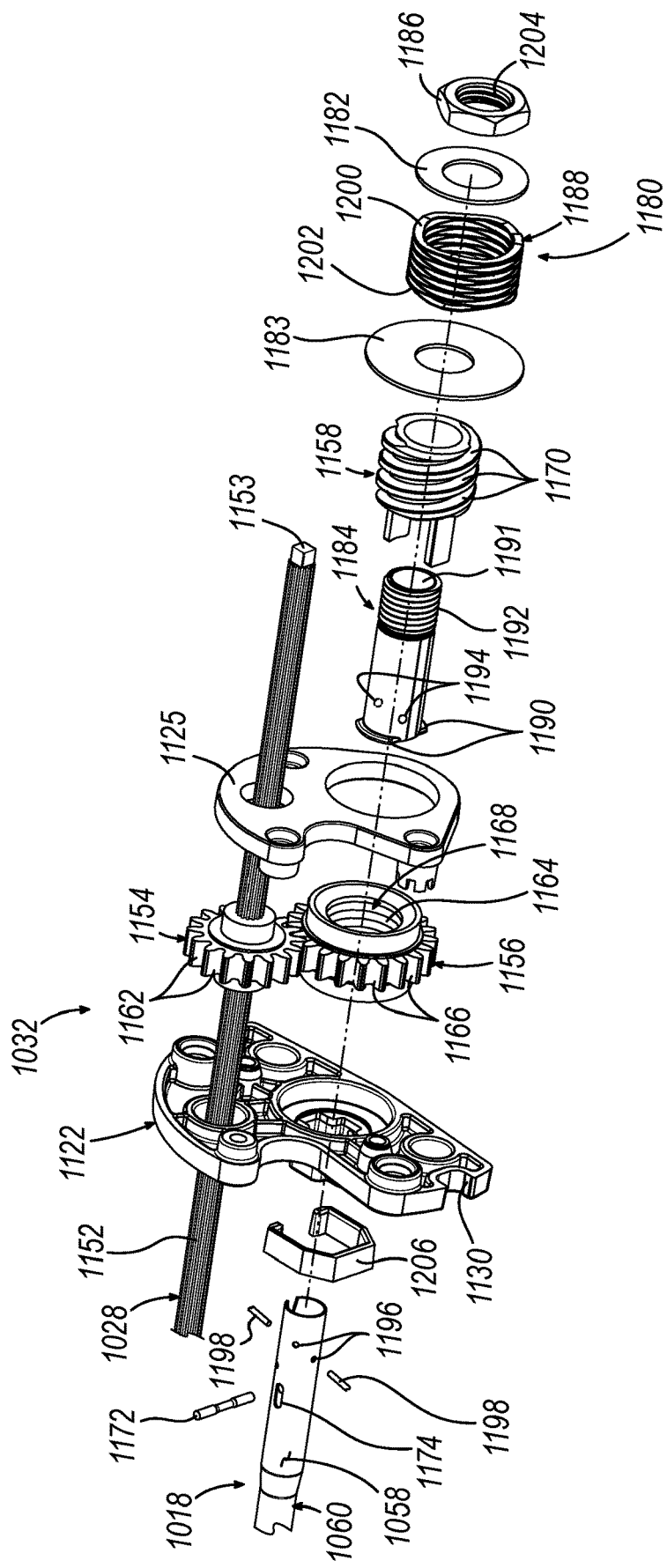
FIG. 28 depicts an exploded perspective view of portions of the carrier and the shaft assembly of FIG. 27.

Elongate shaft (1184) includes a flange (1190) at a distal end, a central through hole (1191) and external threading (1192) at a proximal end. As shown in the cutout portion of FIG. 19 and the exploded view of FIG. 28, elongate shaft (1184) also includes an aperture (1194) that extends perpendicular to the longitudinal axis that is configured to align with an aperture (1196) of outer shaft (1060). As shown in FIG. 28, in some versions, one or more temporary couplings (1198) may extend within apertures (1194, 1196) to temporarily fix elongate shaft (1184) relative to outer shaft (1060) while elongate shaft (1184) and outer shaft (1060) are being fixably coupled together (e.g., using one or more welds or another suitable fastening structure). In some versions, apertures (1194, 1196) may be omitted. Proximal washer (1182) is disposed adjacent proximal terminal end (1200) of wave spring (1188). Distal washer (1183) is disposed adjacent distal terminal end (1202) of wave spring (1188). Tuning member (1186) is disposed adjacent proximal washer (1182) and includes internal threading (1204). While tuning member (1186) is shown as a threaded nut, tuning member (1186) may include a variety of suitable forms. Tuning member (1186) may adjust a closure distance of translating member (1158) by adjusting the position of tuning member (1186) relative to elongate shaft (1184) using the interface between external and internal threading (1192, 1204). Adjusting the closure distance affects the closure force when optional closure force adjusting mechanisms (1180) is included.

The actuation of clamp arm (1090) is now described in greater detail. Referring back to FIG. 9, drive output (68) of robotic arm (32) communicates rotary motion in a first direction from robotic arm (32) to sterile adapter (1040). Sterile adapter (1040) then transmits the rotary motion in the first direction to second rotational drive input (1038b). In some versions, sterile adapter (1040) may be omitted. Second rotational drive input (1038b) then transmits the rotary motion in the first direction to actuation driver (1028), which may include splined shaft (1152). As shown in FIGS. 27-29D, rotation in the first direction of splined shaft (1152) then rotates first spur gear (1154) about an axis defined by the splined shaft (1152), as internal aperture (1160) of first spur gear (1154) is rotatably coupled with splined shaft (1152). Rotation of first spur gear (1154) then rotates second spur gear (1156) in an opposite direction as gear teeth (1162) of first spur gear (1154) are engaged with gear teeth (1166) of second spur gear (1156). Rotation of second spur gear (1156) translates translating member (1158) which includes external threading (1170) threadably engaged with internal threading (1168) of second spur gear (1156). Proximal translation of translating member (1158) causes proximal translation of outer shaft (1060), as outer shaft (1060) is coupled with elongate shaft (1184). Proximal movement of outer shaft (1060) causes clamp arm (1090) to pivot relative to ultrasonic blade (1092).

As shown, actuation driver (1028) provides the sole single input from robotic arm (32) to pivot clamp arm (1090) relative to ultrasonic blade (1092). In addition, or in the alternative, in some examples, multiple actuation drivers (not shown) may be used to drive multiple components of surgical instrument (1010) independently. It should be understood that actuation driver (1028) may be associated with additional drive components such as gears, cams, links, cranks, lead screws, and the like to drive movement of end effector (1016) using rotary input provided by actuation driver (1028). Although actuation driver (1028) is described herein as being configured to selectively drive movement of end effector (1016), in other examples, actuation driver (1028) can be used to drive other suitable components of surgical instrument (1010). Of course, various alternative applications of actuation driver (1028) will be apparent to those of ordinary skill in the art in view of the teachings herein.

Figure 21:
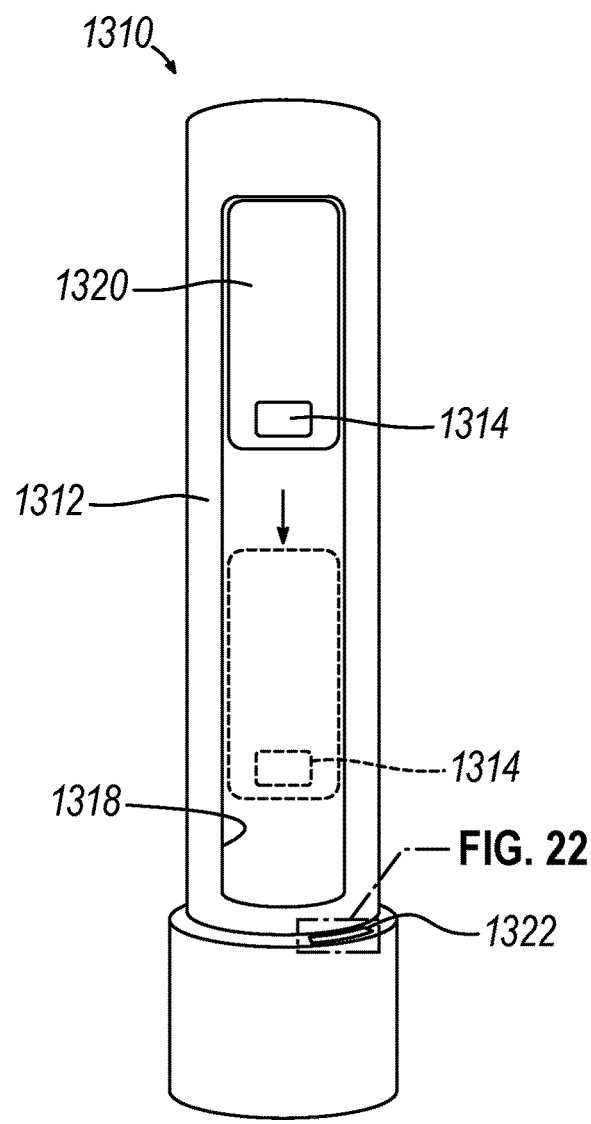
FIG. 21 depicts a schematic perspective view of a third exemplary surgical instrument that includes a translating activation mechanism and a manual jaw actuation mechanism.

H. Exemplary Translating Activation Mechanism and Exemplary Manual Jaw Actuation Mechanism FIG. 21 shows a schematic perspective view of a third exemplary surgical instrument (1310) similar to surgical instrument (1010). Surgical instrument (1310) includes a housing (1312), an exemplary translating activation mechanism (1314), and a manual jaw actuation mechanism (1316). Housing (1312) includes a slot (1318) configured to receive a carriage (1320) similar manner to carriage (1030) (see FIG. 19). Carriage (1320) is configured to translate along housing (1312) in a similar manner to carriage (1030) (see FIG. 19) described above. As shown, translating activation mechanism (1314) is translatably coupled with carriage (1320). Translating activation mechanism (1314) may allow the user to activate surgical instrument (1310).

It may be beneficial to manually operate first and second jaws (not shown) but similar to first and second jaws (1086, 1088) described above and first and second jaws (1352, 1354) described below, for a variety of reasons. These reasons may include in case of power loss, to facilitate cleaning the first and second jaws (e.g., after removing surgical instrument (1310) from robotic system (10, 28)), and/or for other reasons. Manual operation of first and second jaws (1086, 1088) may include manually opening first and second jaws (1086, 1088) and/or manually closing first and second jaws (1086, 1088). Manually opening first and second jaws (1086, 1088) may allow for first and second jaws (1086, 1088) to release grasped tissue. Manually closing first and second jaws (1086, 1088) may allow surgical instrument (1310) to be removed through a cannula (not shown). In some instances, first and second jaws (1086, 1088) may be manually opened first to release tissue then manually closed to remove surgical instrument (1310) from the patient.

Figure 22:
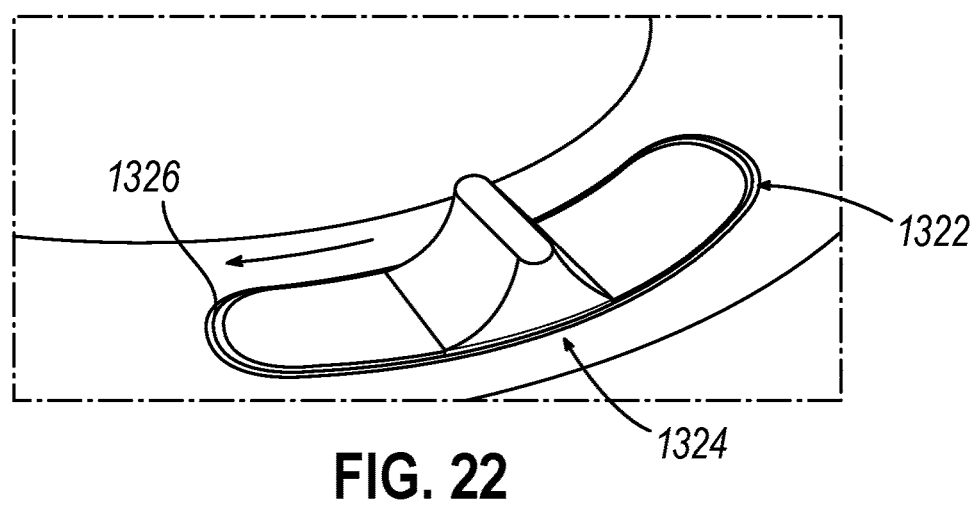
FIG. 22 depicts an enlarged perspective view of the manual jaw actuation mechanism of FIG. 21.

FIG. 22 shows an enlarged schematic perspective view of manual jaw actuation mechanism (1316) of FIG. 21. As shown, manual jaw actuation mechanism (1322) may include a slider (1324). Rotating slider (1324) along a slot (1326) may affect first or second spur gears (not shown), but similar to first and second spur gears (1154, 1156) that affect the translation driver and the translating closure member (e.g., which may be similar to outer shaft (1060)). Manual jaw actuation mechanism (1316) may provide for operation of the first and second jaws (e.g., first and second jaws (1086, 1088)) without significant added mechanical complexity to clamp arm (1090) and the translating closure member.

I. Third Exemplary End Effector

FIGS. 23-24 show a third exemplary end effector (1350) configured to compress, cut, and staple tissue. Particularly, FIG. 23 shows end effector (1350) configured for use with the surgical instrument (1010) of FIG. 9 in an open position. End effector (1350) of the present example includes first and second jaws (1352, 1354). First jaw (1352) includes a pivotable anvil (1358), and second jaw (1354) includes a staple cartridge (1356). As shown, end effector (1350) employs a firing beam (1360) translatable through a longitudinal anvil slot (1362) of anvil (1358) and a vertical slot (1364) of staple cartridge (1356). Firing beam (1360) includes a knife configured to sever tissue.

FIG. 24 shows a sectional end view of a portion of end effector (1350) of FIG. 23 with first and second jaws (1352, 1354) in an open position and an exemplary pair of buttress assemblies (1366, 1368) (each also referred to individually as a "buttress") applied to first and second jaws (1352, 1354) of end effector (1350). Buttress assembly (1366) may include an adhesive layer to adhere with an underside (1370) of anvil (1358) and/or buttress assembly (1368) may include an adhesive layer to adhere with an upper deck (1372) of staple cartridge (1356). Each staple (1374) is driven from staple cartridge (1356) by a staple driver (43) through a corresponding staple aperture (1376) into forming contact with a staple forming pocket (1378). Exemplary buttress assemblies, exemplary materials and techniques for applying buttress assemblies, and exemplary buttress applier cartridges may be configured in accordance with at least some of the teachings of U.S. Pat. No. 10,349,939, entitled "Method of Applying a Buttress to a Surgical Stapler," issued Jul. 16, 2019, and U.S. patent application Ser. No. 17/022,520, entitled "Method of Applying Buttress to End Effector of Surgical Stapler," filed on Sep. 16, 2020, issued as U.S. Pat. No. 11,660,093 on May 30, 2023, the disclosures of which are incorporated by reference herein.

J. Exemplary Method of Operating Surgical Instrument

Figure 25:
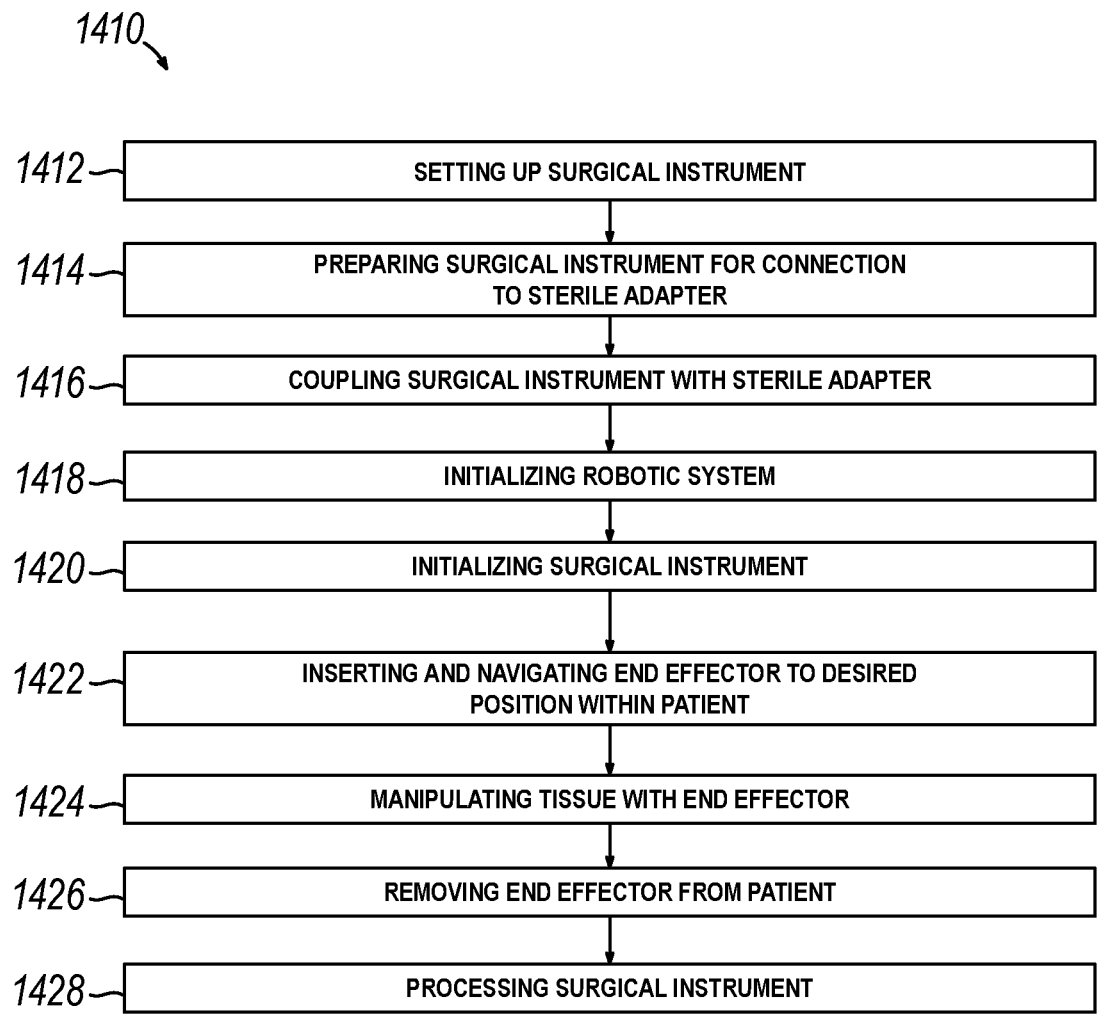
FIG. 25 depicts an exemplary method of using the surgical instrument of FIG. 9 with the end effector of FIG. 23.
Figure 26A:
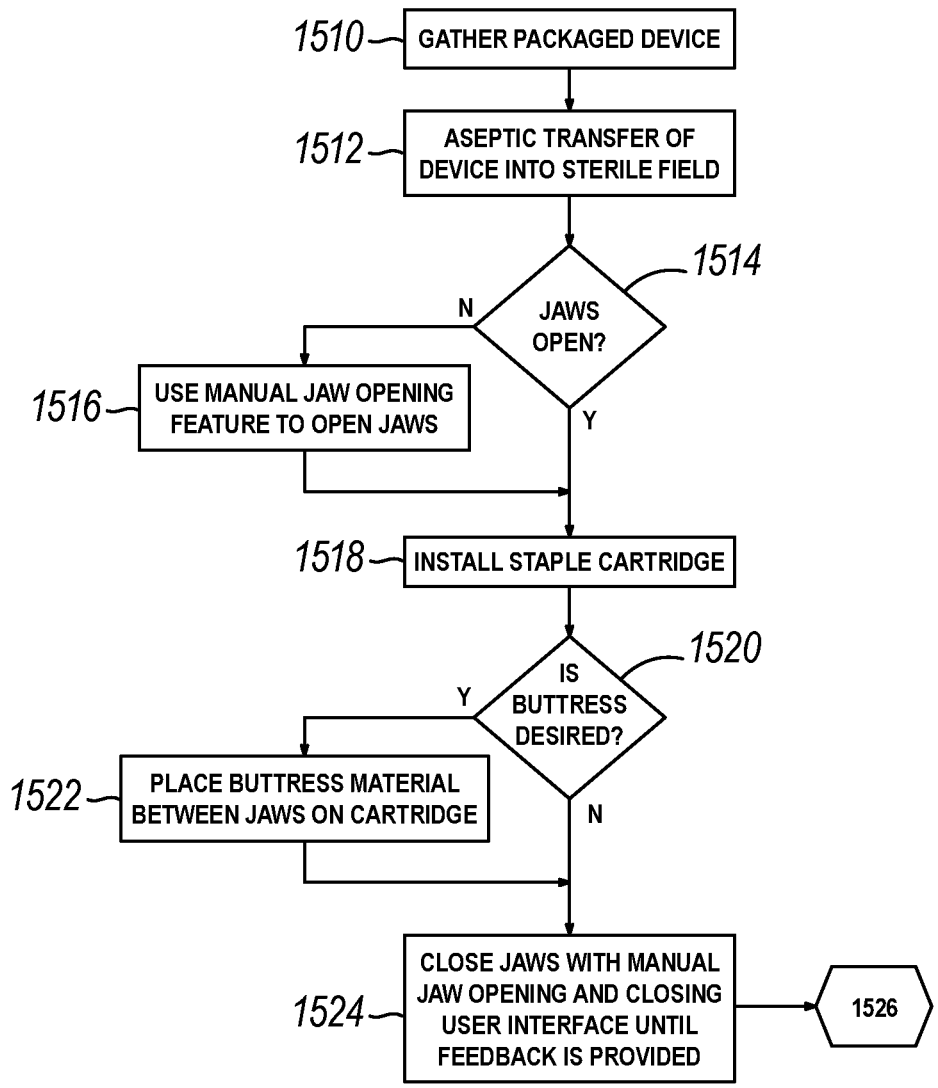
FIG. 26A depicts a flowchart of a first aspect of an exemplary method of operating the surgical instrument of FIG. 9 with the end effector of FIG. 23.
Figure 26B:
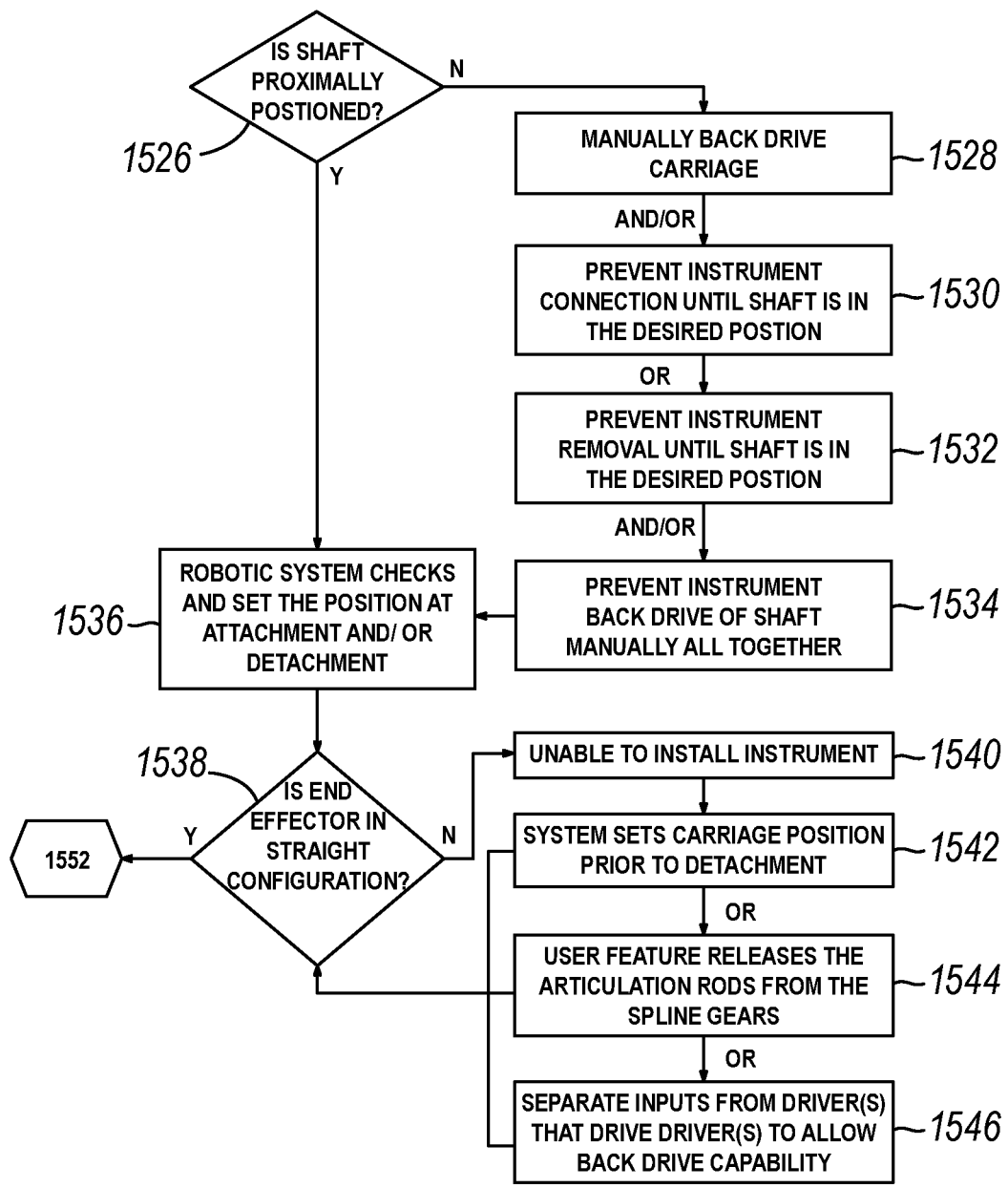
FIG. 26B depicts a flowchart of a second aspect of the method of operating the surgical instrument of FIG. 9 with the end effector of FIG. 23.
Figure 26C:
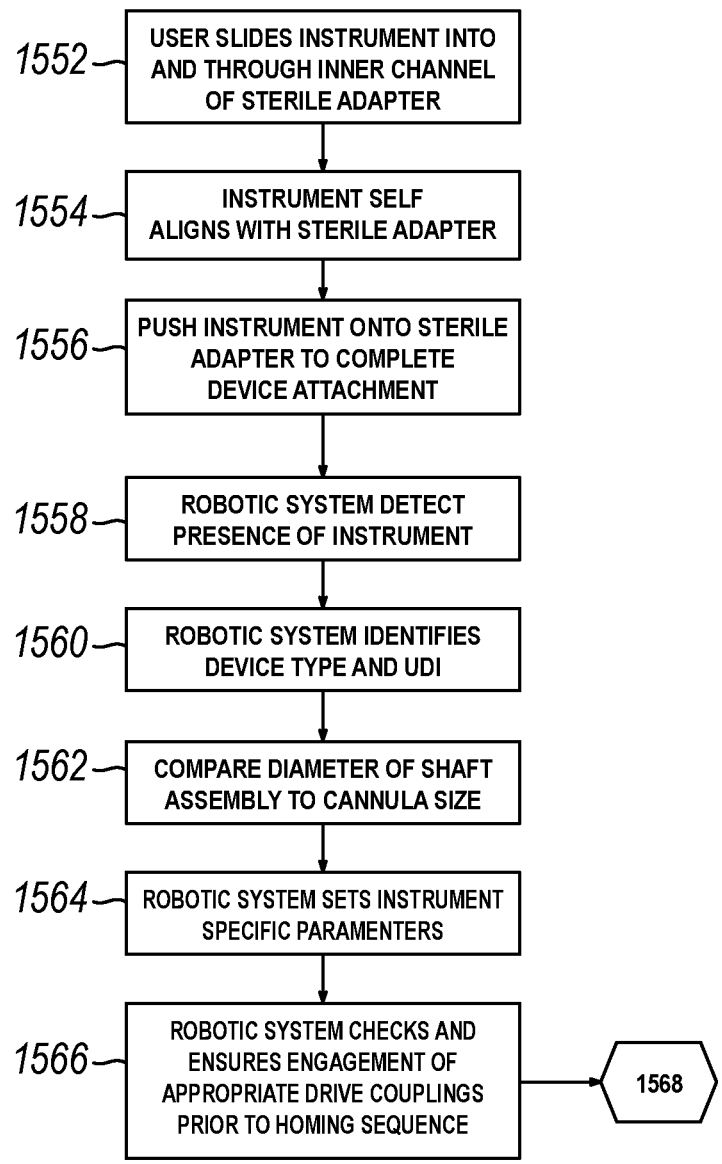
FIG. 26C depicts a flowchart of a third aspect of the method of operating the surgical instrument of FIG. 9 with the end effector of FIG. 23.
Figure 26D:
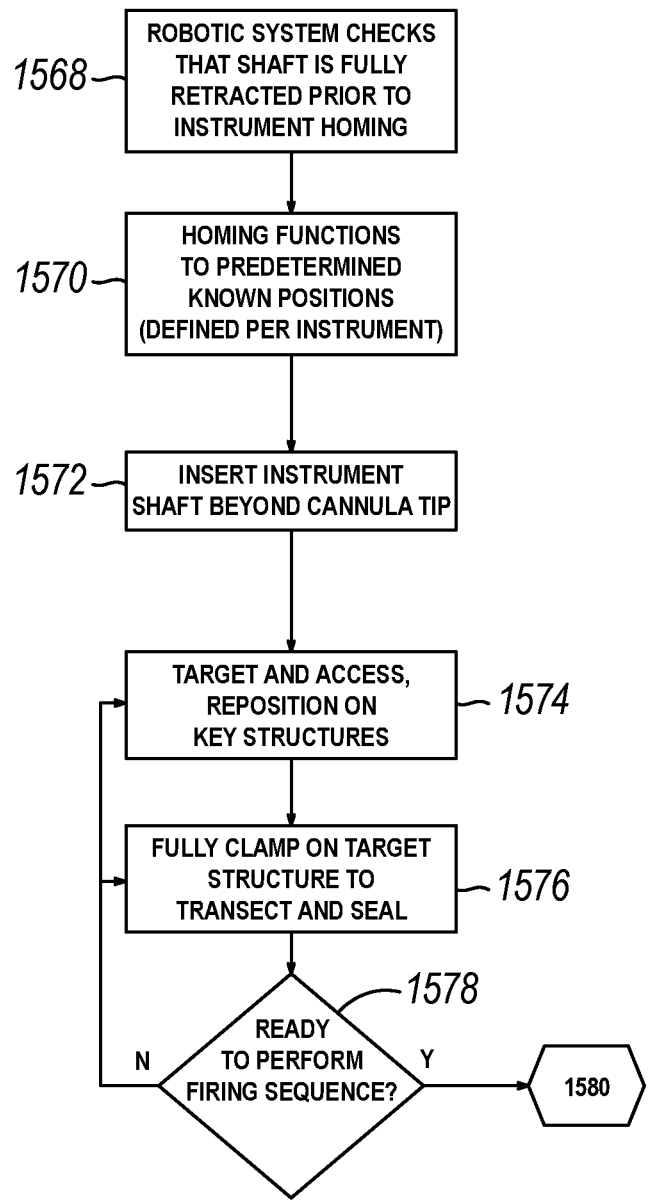
FIG. 26D depicts a flowchart of a fourth aspect of the method of operating the surgical instrument of FIG. 9 with the end effector of FIG. 23.
Figure 26E:
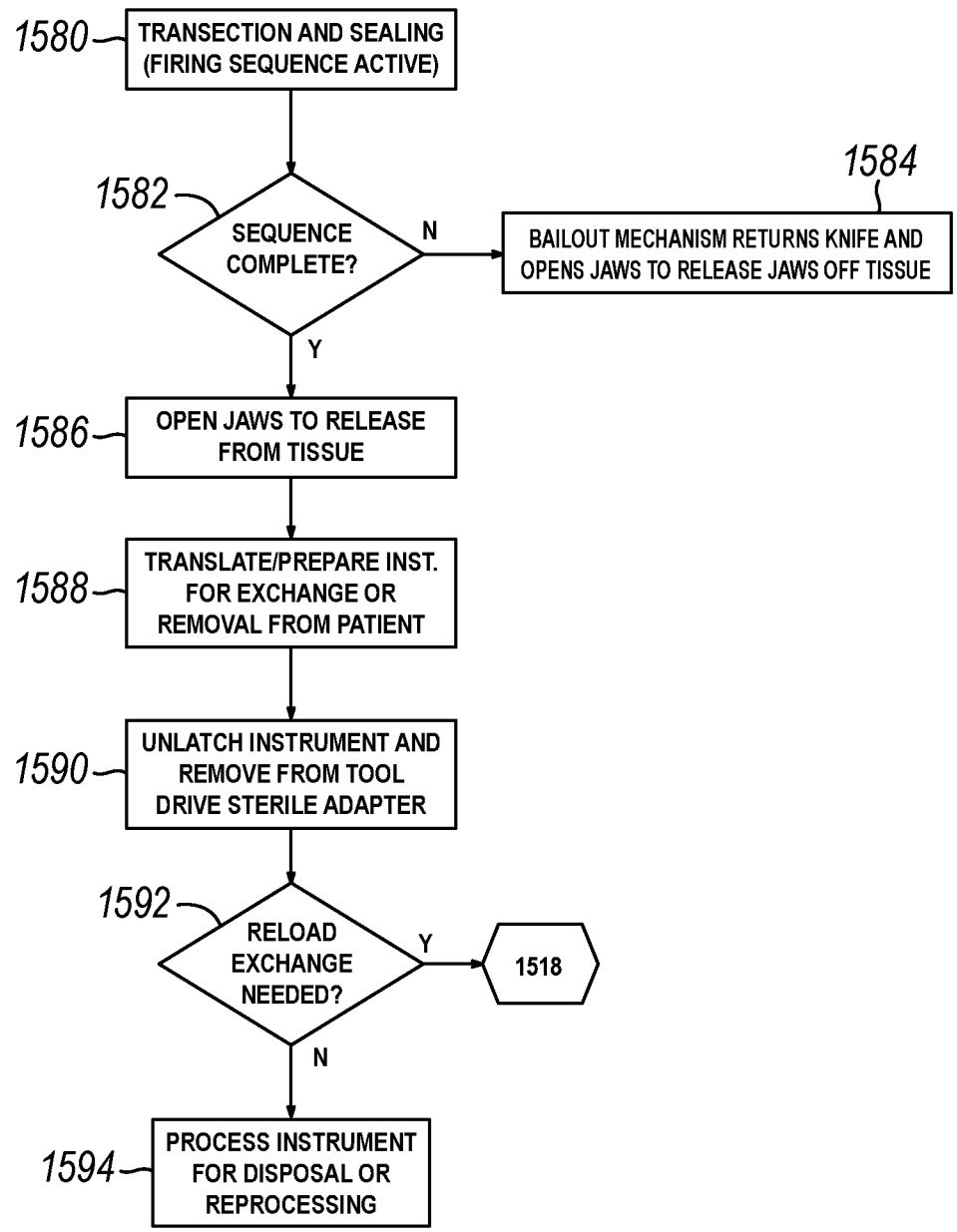
FIG. 26E depicts a flowchart of a fifth aspect of the method of operating the surgical instrument of FIG. 9 with the end effector of FIG. 23.

An exemplary method (1410) of using robotic systems (10, 28) is described below with reference to FIGS. 25-26E. FIG. 25 shows an overview of method (1410), while FIGS. 26A-26E provides additional detail as to individual substeps of method (1410). While certain steps of method (1410) are described with reference to first and second jaws (1352, 1354) of end effector (1350), which includes anvil (1358) and staple cartridge (1356), it is also envisioned that first and second jaws (1086, 1088) of end effector (1016) with clamp arm (1090) and ultrasonic blade (1092) or end effector (116) with clamp arm (144) and ultrasonic blade (146) may be alternatively utilized. As will be described in greater detail below, when utilizing end effector (1350), different steps may be performed as compared to utilizing end effector (116, 1016) with clamp arm (1090) and ultrasonic blade (1092). Various other end effectors are also envisioned including, but not limited to, end effectors that apply radiofrequency energy, end effectors that biopsy tissue, and end effectors that suction fluid and irrigate tissue.

At step (1412), method (1410) includes setting up surgical instrument (1010). At step (1414), method (1410) includes preparing surgical instrument (1010) for connection with a sterile adapter, such as sterile adapter (1040) shown in FIG. 9. At step (1416), method (1410) includes coupling surgical instrument (1010) with sterile adapter (1040). At step (1418), method (1410) includes initializing robotic system (10, 28). As previously described, robotic system (10, 28) includes patient support (e.g., table (16) in FIG. 1 and table (34) in FIG. 2), one or more robotic arms (32), and surgical instrument (1010). At step (1420), method (1410) includes initializing surgical instrument (1010), which may be performed when sterile adapter (1040) is coupled with robotic system (10, 28). At step (1422), method (1410) includes inserting and navigating end effector (116, 1016, 1350) to the desired position within the patient. At step (1424), method (1410) includes actively manipulating tissue with end effector (116, 1016, 1350) of surgical instrument (1010). At step (1426), method (1410) includes removing end effector (116, 1016, 1350) of surgical instrument (1010) from the patient. At step (1428), method (1410) includes processing surgical instrument (1010) after removing end effector (116, 1016, 1350) of surgical instrument (1010) from the patient. Processing surgical instrument (1010) may include preparing end effector (116, 1016, 1350) for reinsertion into the patient or disposing of end effector (116, 1016, 1350) as desired.

Method (1410) of using robotic systems (10, 28) is described in greater detail with reference to with reference to FIGS. 26A-26E. Step (1412) of setting up surgical instrument (1010) may include steps (1510, 1512, 1514, 1516, 1518, 1520, 1522, 1524). At step (1510), method (1410) includes gathering the sterile package containing surgical instrument (1010). The sterile package may contain information identifying surgical instrument (1010) to help the user to easily identify and even track surgical instrument (1010). At step (1512), surgical instrument (1010) is aseptically transferred into the sterile field. At step (1514), method (1410) includes ensuring that first and second jaws (1086, 1088, 1352, 1354) are in an open position. This open position may be similar to the open position shown in FIG. 23A regarding end effector (1350). The open position is also shown in FIG. 7B regarding end effector (116) and in FIG. 13 regarding end effector (1016). If first and second jaws (1086, 1088, 1352, 1354) are not in the open configuration, at step (1516) the user may manipulate a manual jaw actuation mechanism to mechanically open first and second jaws (1086, 1088, 1352, 1354). One such suitable manual jaw actuation mechanism (1316) is shown and described above with reference to FIGS. 21-22 with reference to surgical instrument (1310), which may be similar to surgical instrument (1010).

At step (1518), the user may insert staple cartridge (1356) into one of first or second jaws (1352, 1354) of end effector (1350). When first and second jaws (1352, 1354) are in the open configuration, the user may proceed to step (1520) and determine whether one or more buttress assemblies (1366, 1368) is desired. At step (1522) if one or more buttress assemblies (1366, 1368) are desired, the user may place buttress assemblies (1366, 1368) between first and/or second jaws (1352, 1354) of staple cartridge (1356). As previously described, buttress assemblies (1366, 1368) may include an adhesive layer to couple with first and/or second jaws (1352, 1354). Once one or more buttress assemblies (1366, 1368) have been applied or it is determined that no buttress assemblies (1366, 1368) are desired, the user may proceed to close first and second jaws (1086, 1088) with the manual jaw opening feature (not shown). Steps (1518, 1520, 1522) may be omitted for end effector (116, 1016). For example, at step (1524), the user may close the user interface until feedback is provided. This feedback may be provided in a variety of suitable manners (including one or more of an audible indication, a tactile indication, a visual indication displayed on a screen, etc.).

Step (1414) of preparing surgical instrument (1010) for connection with sterile adapter (1040) may include steps (1526, 1528, 1530, 1532, 1534, 1536, 1538, 1540, 1542, 1544, 1546). Once first and second jaws (1086, 1088, 1352, 1354) are closed in a closed position, the user may proceed to step (1526). At step (1526), the user may ensure that shaft assembly (1018) is located in the proximal position (see FIG. 11A). If shaft assembly (1018) is not located in the proximal position, at step (1528), carriage (1030) may be manually back-driven proximally along longitudinal axis (LA) to the proximal position. If surgical instrument (1010) has the mechanical advantage to manually back-drive carriage (1030) in the proximal direction to the proximal position, the user may actuate that user interface/mechanism. For example, one such suitable user interface/mechanism may be back-driving threaded lead screw (1132) having a suitable thread pitch to back-drive carriage (1030). More specifically, actuating translation driver (1026) may include rotating threaded lead screw (1132) in a first rotational direction relative to threaded receiver (1134) to translate carriage (1030) proximally along threaded lead screw (1132). Such back-driving may be obtained by actuating drive output (68) of robotic arm (32) to transmit a rotational force to sterile adapter (1040) to transmit the rotary motion to first rotational drive input (1038a). First rotational drive input (1038a) then transmits the rotary motion to translation driver (1026), which then transmits the rotary motion to threaded receiver (1134) which includes internal threads (1136) (see FIG. 18). Since threaded receiver (1134) is rotatably coupled with proximal carriage frame member (1120) and distal frame attachment member (1138) is translatably coupled with proximal carriage frame member (1120), carriage (1030) may move proximally, which moves shaft assembly (1018) and end effector (1016) proximally.

Alternatively, if there is insufficient mechanical advantage (e.g., the thread pitch is not high enough to enable back driving), then it may be desirable to release threaded receiver (1134) from translation driver (1026). In some versions, this decoupling may be manually performed. Instead of or in addition to carriage (1030) being manually back-driven at step (1528) to the proximal position, at step (1530) surgical instrument (1010) may be prevented from connecting with robotic system (10, 28) until shaft assembly (1018) is in the desired position. Instead of or in addition to carriage (1030) being manually back-driven at step (1528) to the proximal position, at step (1532), surgical instrument (1010) may be prevented from being removed from robotic system (10, 28) until shaft assembly (1018) is in the desired position. This may include a physical lockout mechanism or an electronic lockout mechanism. Step (1532) may be performed together with step (1528). Instead of or in addition to performing steps (1528, 1530, 1532), at step (1534) surgical instrument (1010) may be prevented from being back-driven altogether. At step (1536), robotic system (10, 28) checks and sets the position at attachment and/or detachment. Once the robotic system (10, 28) checks and sets the position at attachment and/or detachment, the user or robotic system (10, 28) may proceed to step (1538).

At step (1538), the user or robotic system (10, 28) may determine whether end effector (1350) is in the straight configuration, similar to the positioning of shaft assembly (114) shown in FIG. 7A. If end effector (1350) is not disposed in the straight configuration, the user may be unable to install surgical instrument (1010) with robotic system (10, 28) as shown in step (1540). If unable to install surgical instrument (1010), robotic system (10, 28) may set the position of carriage (1030) prior to detachment at step (1542). Instead of performing step (1542), a user feature may release actuation driver (1028) from first spur gear (1154), which includes internal aperture (1160) containing a complementary spline pattern to effectively decouple actuation driver (1028) from actuation assembly (1032). Instead of performing steps (1542, 1544), robotic system (10, 28) may decouple first rotational drive input (1038*a*) from translation driver (1026) and/or decouple second rotational drive input (1038*b*) from actuation driver (1028) at step (1546). Decoupling first rotational drive input (1038*a*) from translation driver (1026) may prevent certain translational movement of end effector (1016), shaft assembly (1018), and carriage (1030). Decoupling second rotational drive input (1038*b*) from actuation driver (1028) may prevent actuation of first and second jaws (1086, 1088, 1352, 1354) of end effector (1350). After performing at least one of steps (1542, 1544, 1546), robotic system (10, 28) may again determine whether end effector (1350) is in the straight configuration at step (1538) or move to step (1552) without again determining whether end effector (1350) is in the straight configuration.

Step (1416) of coupling surgical instrument (1010) with sterile adapter (1040) may include steps (1552, 1554, 1556). At step (1552), the user may move (e.g., slide) surgical instrument (1010) into and through at least a portion of inner channel (1042) of sterile adapter (1040) (shown schematically in FIG. 9). The dimensions of inner channel (1042) of sterile adapter (1040) accommodate the outer diameter of outer shaft (1060) of shaft assembly (1018) and the outer diameter of guide shaft (1046). At step (1554), surgical instrument (1010) may self-align with sterile adapter (1040). For example, aligning feature (1044) on guide shaft (1046) may couple with aligning feature (1048) of sterile adapter (1040). It is envisioned that aligning features (1044, 1048) may be self-aligning features. At step (1556), surgical instrument (1010) may be guided into engagement with sterile adapter (1040) to complete the attachment of sterile adapter (1040) with surgical instrument (1010). A latch (not shown) of surgical instrument (1010) may be actuated to secure surgical instrument (1010) with sterile adapter (1040) in the locked position. In other words, attachment interface (1012) of surgical instrument (1010) is configured to couple with sterile adapter (1040), such that attachment interface (1012) is operatively coupled with robotic arm (32). Once surgical instrument (1010) is selectively coupled with sterile adapter (1040), the user may receive feedback (e.g., visual feedback, audible feedback, or other suitable feedback). If surgical instrument (1010) is insufficiently coupled, the user may also receive feedback.

Step (1418) of initializing robotic system (10, 28) may include steps (1558, 1560, 1562, 1564, 1566). At step (1558), robotic system (10, 28) detects the presence of surgical instrument (1010). Step (1558) may include operatively coupling surgical instrument (1010) with robotic arm (32) using sterile adapter (1040). For example, robotic system (10, 28) may include one or more proximity sensors or switches that both determine proximity of surgical instrument (1010) relative to robotic system (10, 28) and a whether surgical instrument (1010) is completely coupled with robotic system (10, 28). At step (1560), robotic system (10, 28) may automatically determine the type of surgical instrument (1010) inserted and/or the actual surgical device (e.g., using a unique device identification (UDI) system). This identification of surgical instrument (1010) may include wireless identification and/or physical identification. For example, wireless identification may include using radiofrequency (RF) and/or near-field communication (NFC). Physical identification may include a physical connection, such as a plug or pogo pin contacts etc. Other suitable wireless identification and physical identification structures are also envisioned. Identification may trigger the recall of positional parameters from a previously exchanged surgical instrument (1010). For example, if end effector (1350) is removed to exchange a spent staple cartridge (1356) with a new staple cartridge (1356), then surgical instrument (1010) is again operatively coupled with robotic arm (32), robotic system (10, 28) may recall the previous insertion position. This may assist the user with accurate and timely repositioning of end effector (1350) for exchange of staple cartridge (1356) or for other reasons. At step (1560), surgical instrument (1010) may be confirmed or rejected by robotic system (10, 28).

At step (1562), the diameter of shaft assembly (1018) and diameter of the cannula (not shown) may be compared. For example, if a smaller sized surgical instrument (1010) is compared with a larger sized cannula of a trocar, a recommendation may be prompted for the user to use the appropriate sized cannula of a trocar or insert of a reducer between the cannula and surgical instrument (1010). One such suitable trocar that includes a cannula is shown and described in U.S. App. Ser. No. 63/018,555, entitled "Latchless Obturator with Interference Fit Feature" filed on May 1, 2020, the disclosure of which is incorporated by reference herein. At step (1564), robotic system (10, 28) sets specific parameters that may be specific to surgical instrument (1010). Data may reside in surgical instrument (1010) and be uploaded to a cloud or other data storage system or the data may reside on robotic system (10, 28) in a lookup table. For example, the teachings disclosed herein may be combined with any of the teachings of U.S. Pub. No. 2019/0201136, entitled "Method of Hub Communication," published Jul. 4, 2019, issued as U.S. Pat. No. 11,659,023 on May 23, 2023; U.S. Pub. No. 2019/0206569, entitled "Method of Cloud Based Data Analytics for Use with the Hub," published Jul. 4, 2019; U.S. Pub. No. 2020/0100830, entitled "Method for Constructing and Using a Modular Energy System with Multiple Devices," published Apr. 2, 2020 issued as U.S. Pat. No. 11,666,368 on Jun. 6, 2023; and U.S. Prov. Pat. App. No. 63/018,664, entitled "Stabilizer for Surgical Shafts or Cannulas," filed on May 1, 2020, the disclosures of which are incorporated by reference herein.

At step (1566), robotic system (10, 28) may perform a check to ensure engagement of all appropriate drive couplings prior to commencing a homing sequence. For example, this may include aligning drive outputs (68) with sterile adapter (1040). Robotic system (10, 28) may rotate drive inputs in a clockwise or counter clockwise direction until hard stop(s) are detected via a sensor (e.g., a torque sensor or a current sensor) which indicate surgical instrument (1010) and robotic system (10, 28) have established drive engagement. In some versions, translation driver (1026) and/or actuation driver (1028) may be actuated to ensure the expected translation and actuation of end effector (1016, 1350) while surgical instrument (1010) remains outside of the patient. Sequence of coupling turns clockwise or counterclockwise is based instrument type to ensure proper engagement. This may include using hard stops, current threshold, or using other suitable structures.

Step (1420) of initializing surgical instrument (1010) may include steps (1568, 1570). For example, in step (1568), robotic system (10, 28) checks that shaft assembly (1018) is fully retracted prior to homing of surgical instrument (1010). Positional sensing of shaft assembly (1018) may be determined using one or more of proximity sensors, switches, current limits between surgical instrument (1010) and robotic arm (32) to detect the position of shaft assembly (1018). This may be performed during the drive coupling check step (1566). At step (1570), functions are homed to known set positions on a per surgical instrument basis. This may include when end effector (1350) of surgical instrument (1010) is within the cannula of the trocar by manipulating end effector (1016) by tapping on cannula inner diameter sensing hard stops, using current thresholds, or loading to set a known home position for the selected function of surgical instrument (1010).

Step (1422) of inserting and navigating end effector (1016) to the desired position within the patient may include steps (1572, 1574, 1576, 1578). Step (1572) includes inserting shaft assembly (1018) beyond the distal most tip of the cannula. For example, actuating translation driver (1026) may include rotating threaded lead screw (1132) in a second rotational direction relative to threaded receiver (1134) to translate carriage (1030), shaft assembly (1018), and end effector (1350) distally along a predetermined distance of threaded lead screw (1132). First and second jaws (1086, 1088, 1352, 1354) are in the closed position, and not in teleoperation mode, until an articulation joint (e.g., articulation section (164)) of end effector (1350) is beyond the cannula tip of the trocar. Wristed joint motion is locked until articulation section (164) is disposed beyond the cannula tip. Firing of surgical instrument (1010) may remain locked and inactive until surgical instrument (1010) is fully clamped. Activate teleoperation to open first and second jaws (1086, 1088, 1352, 1354) to the open position then fully close the trigger again.

At step (1574), end effector (1016) targets and accesses target structures. Jaw grasping and closure is in the active state. Wristed motion of end effector (1016) and translation are in the active state. Regarding surgical instrument (1010) including end effector (1016), translation driver (1026) may be actuated to translate carriage (1030) and ultrasonic transducer assembly (1022) along longitudinal axis (LA) so that ultrasonic transducer assembly (1022) moves from the proximal position along longitudinal axis (LA) to distal position along longitudinal axis (LA). Exemplary wristed motion is shown in FIGS. 8A-8B regarding end effector (116). At step (1576), end effector (1016, 1350) fully clamps onto target structure to transect and seal target structure. Jaw grasping and closure may be in the active state. In some versions, robotic system (10, 28) may lock out wristed motions and translation. At step (1578), the user determines whether to perform the firing sequence. If not, steps (1574) and (1576) may be performed one or more times, until the user is ready to perform the firing sequence. If ready to perform the firing sequence, the method proceeds to step (1580) of tissue transection and sealing.

Step (1424) of manipulating tissue with end effector (1016) of surgical instrument (1010) includes steps (1580, 1582, 1584, 1586, 1588). During step (1580), at least one of first and second jaws (1086, 1088, 1352, 1354) is configured to pivot relative to the other of first and second jaws (1086, 1088, 1352, 1354) to compress tissue therebetween. Firing lockout assembly of surgical instrument (1010) may be unlocked, enabling surgical instrument firing. Additionally, jaw grasping and closure may be in active or inactive state. Additionally, wristed motion of end effector (1016) and translation may be in the inactive state. Exemplary wristed motion is shown in FIGS. 8A-8B regarding end effector (116). Regarding end effector (1016), actuation driver (1028) is actuated to translate a portion of shaft assembly (1018) thereby causing clamp arm (1090) to pivot relative to ultrasonic blade (1092). Translating member (1158) may be translated a predetermined distance (D) to translate outer shaft (1060) along the longitudinal axis, such that outer shaft (1060) applies a predetermined closure force to compress the tissue between first and second jaws (1086, 1088, 1352, 1354). The closure force may be linear or non-linear. For example, surgical instrument (1010) may include closure force adjusting mechanism (1180), which may include wave spring (1188) to adjust the closure force as described in greater detail with reference to FIGS. 29A-32. Additionally, the motor may be adjusted as shown in FIG. 33 to apply different closing speeds to the tissue.

At step (1582), the user determines whether the firing sequence is complete. If the firing sequence is not complete, at step (1584) a bailout mechanism may return knife (e.g., a distal portion of firing beam (1360) of FIG. 23) and open first and second jaws (1352, 1354) to release first and second jaws (1352, 1354) from the tissue. If the sequence is complete, method (1410) proceeds to step (1586) regarding opening first and second jaws (1086, 1088, 1352, 1354) to release first and second jaws (1086, 1088, 1352, 1354) from the tissue. One such suitable bailout mechanism is manual jaw actuation mechanism (1316). At step (1586), jaw grasping and closure is in the active state. Additionally, wristed motion of end effector (1350) and translation is in the active state. In some versions, firing of surgical instrument (1010) is locked and remains inactive until exchange of surgical instrument (1010) is performed (with spent staple cartridge disposed within first and second jaws (1352, 1354) regarding end effector (1350)).

Step (1426) of removing end effector (1016) of surgical instrument (1010) from the patient may include step (1588). Step (1588) may commence once the tissue is released from first and second jaws (1086, 1088) as indicated in step (1586). In step (1588), surgical instrument (1010) is removed from the patient. For example, using actuation driver (1028), end effector (1016) may be translated away from the patient as described above. Regarding surgical instrument (1010) including end effector (1016), translation driver (1026) may be actuated to translate carriage (1030) and ultrasonic transducer assembly (1022) along longitudinal axis (LA) so that ultrasonic transducer assembly (1022) moves from the current distal position along longitudinal axis (LA) to the desired proximal position along longitudinal axis (LA).

Wristed motion of end effector (1350) and translation are in the active state. Exemplary wristed motion is shown in FIGS. 8A-8B regarding end effector (116). As an articulation joint (not shown) of end effector (1016) approaches a cannula tip of cannula (not shown), an articulation section, similar to articulation section (164) may be moved to the designated home position. The designated home position may be zero degrees as shown in FIGS. 7A-7B regarding end effector (116) or another suitable angle. This homing may be performed automatically or manually by the user. In step (1588), firing of surgical instrument (1010) may be locked out using a lockout assembly and remain inactive until exchange of surgical instrument (1010) is performed (with spent staple cartridge (1356) disposed within first and second jaws (1352, 1354)).

Step (1428) of processing surgical instrument (1010) may include steps (1590, 1592, 1594). At step (1590), surgical instrument (1010) may be unlocked and decoupled from sterile adapter (1040). For example, there may be a user feature on surgical instrument (1010) and/or tool drive that user interacts with to unlatch surgical instrument (1010) for subsequent removal. Once surgical instrument (1010) is removed from sterile adapter (1040), at step (1592), the user determines whether another staple cartridge (1356) is desired. If no additional staple cartridge (1356) is desired, method (1410) proceeds to step (1594) where surgical instrument (1010) is processed for disposal or reprocessing. If an additional staple cartridge (1356) is desired, method (1410) proceeds to step (1518) of installing new staple cartridge (1356) into end effector (1350) of surgical instrument (1010) and continuing method (1410) from there.

III. POSITION CONTROLLED JAW CLOSURE

A. Overview

Closure force may be adjusted in a variety of manners so that at least one of first jaw (1086, 1352) or second jaw (1088, 1354) moves relative to the other of first jaw (1086, 1352) or second jaw (1088, 1354). Closure speed may also be adjusted using a similar method. Closure force may be dependent upon the motor output (e.g., motor speed) and the actuation mechanism take uses the motor output and affects movement of first and second jaws (1086, 1088, 1352, 1354). First, the output of the motor may have a constant speed and be paired with an actuation mechanism that is non-linear relative to the rotational output of the motor, such that the non-linear actuation mechanism adjusts the constant speed output of the motor causing a non-linear closure force and/or a non-linear closure speed of first jaw (1086, 1352) and second jaw (1088, 1354). One such suitable non-linear actuation mechanism may be closure force adjusting mechanism (1180) as described above, which may include wave spring (1188) according to an exemplary embodiment. However, other suitable closure force adjusting mechanisms are also envisioned. Secondly, the motor speed may be adjusted (i.e., non-linear motor speed) and be paired with a linear actuation mechanism (e.g., omitting closure force adjusting mechanism (1180)). The linear actuation mechanism directly transfers the motor speed excluding minor variations accounting for friction etc. Thirdly, the motor speed may be adjusted (i.e., non-linear motor speed) and be paired with a non-linear actuation mechanism.

Regarding handheld instruments, it may be beneficial to prevent or otherwise reduce the likelihood of a user physically squeezing too tight on a material and potentially damaging the surgical instrument. For this reason, a spring may be incorporated to act as a shock absorber to absorb excess force instead of the force being transmitted on the closure mechanisms. Since robotic instruments may be automatically driven, there may be generally less concern with exceeding an allowable closure force. However, for robotic instruments, it is beneficial to correctly size the motor relative to the desired forces experienced by the motor. For example, while "oversizing" the motor by providing a larger motor than that to obtain the desired torque profile may increase the torque of the motor, the larger motor may be heavier, bulkier and/or generate greater heat during operation. Alternatively, "undersizing" the motor by providing a smaller motor that may not provide the desired torque profile in some limited instances to fully actuate end effector (1016) when compressed against more rigid structures. As a result, it is beneficial to appropriately size the motor based on the desired torque profile. Constraints include motor speed and amount of load mechanical advantage. For example, a user may initially approach tissue at a greater speed while having less closure force and then clamp on the tissue slower but with a more significant force to effectuate the clamping.

Surgical instrument (1010) is shown as not including a closed looped feedback. This closed loop feedback may be obtained by including one or more sensors to sense tissue compression in real-time. While a force sensor operatively coupled with closure member may allow for a closure force to be determined, it may be difficult to incorporate a force sensor at the exact desired position in some examples. While including a pressure or force sensor may allow for closed loop feedback, routing a wire to the specific location may be difficult in some examples. As a result, it may be beneficial to accurately apply a predetermined closure force without the use of a force sensor using positional control of the closure. Such positional control of the closure may provide accurate control closure regardless of losses present through individual components of the closure. Additionally, position-based control may be adjusted until the desired jaw compression loads are obtained. While a correlation between motor torque and clamping force may be developed in some instances, it is difficult to drive a motor to a specific torque once factoring in operating condition variation and/or device to device variation, such as device variations associated with manufacturing tolerances. Alternatively, it may be desirable to include one or more sensors to sense tissue compression, such that surgical instrument (1010) may include one or more force and/or position sensors to produce the desired closure profile.

B. Exemplary Jaw Closure

Figure 27:
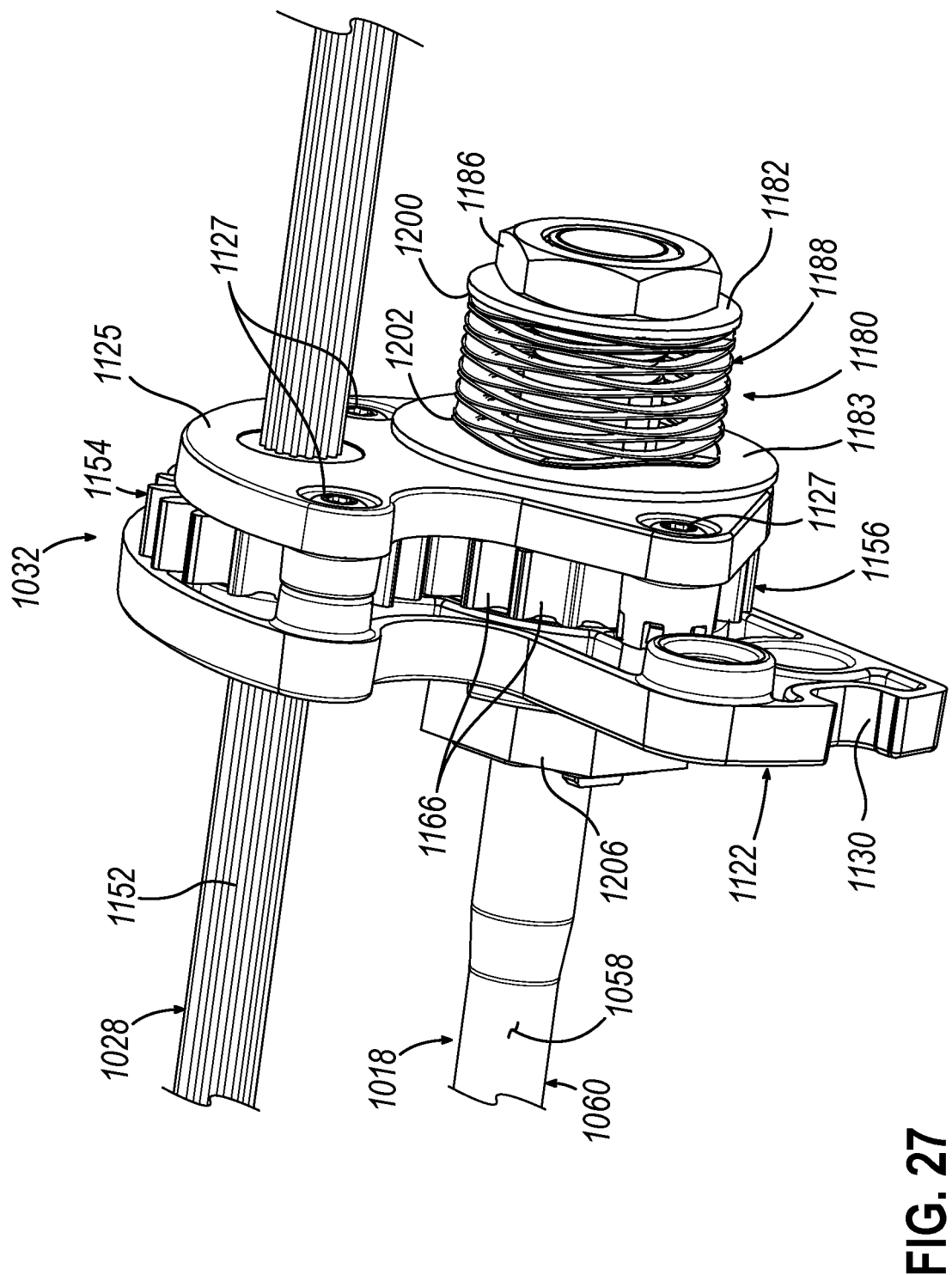
FIG. 27 depicts another perspective view of portions of the carrier and the shaft assembly similar to FIG. 20, with the carrier including the actuation assembly with the closure force adjusting mechanism.

FIG. 27 shows a perspective view of a portion of shaft assembly (1018) and a portion of carrier (1020), where carrier (1020) includes actuation assembly (1032) of FIG. 9. FIG. 28 shows an exploded perspective view of shaft assembly (1018) and carrier (1020) of FIG. 27. Robotic system (10, 28) includes a motor (shown as a portion of instrument driver (66)) configured to produce a rotational motor output. As will be described in greater detail below, instead of the motor applying a specific torque to regulate the closing speed and the closing force, one or more components (e.g., translating member 1158) may move to a predetermined known position. For surgical instrument (1010), the predetermined known position (e.g., of translating member (1158)) allows for positional based closure of first and second jaws (1086, 1088, 1352, 1354).

Attachment interface (1012) includes a first rotational drive input (1038a) configured to receive the rotational motor output of the motor. Actuation assembly (1032) may convert a single rotational input from actuation driver (1028) into a translational output to translate the closure member (e.g., outer shaft (1060)) along the longitudinal axis (LA1). More specifically, actuation driver (1028) is configured to translate the closure member along the longitudinal axis (LA1) using the rotational motor output of the motor prior to compressing the tissue between first and second jaws (1086, 1088, 1352, 1354). Translating member (1158) is configured to receive the rotational motor output and translate a predetermined distance to translate the closure member (e.g., outer shaft (1060)) along the longitudinal axis (LA1) such that the closure member applies a predetermined closure force to the tissue. Translating member (1158) and the acoustic waveguide (1066) are coaxial about the longitudinal axis (LA1).

As previously described, actuation assembly (1032) includes an optional closure force adjusting mechanism (1180) configured to selectively adjust the closure force while compressing the tissue between first and second jaws (1086, 1088, 1352, 1354). Closure force adjusting mechanism (1180) may include a resilient member (shown as wave spring (1188)) configured to adjust the closure force between first and second jaws (1086, 1088, 1352, 1354) when resilient member moves from a non-compressed state to a compressed state. In some versions, wave spring (1188) may move translating member (1158) at a constant speed as the closure force increases while compressing the tissue between first and second jaws (1086, 1088, 1352, 1354). Rotation of translating member (1158) causes compression of wave spring (1188) as will be described in greater detail with reference to FIGS. 29A-29D. While wave spring (1188) is shown as a generally linear rate spring, in some versions, wave spring (1188) may be non-uniform (e.g., a progressive rate spring or a dual rate spring) depending on the desired closure profile. While wave spring (1188) is shown and described, a variety of other suitable springs are also envisioned, including helical compression springs.

C. Closure Control Using Positional Based Closure

Figure 29A:
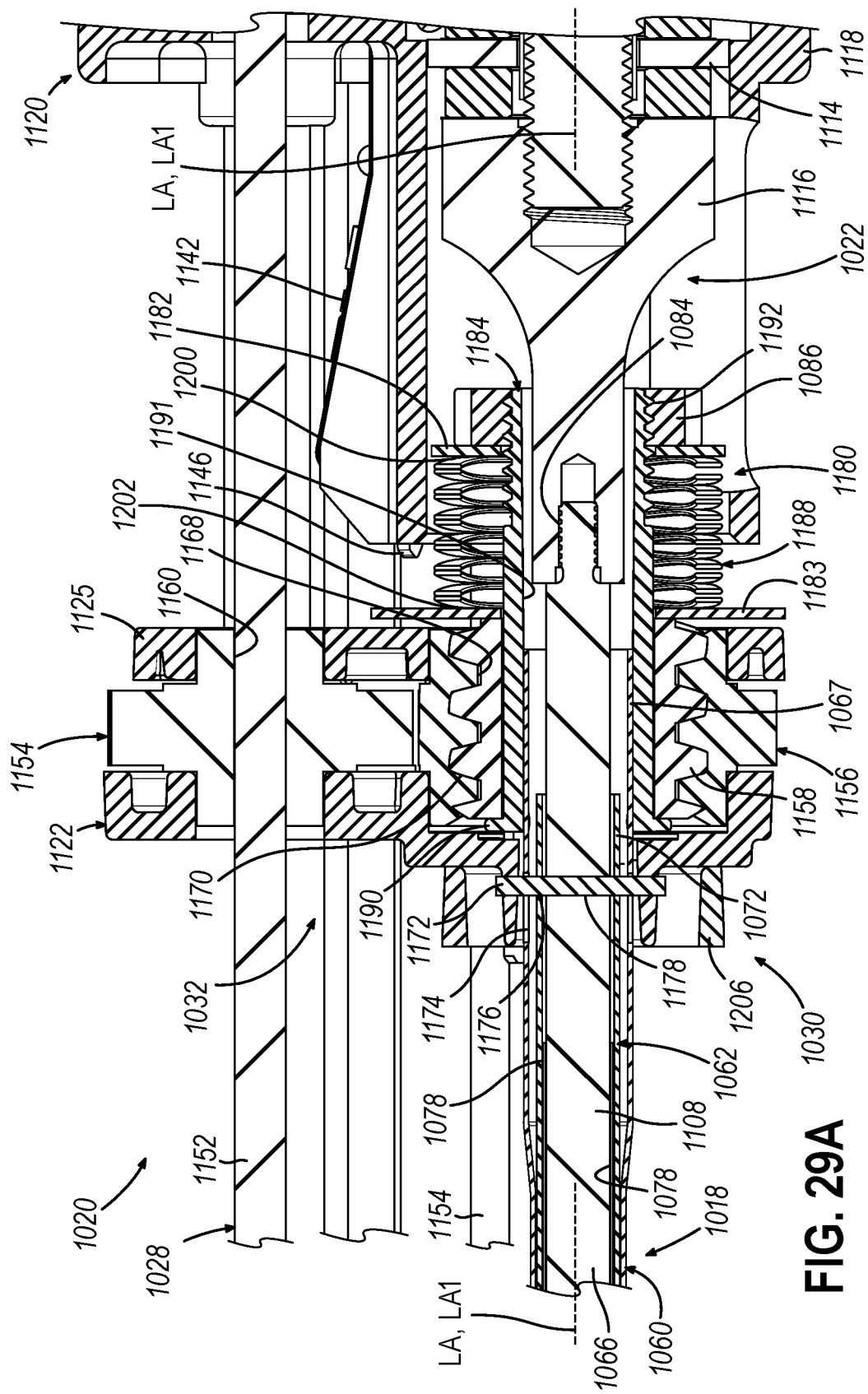
FIG. 29A depicts an enlarged cross-sectional view of the surgical instrument of FIG. 19, with the closure force adjusting mechanism in a non-compressed state and the end effector in an open position.

An exemplary positional based closure is described in greater detail with reference to FIGS. 29A-31. FIGS. 29A-29D show various states of closure for first and second jaws (1086, 1088) of surgical instrument (1010). An exemplary method (1610) of using robotic systems (10, 28) to affect closure of first jaw (1086) and second jaw (1088) of end effector (1016) is shown and described in greater detail with reference to FIGS. 30-31. More specifically, FIG. 30 shows an exemplary jaw closure routine for surgical instrument (1010) of FIG. 26A, and FIG. 31 shows a graph of exemplary plot (1652) regarding variation of the control system. As a result, FIGS. 30-31 will be described with reference to FIGS. 29A-29D regarding surgical instrument (1010). While FIGS. 29A-31 are described with reference to end effector (1016), use of other end effectors (e.g., end effectors (116, 1350)) is also envisioned. FIG. 29A shows an enlarged cross-sectional view of surgical instrument (1010) of FIG. 19, with closure force adjusting mechanism (1180) in a non-compressed state prior to end effector (1016) being actuated to clamp tissue, similar to FIG. 19. First and second jaws (1086, 1088) are in the open position (see FIGS. 13-14). In the open position, tissue is positioned between first jaw (1086) and second jaw (1088). This is also similar to FIGS. 22-23 regarding end effector (1350). In FIG. 29A, an actual distance (D) equals zero with first jaw (1086) and second jaw (1088) in the open position. As shown, flange (1190) of elongate shaft (1184) is in contact with a distal portion of elongate shaft (1184).

Figure 29B:
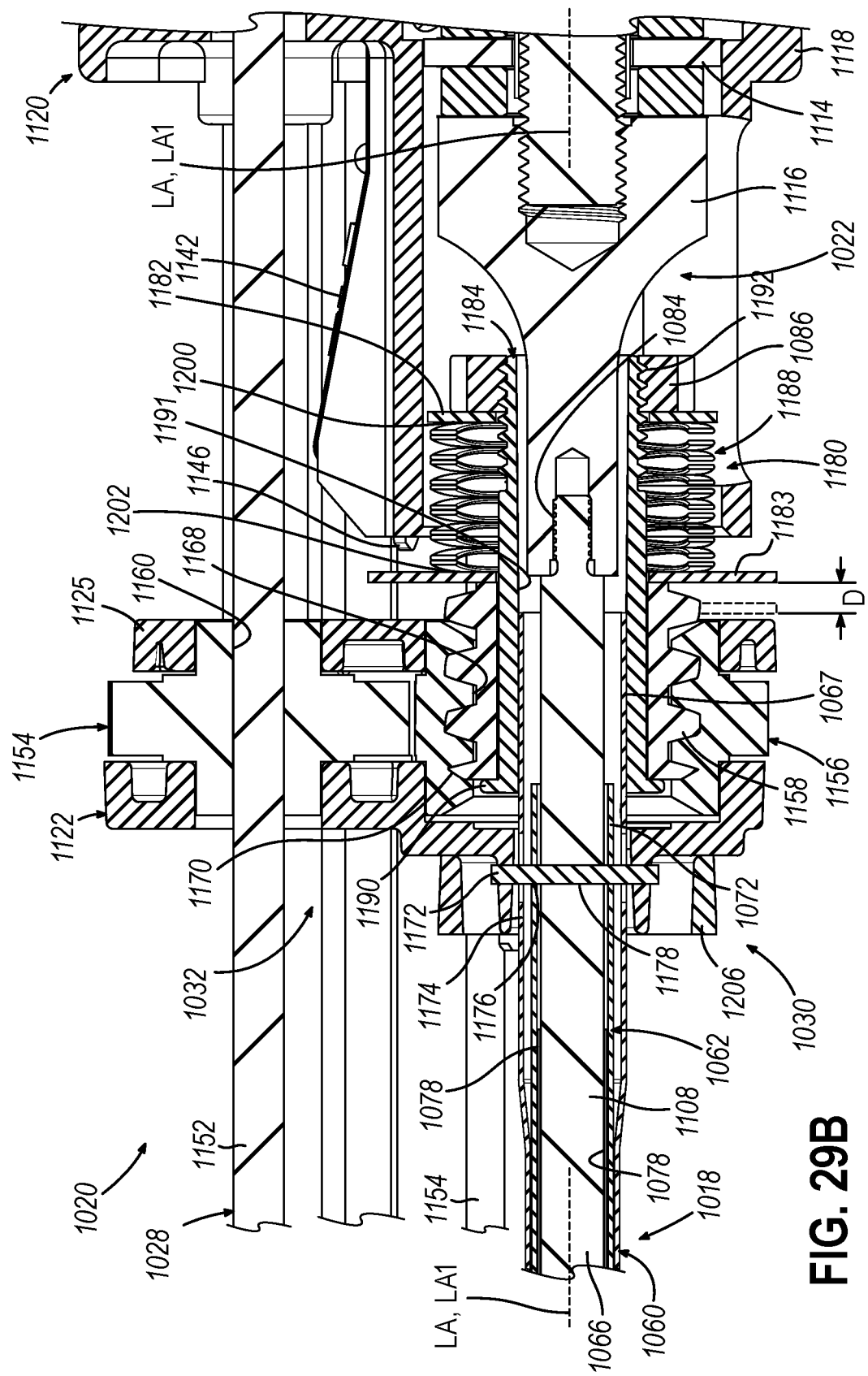
FIG. 29B depicts the enlarged cross-sectional view of surgical instrument similar to FIG. 29A with closure force adjusting mechanism in a non-compressed state prior to end effector clamping tissue, but with a translating member and a threaded member translated proximally to partially close end effector.
Figure 29C:
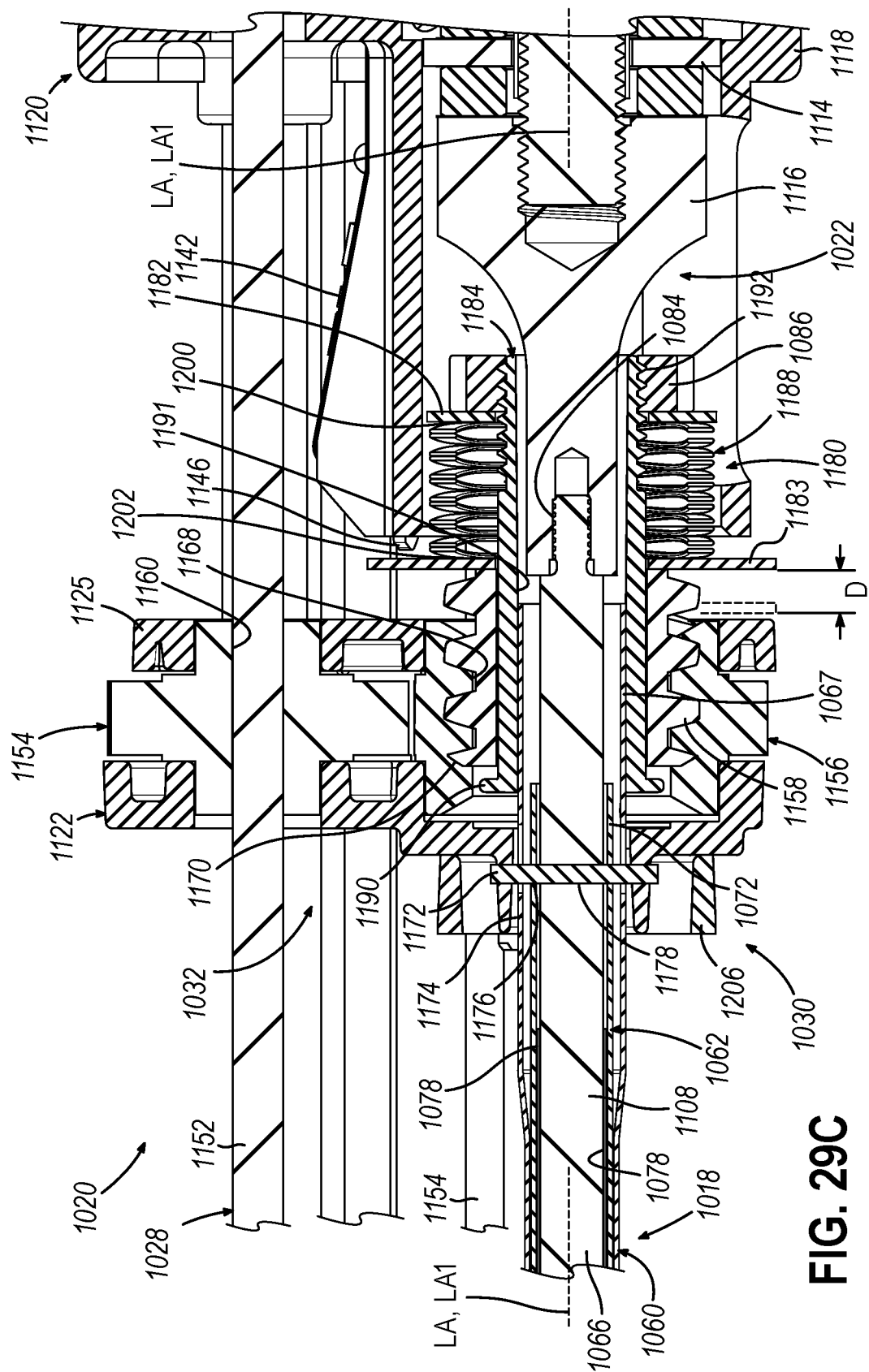
FIG. 29C depicts the enlarged cross-sectional view of surgical instrument similar to FIG. 29B, but with the translating member further proximally translated moved proximally as the closure force adjusting mechanism moves to a partially compressed state as end effector clamps tissue.
Figure 29D:
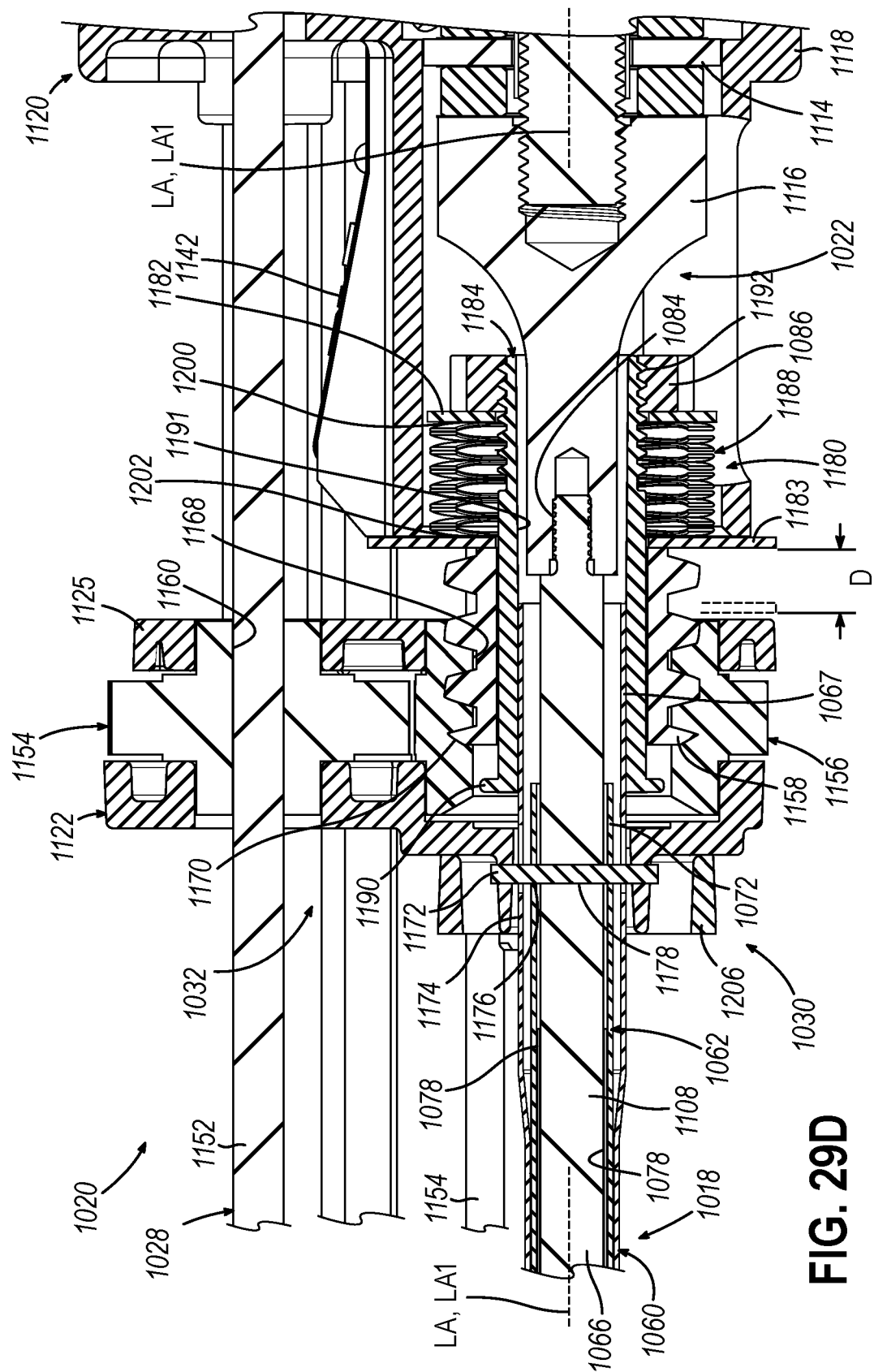
FIG. 29D depicts the enlarged cross-sectional view of surgical instrument similar to FIG. 29C, but the translating member translated further proximally and the closure force adjusting mechanism moves to a fully compressed state as end effector clamps tissue.
Figure 30:
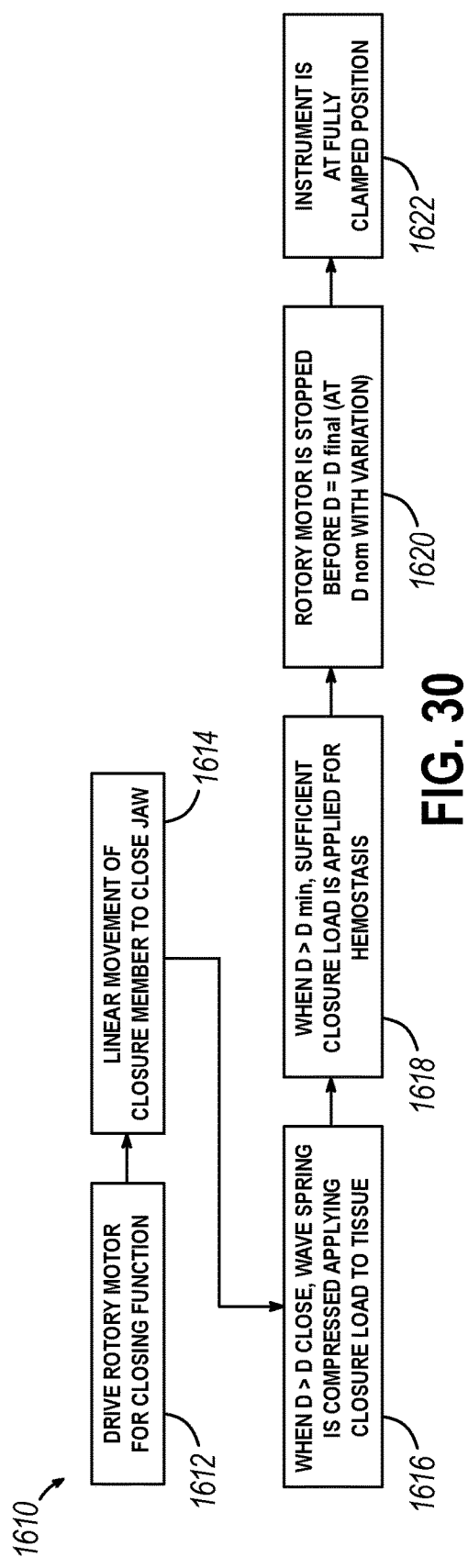
FIG. 30 depicts an exemplary jaw closure routine for surgical instrument of FIG. 27.
Figure 31:
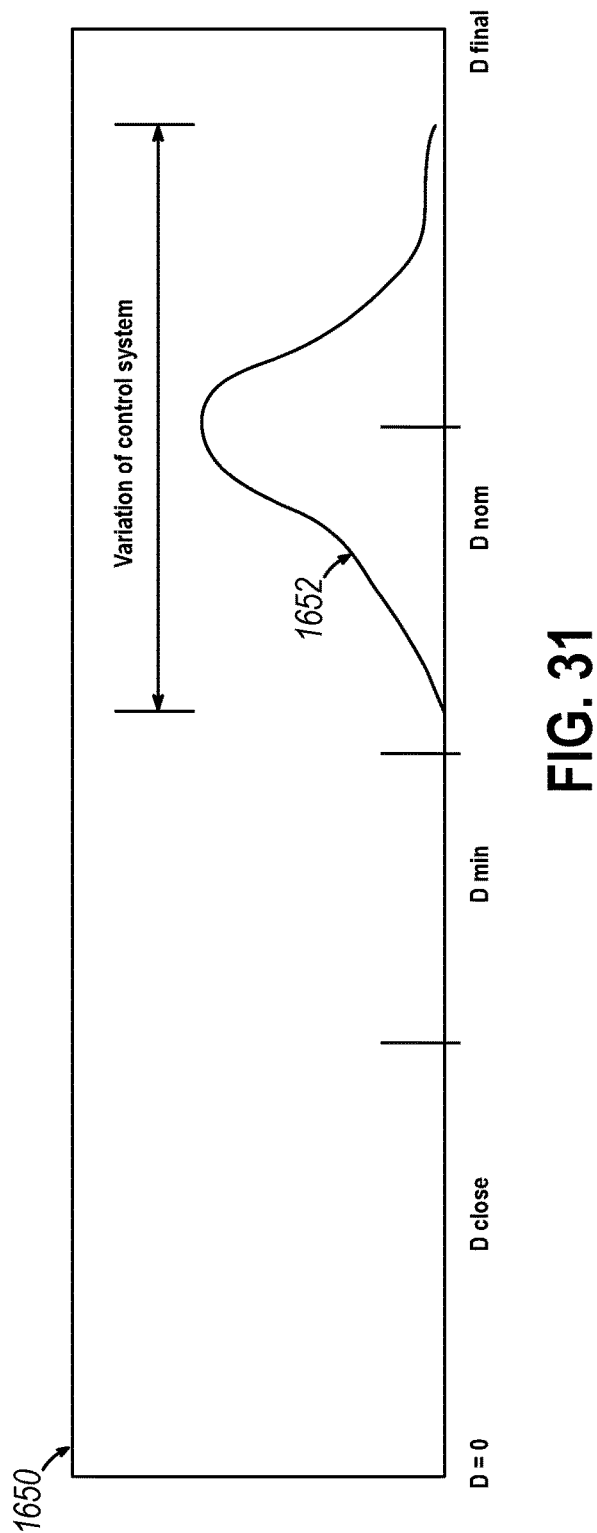
FIG. 31 depicts a graph of an exemplary plot of the closure distance of the jaw closure routine of FIG. 27.

As shown in FIGS. 30-31, at step (1612), the motor is actuated to begin closing first jaw (1086) and second jaw (1088) in the transition between FIGS. 29A-29B. The actuation of clamp arm (1090) is now described in greater detail. As shown in FIG. 9, drive output (68) of robotic arm (32) communicates rotary motion in a first direction from robotic arm (32) to sterile adapter (1040). Sterile adapter (1040) then transmits the rotary motion in the first direction to second rotational drive input (1038b). In some versions, sterile adapter (1040) may be omitted. Second rotational drive input (1038b) then transmits the rotary motion in the first direction to actuation driver (1028), which may include splined shaft (1152). As shown in FIGS. 27-29D, rotation in the first direction of splined shaft (1152) then rotates first spur gear (1154) about an axis defined by splined shaft (1152), as internal aperture (1160) of first spur gear (1154) is rotatably coupled with splined shaft (1152). Rotation of first spur gear (1154) then rotates second spur gear (1156) in an opposite direction as gear teeth (1162) of first spur gear (1154) are engaged with gear teeth (1166) of second spur gear (1156). Rotation of second spur gear (1156) translates translating member (1158) which includes external threading (1170) that is threadably engaged with internal threading (1168) of second spur gear (1156). Proximal translation of translating member (1158) causes proximal translation of outer shaft (1060), as outer shaft (1060) is translatably coupled with elongate shaft (1184). Proximal translation of outer shaft (1060) relative to inner shaft (1062) selectively pivots clamp arm (1090) toward from ultrasonic blade (1092). While not shown, proximal translation of translating member (1158) causes proximal translation of outer shaft (1060) to selectively pivot clamp arm (1090) away from ultrasonic blade (1092). Regarding end effector (1350), translating member (1158) may drive firing beam (1360) through longitudinal anvil slot (1362) of anvil (1358) and through vertical slot (1364) of staple cartridge (1356) to close first and second jaws (1352, 1354).

With reference to FIGS. 30-31, at step (1614), prior to contacting tissue, there is linear movement of outer shaft (1060) to close first and second jaws (1086, 1088). FIG. 29B shows a cross-sectional view of surgical instrument (1010) of FIG. 29A with closure force adjusting mechanism (1180) in a non-compressed state prior to end effector (1016) clamping tissue, but with translating member (1158) and elongate shaft (1184) translated proximally relative to second spur gear (1156) to partially close end effector (1016). Prior to compressing the tissue between first jaw (1086) and second jaw (1088), first and second jaws (1086, 1088) may be closed at a first closure speed that is directly proportional to the rotational motor output of the motor. In some instances, there may be some minor frictional loses due to the actuation of the various components. First jaw (1086) and second jaw (1088) may close in a linear manner, with wave spring (1188) remaining in the non-compressed state to initially not provide closure force variability (i.e., constant closure speed). Additionally, there is no return compression force exerted on first and second jaws (1086, 1088) by the tissue since the tissue is not yet being compressed. Similar to FIG. 29A, flange (1190) of elongate shaft (1184) may be in contact with a distal portion of elongate shaft (1184). As a result, wave spring (1188) remains in a non-compressed state and has a known length. The pitch of internal threading (1168) of second spur gear (1156) and external threading (1170) of translating member (1158) may be altered to change the mechanical advantage. Altering the pitch of internal and external threading (1168, 1170) affects the force to move translating member (1158) proximally and distally.

When clamp arm (1090) is not actively contacting tissue, wave spring (1188) remains in the non-contracted state (also referred to as the extended state). As a result, translating member (1158), proximal washer (1182), wave spring (1188), distal washer (1183), tuning member (1186), and elongate shaft (1184) are each moved proximally as the spring force of wave spring (1188) exceeds the opposing tissue contact force prior to tissue being contacted. Tuning member (1186) is configured to adjust a closure distance of translating member (1158). As a result, tuning member (1186) may tune the closure profile and may affect the spring force of wave spring (1188). While not shown, in some versions, tuning member (1186) may be adjusted to the point that the wave spring (1188) effectively is bottomed out and functionally removed from actuation assembly (1032).

With reference to FIGS. 30-31, at step (1616), when the actual distance (D) exceeds the closure distance (Dclose), wave spring (1188) compresses and applies a load to the tissue using first and second jaws (1086, 1088). FIG. 29C shows a cross-sectional view of surgical instrument (1010) of FIG. 29B with translating member (1158) proximally translated relative to second spur gear (1156), but with elongate shaft (1184) moved proximally as wave spring (1188) moves to a partially compressed state as end effector (1016) clamps tissue. As a result, elongate shaft (1184) is decoupled from the translation of translating member (1158), such that elongate shaft (1184) is indirectly coupled with the movement of wave spring (1188). Unlike FIGS. 29A-29B, flange (1190) of elongate shaft (1184) is spaced a first distance from the distal portion of elongate shaft (1184). Further proximal translation of translating member (1158) may increase the closure force, as outer shaft (1060) is coupled with elongate shaft (1184). As second rotational drive input (1038b) continues to rotate splined shaft (1152), affecting first spur gear (1154) and second spur gear (1156), proximal and distal washers (1182, 1183) compress wave spring (1188) which is prevented from proximal travel using tuning member (1186). Once first and second jaws (1086, 1088) compress the tissue, the closure profile may enter a non-linear stage as wave spring (1188) changes length (shortens from the fixed length of FIGS. 29A-29B) in response to compressing the tissue, so as to achieve a target closure force.

As clamp arm (1090) contacts tissue, outer shaft (1060) experiences a counter force due to the tissue that attempts to pull outer shaft (1060) distally but is countered by the spring force provided by wave spring (1188). Since the force of clamp arm (1090) actively contacting tissue against ultrasonic blade (1092) exceeds spring force provided by wave spring (1188), wave spring (1188) compresses to a partially compressed state. Contrary to FIG. 29B where translating member (1158), proximal washer (1182), wave spring (1188), distal washer (1183), tuning member (1186), and elongate shaft (1184) are each driven proximally in a linear manner, translating member (1158) pushes proximal washer (1182), wave spring (1188), distal washer (1183), and tuning member (1186) proximally while movement of elongate shaft (1184) depends on the opposing tissue force. For example, elongate shaft (1184) may still move proximally but a lesser distance as compared to translating member (1158) (i.e., variable closure speed).

Moving outer shaft (1060) pushes elongate shaft (1184) proximally against a pin retaining member (1206) that includes a recess for coupling pin (1172). In some versions, coupling pin (1172) may include a rigid base (e.g., metal) and a flexible overmold. Pin retaining member (1206) is secured with proximal carriage frame member (1120) using fasteners (not shown). As described above, outer shaft (1060) and elongate shaft (1184) are translatable coupled, such that outer shaft (1060) moves proximally when translating member (1158) moves proximally, and vice versa. As shown in the transition between FIGS. 29C-29D and FIGS. 30-31, at step (1618), when actual distance (D) is greater than minimum distance (Dmin), the closure load is sufficient for hemostasis.

As shown in FIGS. 30-31, at step (1620), the rotary motor may be stopped before actual distance (D) equals final distance (Dmin), which factors in the variation associated with the nominal distance (Dnom). FIG. 29D shows a cross-sectional view of surgical instrument (1010) of FIG. 29B with translating member (1158) proximally translated further relative to second spur gear (1156), as closure force adjusting mechanism (1180) moves to a fully compressed state as end effector (1016) further clamps tissue. Proximal translation of outer shaft (1060) closes clamp arm (1090) relative to ultrasonic blade (1092) by causing opposing slots (1106) of outer shaft (1060) to move proximally while pivot pin (1102) remains relatively fixed. As shown in FIG. 29D, wave spring (1188) is effectively bottomed out and functionally removed from actuation assembly (1032). Similar to FIG. 29C, flange (1190) of elongate shaft (1184) is spaced a second distance from the distal portion of elongate shaft (1184). Additionally, distal washer (1183) may contact a detent of electronic switch (1146) to indicate to circuit board (1142) the longitudinal position of distal washer (1183). In some versions, electronic switch (1146) may verify the desired amount of closure force is applied to the tissue. Also, tuning member (1186) may be adjusted to change the predetermined closure force to compress the tissue between first and second jaws (1086, 1088). At step (1622), surgical instrument (1010) is at the fully clamped position.

D. Relationship Between Closure Force and Motor Position

Figure 32:
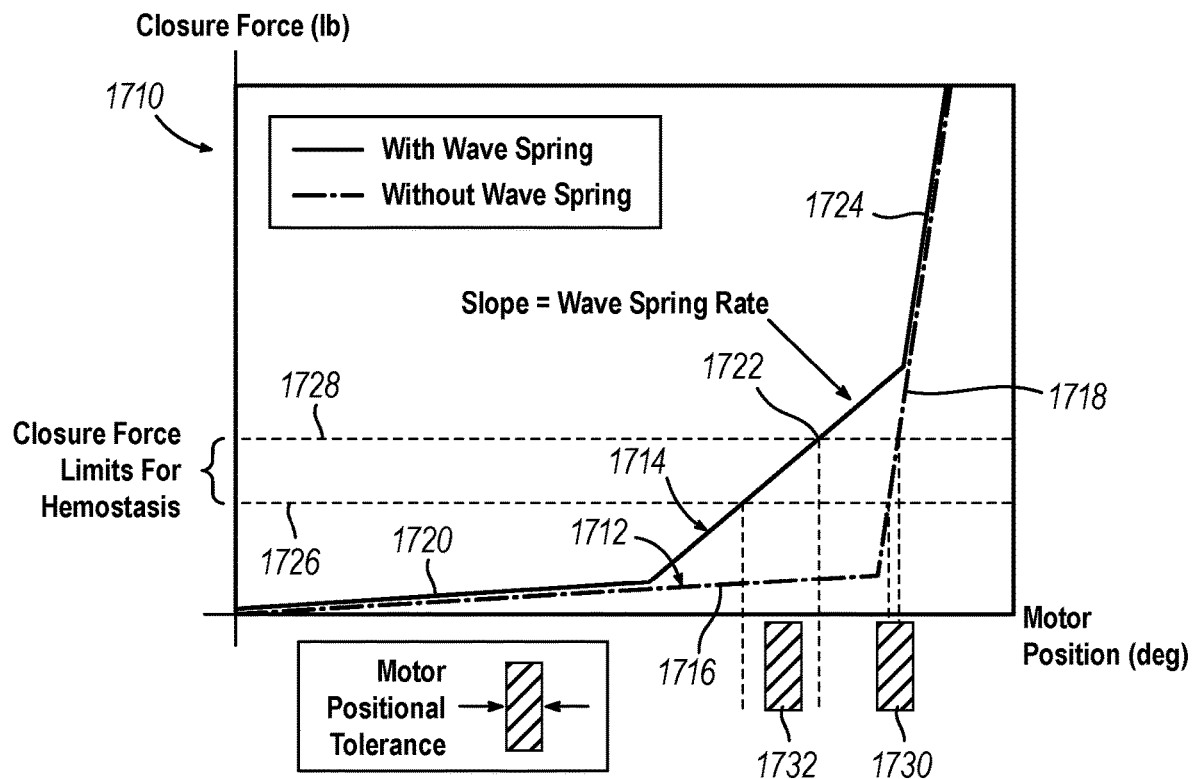
FIG. 32 depicts a graph of exemplary first and second plots of the closure force with respect to motor position, where the first plot depicts the surgical instrument of FIG. 9 including a wave spring of FIG. 16 and the second plot depicts the surgical instrument of FIG. 9 without a wave spring of FIG. 16.
Figure 33:
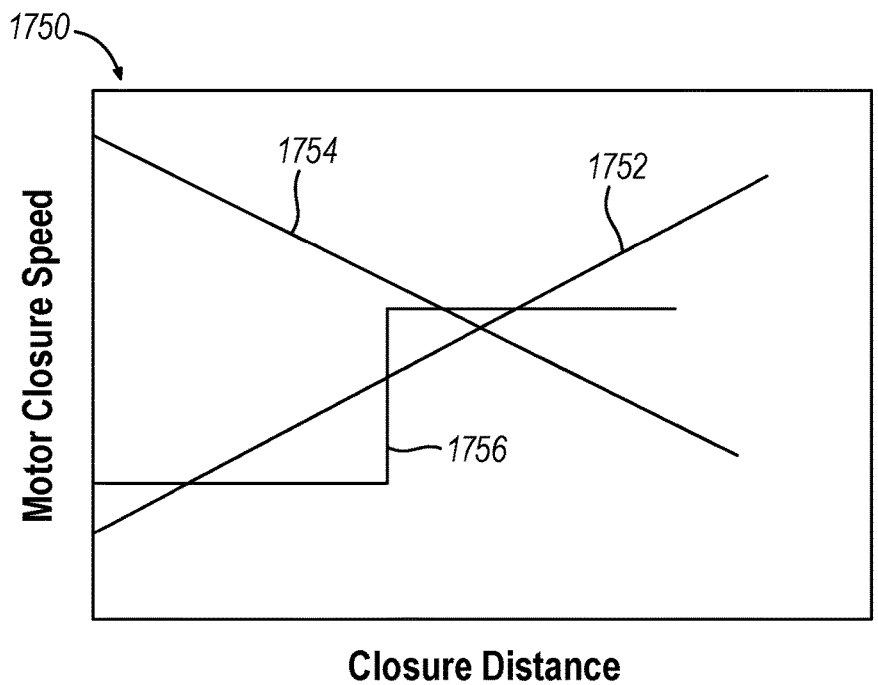
FIG. 33 depicts a graph of exemplary first, second and third plots of motor closure speed with respect to closure distance, where the first plot depicts the motor rotational output is linearly increasing, the second plot depicts the motor rotational output is linearly decreasing, and the third plot depicts the motor rotational output is binary.

FIG. 32 shows a graph of the closure force with respect to motor position with a first plot (1712) of surgical instrument (1010) without wave spring (1188) and a second plot of surgical instrument (1010) including wave spring (1188). As shown, first plot (1712) includes first and second segments (1716, 1718). First segment (1716) of first plot (1712) shows closure force relative to motor position prior to tissue being contacted. Second segment (1718) shows closure force relative to motor position after tissue is contacted, which is shown by the significant increase in closure force. As shown, first and second segments (1716, 1718) are generally linear. When end effector (1016) begins to compress tissue, the closure force increases resulting in a steeper slope.

Second plot (1714) includes first, second, and third segments (1720, 1722, 1724). First segment (1720) shows closure force relative to motor position prior to first and second jaws (1086, 1088) contacting tissue and prior to wave spring (1188) being compressed. As shown, first segment (1716) of first plot (1712) and first segment (1720) of second plot (1714) generally exhibit the same or similar slope up until this point. This gradual slope is when closing surgical instrument as end effector (1016, 1350) may include a small amount of friction. First segment (1720) of second plot (1714) is generally shown in the transition between FIGS. 29A-29B. Second segment (1722) shows closure force relative to motor position after the tissue has been contacted (and as tissue is being compressed) and as wave spring (1188) is being compressed but prior to wave spring (1188) reaching the compressed state. Second segment (1722) of second plot (1714) is generally shown in the transition between FIGS. 29B-29C. Third segment (1724) shows as tissue is being compressed and after wave spring (1188) has reached the compressed state, which is shown by the increased slope of third segment (1724) relative to second segment (1722). Once wave spring (1188) reaches the compressed state, wave spring (1188) may not further compress and is functionally removed from actuation assembly (1032). Third segment (1724) of second plot (1714) is generally shown in FIG. 29D. First, second, and third segments (1720, 1722, 1724) may be each generally linear.

Regarding first plot (1712), there may be instances where the motor does not have the positional tolerance to obtain both a lower closure force limit (1726) for hemostasis and an upper closure force limit (1728) for the desired hemostasis. In some instances, the accuracy and precision of motor accuracy (denoted by the width of tolerance range (1730, 1732) exceeds the width of encountered forces (between vertical blue dashed lines). For example, the motor may not have sufficient accuracy and precision to deliver clamping force without closure force adjusting mechanism (1180) (e.g., wave spring (1188)) with a motor-position based control due to lower and upper closure force limits (1726, 1728) being insufficient for the positional tolerance of the motor, as shown by tolerance range (1730). In some instances, the motor may not have sufficient accuracy and precision to repeatedly deliver the desired clamp force without including closure force adjusting mechanism (1180) (e.g., wave spring (1188)) to decrease the slope of the curve using position control.

With closure force adjusting mechanism (1180) (e.g., wave spring (1188)), the motor has the accuracy and precision to repeatedly deliver clamping force using position based closure control as lower and upper closure force limits (1726, 1728) are greater of the positional tolerance of the motor, as shown by tolerance range (1732). The motor has the accuracy and precision to deliver clamp force with closure force adjusting mechanism (1180) (e.g., wave spring (1188)). This allows for position control of the closure regardless of the amount of losses in robotic system (10, 28), including surgical instrument (1010). The position may be moved until desired compression loads of first jaw (1086, 1352) and second jaw (1088, 1354) of end effectors (1016, 1350). Incorporation of wave spring (1188), allows for slope of closure force curve once tissue beings to compress to decrease (i.e., less steep). Additionally, wave spring (1188) may provide overload protection. Wave spring (1188) increases allowable motor positions (as shown on the x-axis of FIG. 32) for positioned controlled closing of end effector (1016, 1350) of surgical instrument (1010).

E. Closure Control Using Motor Control Based Closure

FIG. 33 shows a graph (1750) of motor closure speed with respect to closure distance. As shown, graph (1750) includes with first, second, and third plots (1752, 1754, 1756). As previously described, the rate at which at least one of first jaw (1086, 1352) or second jaw (1088, 1354) is configured to pivot relative to the other of first jaw (1086, 1352) or second jaw (1088, 1354) defines a closure speed. With a linear actuation assembly, the closure speed experienced by first and second jaws (1086, 1088) is directly proportional (factoring out friction and other system losses) to the rotational motor output both prior to and while compressing the tissue between first jaw (1086, 1352) and second jaw (1088, 1354) of end effectors (1016, 1350). For example, the motor closure speed may at least one of linearly increase, linearly decrease, or remain constant.

As shown in FIG. 33, closure speed may be varied by using a motor with a variable rotary drive motor output. A first plot (1752) shows where the motor rotational output is linearly increasing as tissue is approached. A second plot (1756) shows where the motor rotational output is linearly decreasing as tissue is approached, which may be beneficial when the open action is reversed as in a touch and spread dissection. However, other curves and controls that vary by motor controls are also envisioned. A third plot (1758) shows where the motor rotational output is binary (i.e., a binary speed difference).

IV. EXEMPLARY SURGICAL INSTRUMENT WITH REUSABLE STAGE

A. Overview

In some instances, it may be desirable to use various alternative surgical instruments with robotic systems (10, 28) described above in addition to, or in lieu of, surgical instruments (14, 1010) described above. Such alternative surgical instruments may be desirable to provide improved operability when used with robotic systems (10, 28). In some instances, it may be beneficial to reuse one or more components of surgical instrument (14, 1010). Reusing one or more components of surgical instrument (14, 1010) may reduce medical waste and/or reduce per use costs of surgical instrument (14, 1010). As a result, it may be beneficial to couple and/or decouple reusable components and disposable components in a straightforward and reliable manner.

FIGS. 34A-38 show a third exemplary alternative surgical instrument (1810) that is configured to be used with robotic systems (10, 28) described above. Surgical instrument (1810) of the present example is shown as an ultrasonic surgical instrument that uses ultrasonic energy to treat tissue. Alternatively, it is envisioned that surgical instrument (1810) may be modified to treat tissue in other manners. For example, it is envisioned that surgical instrument (1810) may be modified to cut and staple tissue using end effector (1350) as shown in FIGS. 23-24, or apply radiofrequency energy to treat tissue using one or more radiofrequency electrodes. Other suitable end effectors are also envisioned including end effectors including one drive (e.g., a suction irrigator).

It should be understood that surgical instrument (1810) of the present example is substantially similar to surgical instrument (1010) described above, except where otherwise noted herein. For instance, similar to surgical instrument (1010) described above, surgical instrument (1810) of the present example includes an attachment interface (1812), a support structure (1814), an end effector (1816), a shaft assembly (1818), a carrier (1820), and an ultrasonic transducer assembly (1822). Similar to carrier (1020), carrier (1820) includes a translation driver (1826), an actuation driver (1828), a carriage (1830), and an actuation assembly (1832). While carrier (1820) is not shown as including guide rails, carrier (1820) may include one or more guide rails similar to guide rails (1034) discussed above. Also, as used herein, support structure (1814) may alternatively be referred to as a "housing" or a "stage" in one or more examples such that the terms "support structure, "housing" and "stage" my be interchangeably used in this context and are not intended to unnecessarily limit the invention described herein.

Figure 34A:
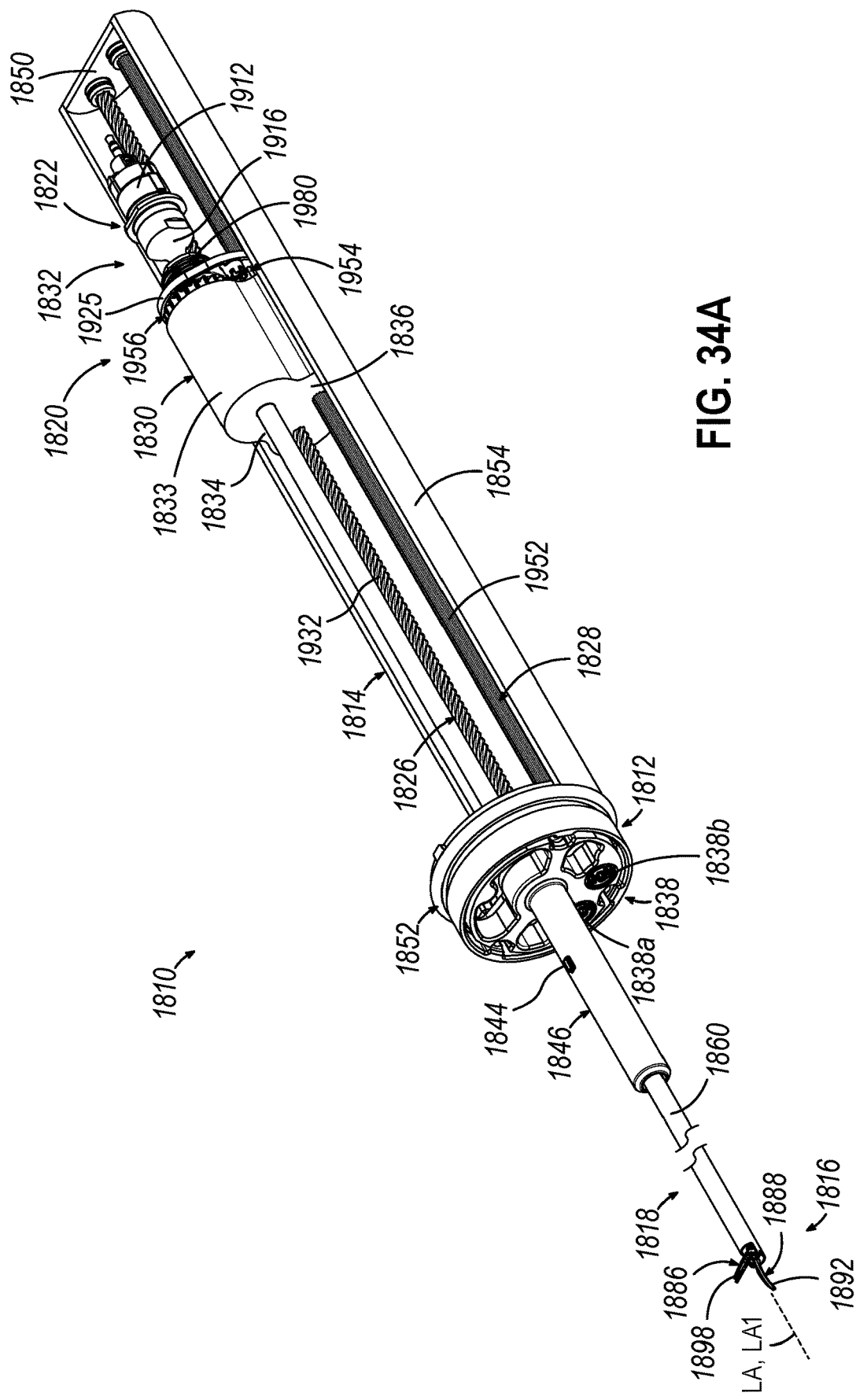
FIG. 34A depicts a perspective view of a third exemplary surgical instrument with a carriage of a carrier, a shaft assembly, and an end effector in a proximal position.
Figure 34B:
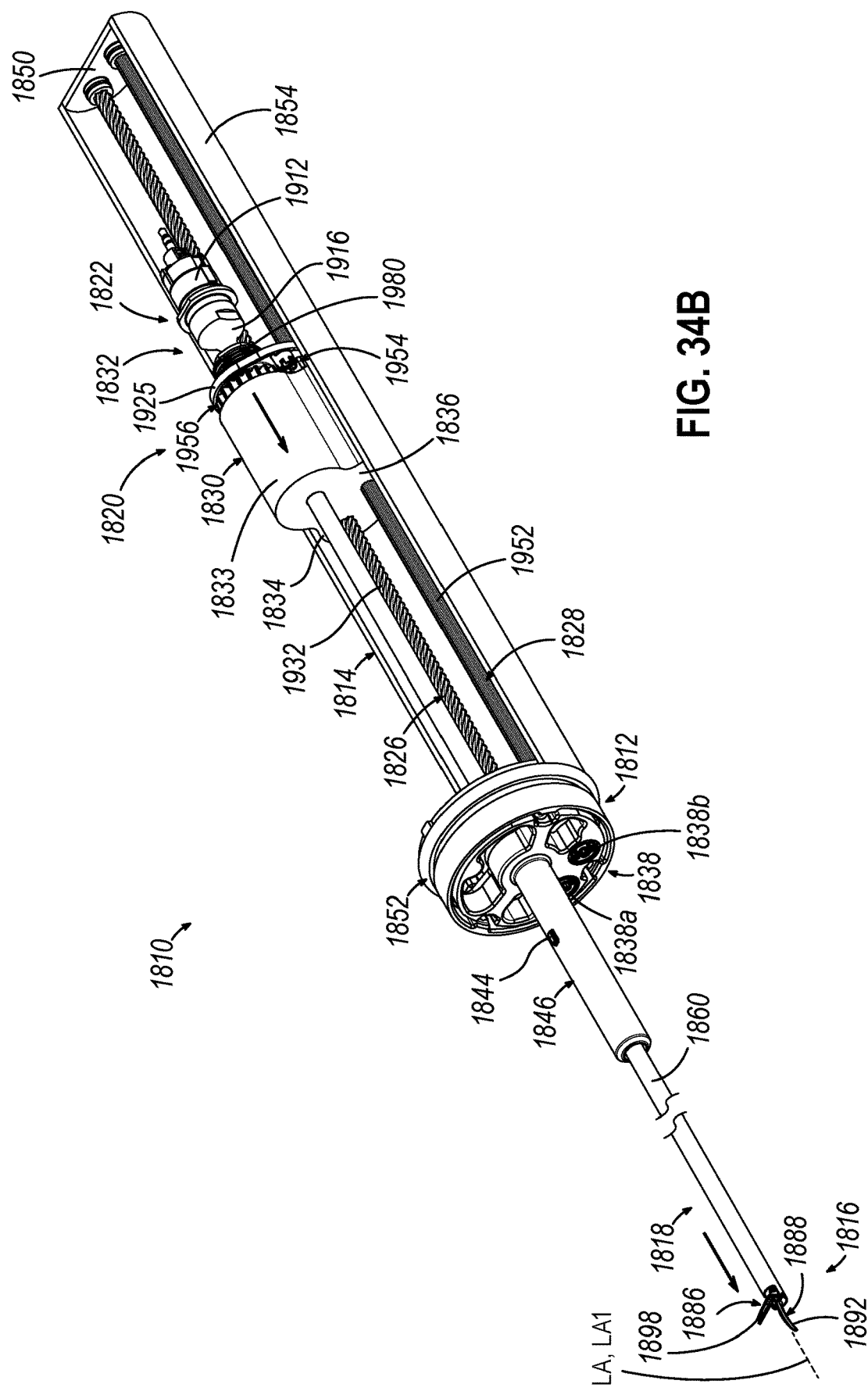
FIG. 34B depicts the perspective view of the surgical instrument similar to FIG. 34A, but with the carriage and the shaft assembly extended to a distal position.

Surgical instrument (1810) includes various drive components configured to move shaft assembly (1818) between a proximal position and a distal position and to actuate end effector (1816). Similar to surgical instrument (1010), surgical instrument (1810) may use various features configured to facilitate movement between end effector (1816) and drive inputs (e.g., first and second rotational drive inputs (1838a-b)). Such features may additionally or alternatively include pulleys, cables, carriers, such as a KART, and/or other structures configured to communicate movement along shaft assembly (1818). FIG. 34A shows a perspective view of surgical instrument (1810) with carriage (1830) and shaft assembly (1818) in an exemplary proximal position (also referred to as a retracted position). The proximal position places end effector (1816) relatively close and proximally toward instrument base (76). Conversely, FIG. 34B shows a perspective view of surgical instrument (1810) similar to FIG. 34A, but with carriage (1830) and shaft assembly (1818) extended to an exemplary distal position (also referred to as an extended position). As shown in FIG. 34B, the distal position places end effector (1816) relatively far and distally away from instrument base (76). While exemplary proximal and distal positions are shown, carriage (1830) may translate along the length of translation driver (1826) to place end effector (1816) at the desired position.

For example, one or more intermediate positions between the illustrated proximal and distal positions are envisioned but not shown.

As shown in FIGS. 34A-35 and 38, unlike carriage (1030), carriage (1830) includes a body (1833). Body (1833) includes first and second outwardly extending portions (1834, 1836). As used herein, first and second outwardly extending portions (1834, 1836) may alternatively be referred to as first and second lobes. Carriage (1830) also includes first receiving feature (1840) and a through hole (1842). Input receiving feature (1840) is configured to accommodate translation driver (1826). Input receiving feature (1840) may extend through at least a portion of first outwardly extending portion (1834). Through hole (1842) is sized and configured to allow actuation driver (1828) to rotate without rotating carriage (1830). For example, the inner diameter of through hole (1842) sized and configured to be larger than a circumscribed circle defined by splined shaft (1952). Through hole (1842) may extend through at least a portion of second outwardly extending portion (1836). As shown, first receiving feature (1840) and through hole (1842) extend parallel to longitudinal axis (LA). Unlike carriage (1030), in some versions, carriage (1830) may be integrally formed together as a unitary piece.

Similar to surgical instrument (1010), surgical instrument (1810) includes attachment interface (1812) similar to attachment interface (1012) described above. Attachment interface (1812) is configured to operatively couple with robotic arm (32) of robotic surgical system (10, 28). Similar to attachment interface (1012), attachment interface (1812) includes a plurality of drive inputs (1838) (which include first and second rotational drive inputs (1838a-b)) that face distally and are configured to operatively engage proximally facing drive outputs (68). First and second rotational drive inputs (1838a-b) are generally configured to move, actuate, and/or drive various components of surgical instrument (1810). While first and second rotational drive inputs (1838a-b) are shown and described, it is envisioned that surgical instrument (1810) may include more or fewer drive inputs as desired. Additionally, the number of drive outputs (68) may not equal the number of drive inputs (1838).

First and second rotational drive inputs (1838a-b) operative couple with respective corresponding drive outputs (68). First rotational drive input (1838a) may be operatively coupled with translation driver (1826). As a result, first rotational drive input (1838a) is configured to actuate translation driver (1826) to translate carriage (1830) and ultrasonic transducer assembly (1822) along longitudinal axis (LA). Second rotational drive input (1838b) may be operatively coupled with actuation driver (1828) to actuate end effector (1816) (e.g., between the open and closed positions). More specifically, second rotational drive input (1838b) is configured to actuate actuation driver (1828) to pivot clamp arm (1890) relative to ultrasonic blade (1892). While not shown, a sterile adapter similar to sterile adapter (1040) (see FIG. 9) may be disposed between robotic arm (32) and attachment interface (1812). Surgical instrument (1810) may self-align with the sterile adapter similar to surgical instrument (1010). An aligning feature (1844) of a guide shaft (1846) may couple with aligning feature (1048) of sterile adapter (1040) (see FIG. 9) to secure guide shaft (1846) with sterile adapter (1040).

Figure 38:
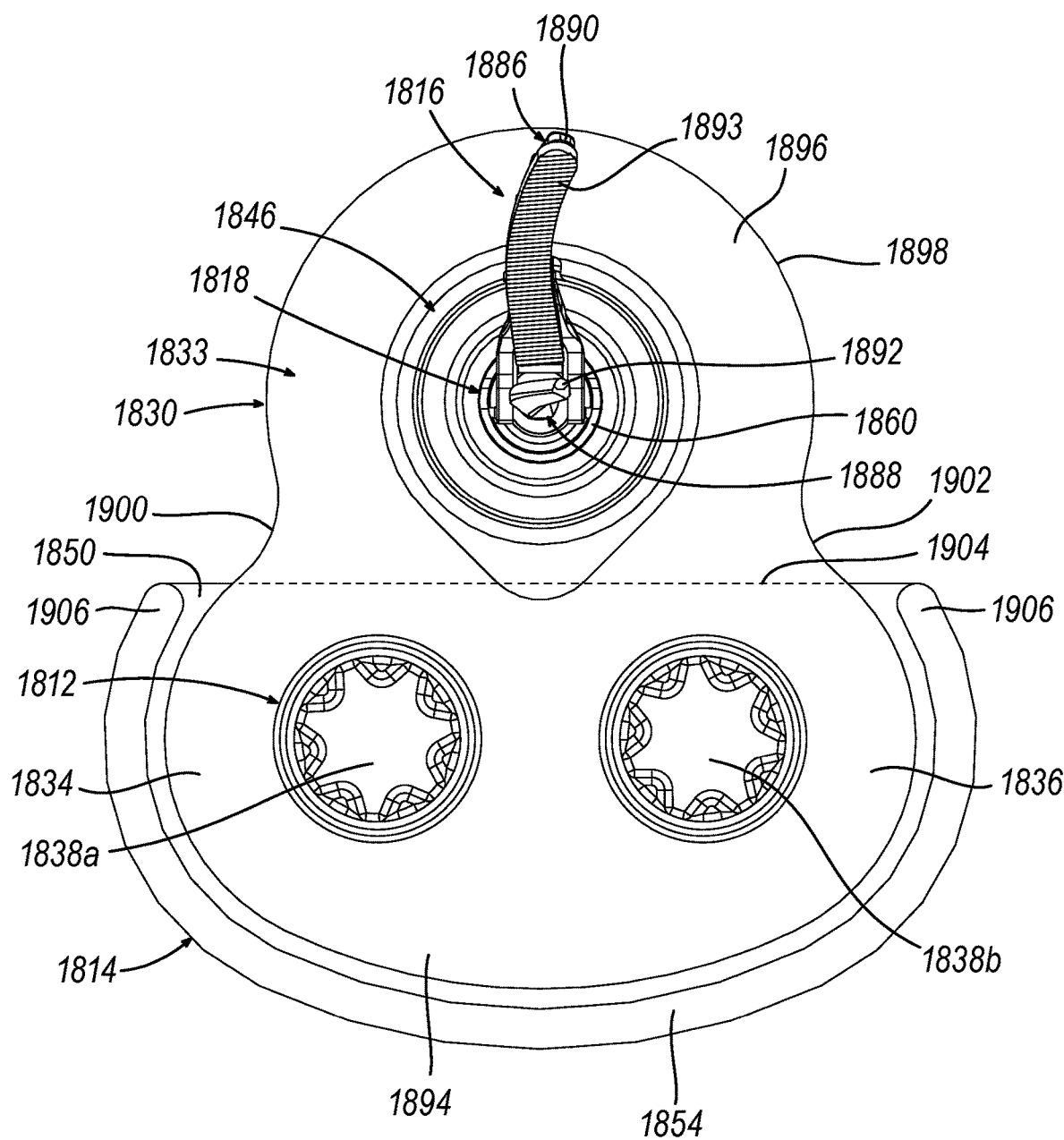
FIG. 38 depicts a distal end view of the surgical instrument of FIG. 34A, with a portion of the support structure removed to expose the carriage.

Similar to support structure (1014), support structure (1814) extends along longitudinal axis (LA). Support structure (1814) is configured to guide carriage (1830) along longitudinal axis (LA). In some versions, support structure (1814) may be formed of a generally rigid material (e.g., metal) so as to counter torsional forces due to actuation driver (1828). For example, support structure (1814) may be formed using stamped steel. Support structure (1814) includes a distally extending guide shaft (1846), a proximal frame member (1850), a distal frame member (1852), and a housing (1854) extending between proximal and distal frame members (1850, 1852). Distal frame member (1852) is spaced a distance along longitudinal axis (LA) from proximal frame member (1850). As shown, housing (1854) is generally C-shaped when viewed along a plane disposed perpendicular to longitudinal axis (LA) as shown in FIG. 38. This C-shape may be affected by the limited number of inputs for carriage (1830). However, housing (1854) may have a variety of other suitable shapes and sizes.

Surgical instrument (1810) includes shaft assembly (1818), which may be similar to shaft assembly (1018) of surgical instrument (1010). Shaft assembly (1818) is configured to extend from a center of instrument base (76) with an axis parallel to the axes of the drive inputs. Similar to shaft assembly (1018), shaft assembly (1818) extends proximally from end effector (1816). Shaft assembly (1818) is removably couplable with carriage (1830). For example, in some versions shaft assembly (1818) may be disposable while carriage may be reusable. Shaft assembly (1818) is similar to shaft assembly (1018) and includes an outer shaft (1860), an inner shaft (not shown), a sheath (not shown), and an acoustic waveguide (not shown) which are similar to outer shaft (1060), inner shaft (1062), sheath (1064), and acoustic waveguide (1066) of surgical instrument (1010) (see FIG. 12). Similar to surgical instrument (14, 1010), surgical instrument (1810) includes an instrument-based insertion architecture. Although not shown, it should be understood that in some examples, shaft assembly (1818) may include structures similar to articulation section (164) described above.

Figure 35:
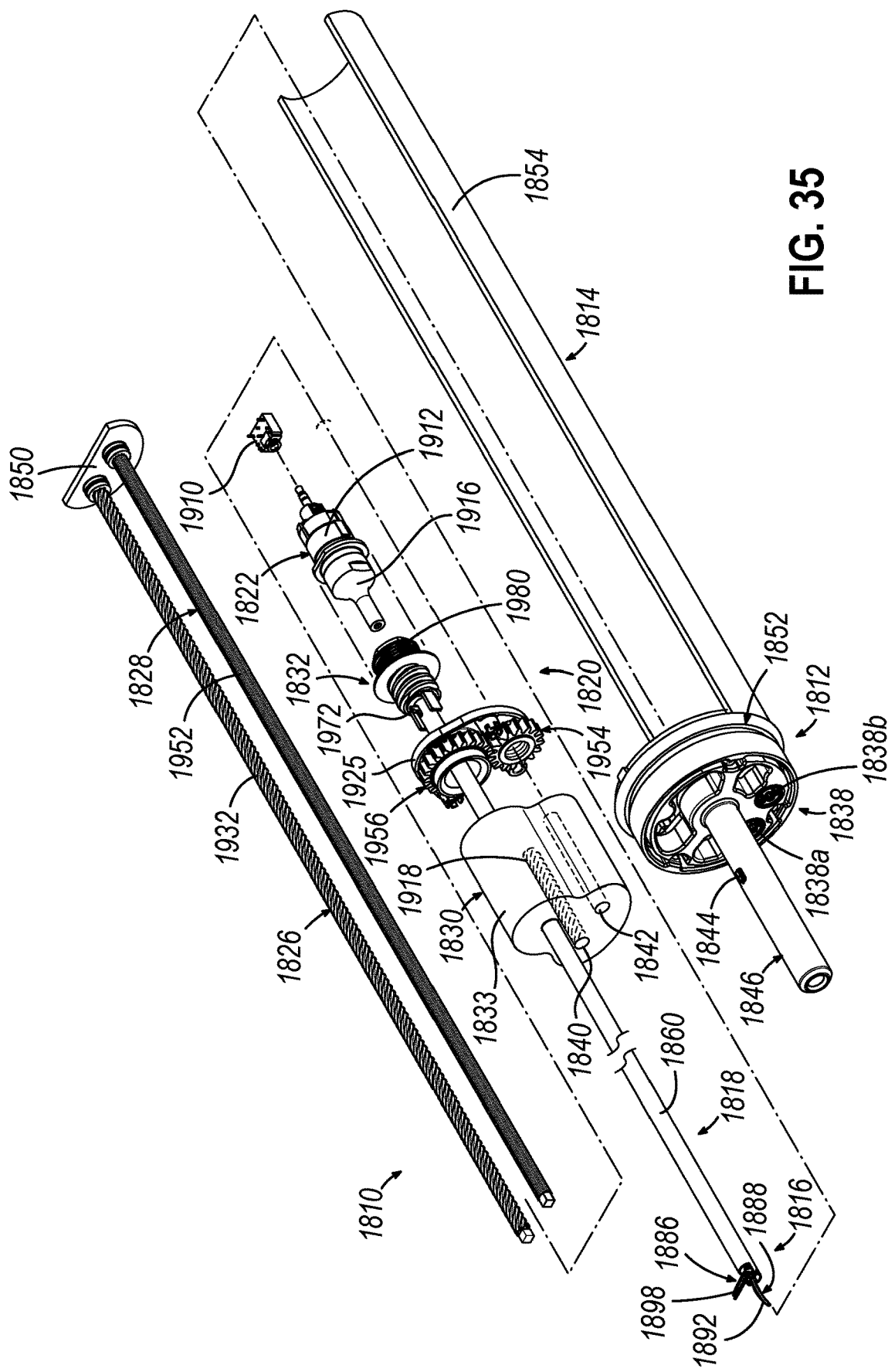
FIG. 35 depicts an exploded perspective view of the surgical instrument of FIG. 34A.

Acoustic drivetrain includes ultrasonic transducer assembly (1822) and the acoustic waveguide (not shown). Ultrasonic transducer assembly (1822) is similar to ultrasonic transducer assembly (154, 1022) described above. Similar to ultrasonic transducer assembly (1022), ultrasonic transducer assembly (1822) is operatively coupled with acoustic waveguide (not shown) using threads. Ultrasonic transducer assembly (1822) includes a transducer body (1912) and a horn (1916) extending distally from transducer body (1912). Ultrasonic transducer assembly (1822) is coupled with a cable connector (1910) (see FIG. 35) and the acoustic waveguide. As shown in FIG. 35, a cable connector (1910) is configured to provide power to ultrasonic transducer assembly (1822). Cable connector (1910) is configured to translate together with carriage (1830) along longitudinal axis (LA). In some versions, a cable management system (e.g., flexible cable guide (1024)) may be optionally included.

B. Exemplary Translation of End Effector

Figure 36:
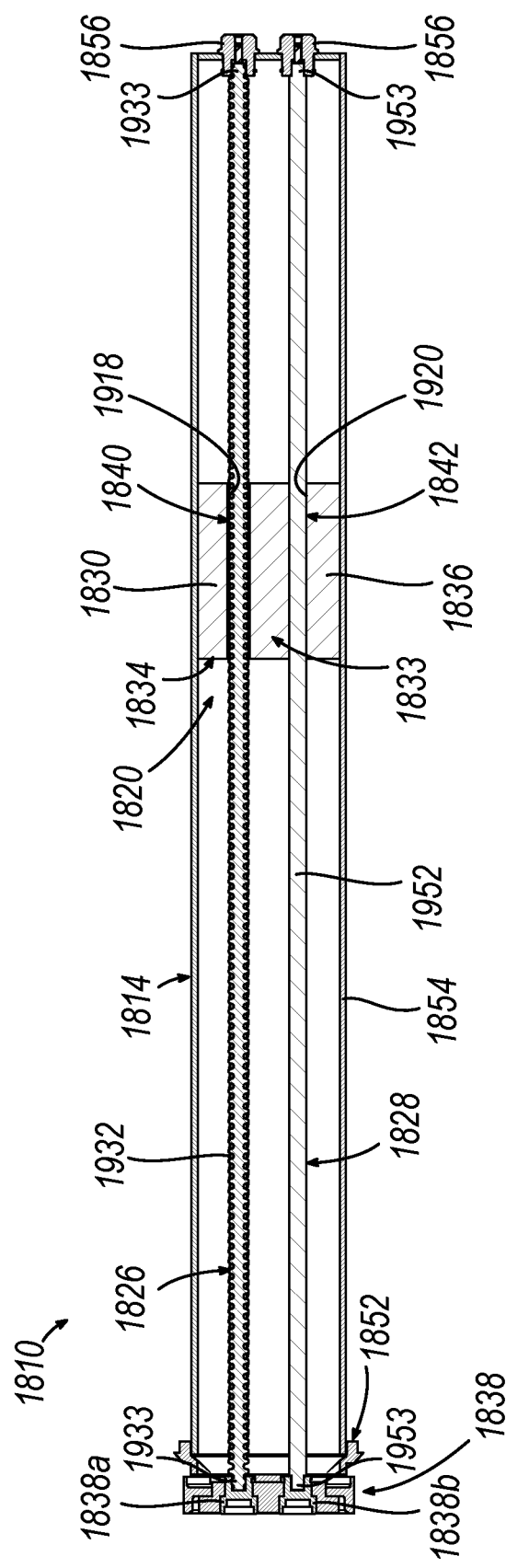
FIG. 36 depicts a sectional view of the surgical instrument of FIG. 34A.

FIG. 36 shows a sectional view of surgical instrument (1810) of FIG. 34A. As shown, translation driver (1826) and actuation driver (1828) extend between proximal and distal frame members (1850, 1852) and are captured by corresponding fixation members (1856) at the proximal end. Fixation members (1856) may allow for selective rotation of translation driver (1026) and actuation driver (1828). Fixation members (1856) may prevent translation of translation driver (1826) and actuation driver (1828) relative to proximal and distal frame members (1850, 1852). Translation driver (1826) is shown as including a threaded lead screw (1932), which may engage with one or more threaded components associated with carriage (1830) to thereby convert rotary motion of translation driver (1826), obtained from drive output (68) of robotic arm (32), into translation of carriage (1830). As shown in FIG. 36, threaded lead screw (1932) includes end features (1933), shown as squared off proximal and distal ends, to receive first rotational input (1838a) and fixation member (1856). While threaded lead screw (1932) is shown and described in the present example, it should be understood that in other examples various alternative configurations of translation driver (1826) may be used in addition to or in lieu of threaded lead screw (1932). Input receiving feature (1840) of carriage (1830) is shown as a threaded receiver that is configured to threadedly engage threaded lead screw (1932) to translate carriage (1830) along threaded lead screw (1932). Input receiving feature (1840) is shown as a through hole with helical internal threading (1918) (see FIG. 36) is configured to receive threaded lead screw (1932).

Similar to translation driver (1026), translation driver (1826) is configured to translate carriage (1830) along longitudinal axis (LA) so that ultrasonic transducer assembly (1822) moves from a proximal position along longitudinal axis (LA) to a distal position along longitudinal axis (LA) for inserting ultrasonic blade (1892) into a patient. Regarding the translation of end effector (1816), shaft assembly (1818), and carriage (1830), first rotational drive input (1838a) transmits the rotary motion to translation driver (1826). Translation driver (1826) then transmits the rotary motion to input receiving feature (1840) of carriage (1830) which is engaged with translation driver (1826). This translation may be obtained by rotating threaded lead screw (1932) relative to the threaded receiver having helical internal threading (1918) (see FIG. 35) to translate carriage (1830) along threaded lead screw (1932). End effector (1816), shaft assembly (1818), and carriage (1830) are configured to move along support structure (1814) using input receiving feature (1840) of carriage (1830) that interacts with translation driver (1826). Translation driver (1826) is operably engaged with carriage (1830) to translate carriage (1830) and end effector (1816) along longitudinal axis. Unlike threaded receiver (1134) of surgical instrument (1010), input receiving feature (1840) is disposed within carriage (1830). In some versions, input receiving feature (1840) may be integrally ford as a unitary piece together with carriage (1830).

In some versions, it may be desirable to reuse a portion or the entirety of support structure (1814) to reduce medical waste. For example, attachment interface (1812), support structure (1814), ultrasonic transducer assembly (1822), translation driver (1826), actuation driver (1828), and carriage (1830) may be reused in a subsequent procedure following the desired post processing methods, which may include sterilization. If desired, end effector (1816), shaft assembly (1818), and/or actuation assembly (1832) may be single-use disposable components or otherwise repurposed, after the appropriate sterilization process is performed if desired.

C. Exemplary Actuation of End Effector

Actuation driver (1828) is generally configured to selectively drive various portions of surgical instrument (1810) from one or more drive outputs (68) of robotic arm (32). For instance, in the present example, actuation driver (1828) includes a splined shaft (1952) (i.e., an elongate spur gear) configured to drive rotation of various components within carriage (1830) as carriage (1830) is moved using actuation driver (1828). Splined shaft (1952) includes end features (1953), shown as squared off proximal and distal ends to receive second rotational drive input (1838b) and fixation member (1856). Translating member (1958) of actuation assembly (1832) includes external threads (1970) configured to be threadably coupled within internal threads (1960) of carriage (1830). Through hole (1842) is shown as a through hole with internal threading (1920) (see FIG. 35) configured to receive splined shaft (1952). While splined shaft (1952) is shown and described in the present example, it should be understood that in other examples various alternative configurations of actuation driver (1828) may be used in addition to or in lieu of splined shaft (1952).

Figure 37:
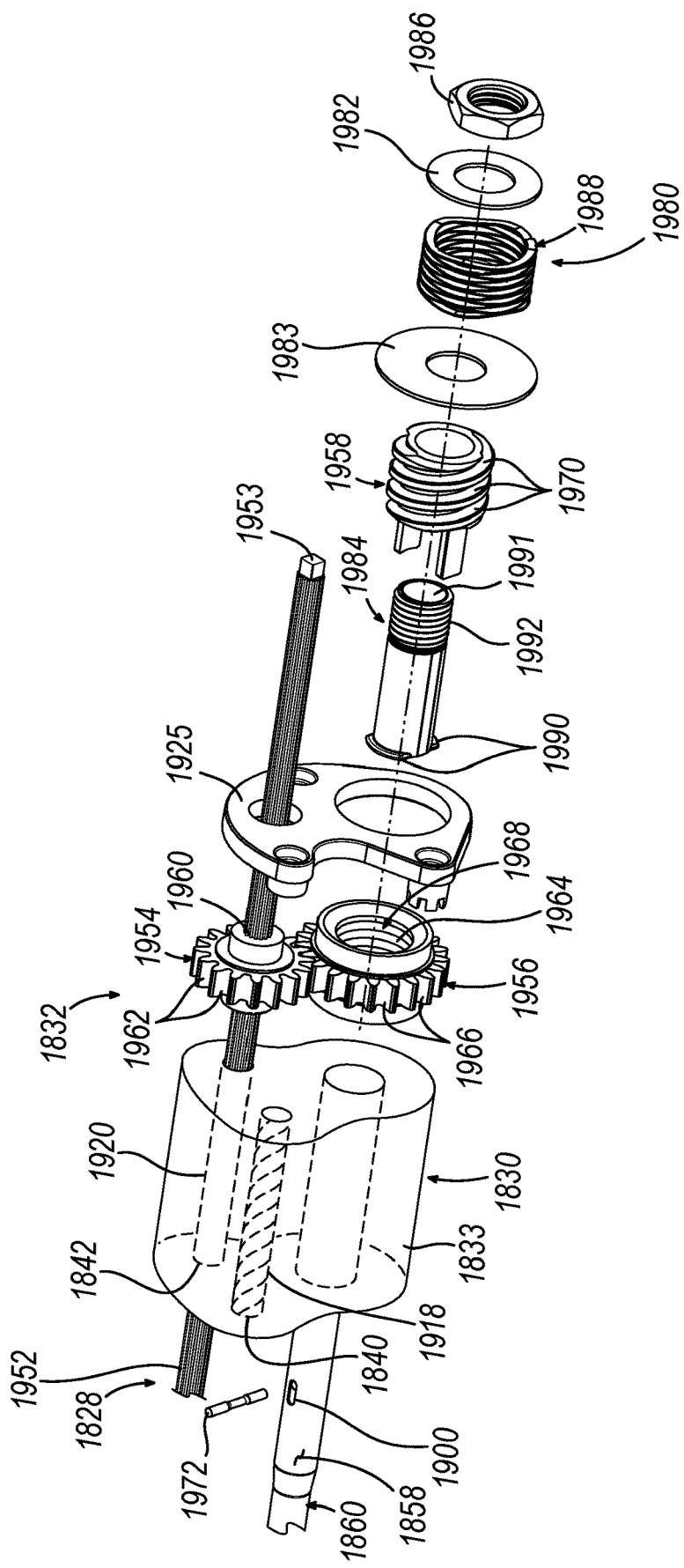
FIG. 37 depicts an exploded perspective view of portions of the carrier and the shaft assembly of FIG. 34A.

As shown in FIGS. 34A-35 and 37, and similar to actuation assembly (1032), actuation assembly (1832) includes a first spur gear (1954), a second spur gear (1956), and a translating member (1958). As shown in FIG. 37, first spur gear (1954) is rotatably coupled with splined shaft (1952). First spur gear (1954) includes an internal aperture (1960) having a corresponding spline pattern to rotatably couple with splined shaft (1952). First spur gear (1954) also includes a first plurality of gear teeth (1962). Second spur gear (1956) includes a central aperture (1964) and a second plurality of gear teeth (1966). At least a portion of central aperture (1964) of second spur gear (1956) includes internal threading (1968). Translating member (1958) (which may include a lead screw) includes external threading (1970). Rotation of internal threading (1968) of second spur gear (1956) relative to external threading (1970) of translating member (1958) is configured to translate translating member (1958) either proximally or distally. Intermediate carriage frame member (1925) may be coupled with carriage (1830) using one or more fasteners to translatably fix first and second spur gears (1954, 1956) therebetween.

As shown in FIGS. 35 and 37, actuation assembly (1832) may include an optional closure force adjusting mechanism (1980), a proximal washer (1982), a distal washer (1983), a elongate shaft (1984), and a tuning member (1986), which may be respectively similar to closure force adjusting mechanism (1180), proximal washer (1182), distal washer (1183), elongate shaft (1184), and tuning member (1186) described above. Closure force adjusting mechanism (1980) is configured to selectively adjust the closure force while compressing the tissue between first and second jaws (1886, 1888) in a similar manner to closure force adjusting mechanism (1180) described above. As shown, closure force adjusting mechanism (1980) includes a resilient member (shown as a wave spring (1988)) configured to adjust the closure force between first and second jaws (1886, 1888). Tuning member (1986) is disposed adjacent proximal washer (1982) and includes internal threading (1204). As shown in FIG. 37, elongate shaft (1984) includes a flange (1990) at a distal end, a central through hole (1991), and external threading (1992) at a proximal end. A coupling pin (1972) may couple an elongate slot (1974) of outer shaft (1860), an aperture of the inner shaft (not shown), and a through bore (1978) of the acoustic waveguide.

The actuation of clamp arm (1890) may be similar to the actuation of clamp arm (1090) shown and described above with reference to FIGS. 29A-29D regarding surgical instrument (1010). Supporting portion (1894) of support structure (1814) is configured to resist the torsional forces exerted on carriage (1830) due to rotation of actuation driver (1828), similar to guide rails (1034) described above with reference to surgical instrument (1010).

FIG. 38 shows a distal end view of surgical instrument (1810) of FIG. 34A, with a portion of support structure (1814) removed to expose carriage (1830). Similar to end effector (1016), end effector (1816) includes first and second jaws (1886, 1888). Similar to end effector (1016), first jaw (1886) includes a clamp arm (1890) and second jaw (1888) includes ultrasonic blade (1892). The operation of end effector (1816) is substantially similar to the operation of end effector (1016). Clamp arm (1890) selectively pivots to clamp tissue between clamp arm (1890) and ultrasonic blade (1892). Ultrasonic blade (1892) is operable to vibrate at ultrasonic frequencies in order to effectively cut through and seal tissue, particularly when the tissue is being compressed between the clamp pad (1893) and ultrasonic blade (1892).

As shown in FIG. 38, support structure (1814) is sized and shaped to cradle and movably support a supporting portion (1894) of body (1833) that receives translation driver (1826) and actuation driver (1828). Imbalanced loads may cause carriage (1830) to twist. Supporting portion (1894) of support structure (1814) is configured to resist the torsional forces exerted on carriage (1830) due to rotation of actuation driver (1828), similar to guide rails (1034) described above with reference to surgical instrument (1010). Support structure (1814) also provides bending stiffness. Additionally, supporting portion (1894) may allow for a compact and light, yet sufficiently rigid, structure to resist torsional forces. Support structure (1814) may have a reduced mass. Portion (1894) of body (1833), which coincides with first and second rotational drive inputs (1838a-b), is thus covered by support structure (1814). Conversely, a free portion (1896) of body (1833), which does not coincide with first and second rotational drive inputs (1838a-b), but does include portions of shaft assembly (1818), remains uncovered by support structure (1814). In this respect, an outer profile (1898) of body (1833) and support structure (1814) are cooperatively shaped to accommodate first and second rotational drive inputs (1838a-b) and shaft assembly (1818) in a longitudinal direction. An exemplary demarcation line (1904) separates supporting and free portions (1894, 1896). Supporting portion (1904) includes inwardly facing portions (1906) configured to reduce torsional forces that cause torsional deflection of body (1833) of carriage (1830). As shown, body (1833) includes first and second recessed portions (1900, 1902) that extend inwardly toward body (1833). First and second recessed portions (1900, 1902) are disposed adjacent first and second outwardly extending portions (1834, 1836). Alternative outer profiles of bodies and support structures may thus be incorporated into other examples with differing numbers of drive inputs and/or portions of shaft assemblies, such that the invention is not intended to be unnecessarily limited to the particular outer profile (1898) of body (1833) slidably cradled by support structure (1814) in the present example.

V. CARRIER KART AND DRIVE HOUSING WITH VARIOUS CABLE CONFIGURATIONS

In some instances, it may be desirable for surgical instrument (14) to include one or more features of another exemplary ultrasonic surgical instrument (2000) with an electrical cable (2002), such as a power and/or sensor cable, that attaches to a fixed, communication port (2004) of a drive housing (2006) with the electrical cable (2002) further extending to a carrier KART (2008). Such housings may also be referred to herein as an "instrument body" or simply "body." Moreover, carrier KART (2008) may be constructed in accordance with any such carrier discussed herein. In any case, communication port (2004) provides structural support and integrity for electrical cable (2002) without additional devices or parts such as a brushed slip ring and brushes to conduct electrical communication between a controller (not shown) and carrier KART (2008). By way of example, a reduction in the number of parts in some cases may increase the reliability and decrease the cost to manufacture any such surgical instrument.

It will be appreciated that any exemplary ultrasonic surgical instruments (2000, 2100, 2200, 2300, 2400) described below in FIGS. 39-45 may be incorporated into the table based robotic systems (10, 28) described above. Drive housings (2006, 2306) of ultrasonic surgical instruments (2000, 2100, 2200, 2300, 2400) may attach to robotic arm (32) at instrument driver (66), more specifically drive housing attaches to rotational assembly (70). Instrument driver (66) may collectively rotate carrier KART (2008), end effector (116), shaft (114), and drive housing (2006) as a single unit around instrument driver axis (74). Additionally, other drive outputs (68) are configured to be driven at any position that rotational assembly (70) and drive housing (2006) are capable of being oriented.

Figure 39:
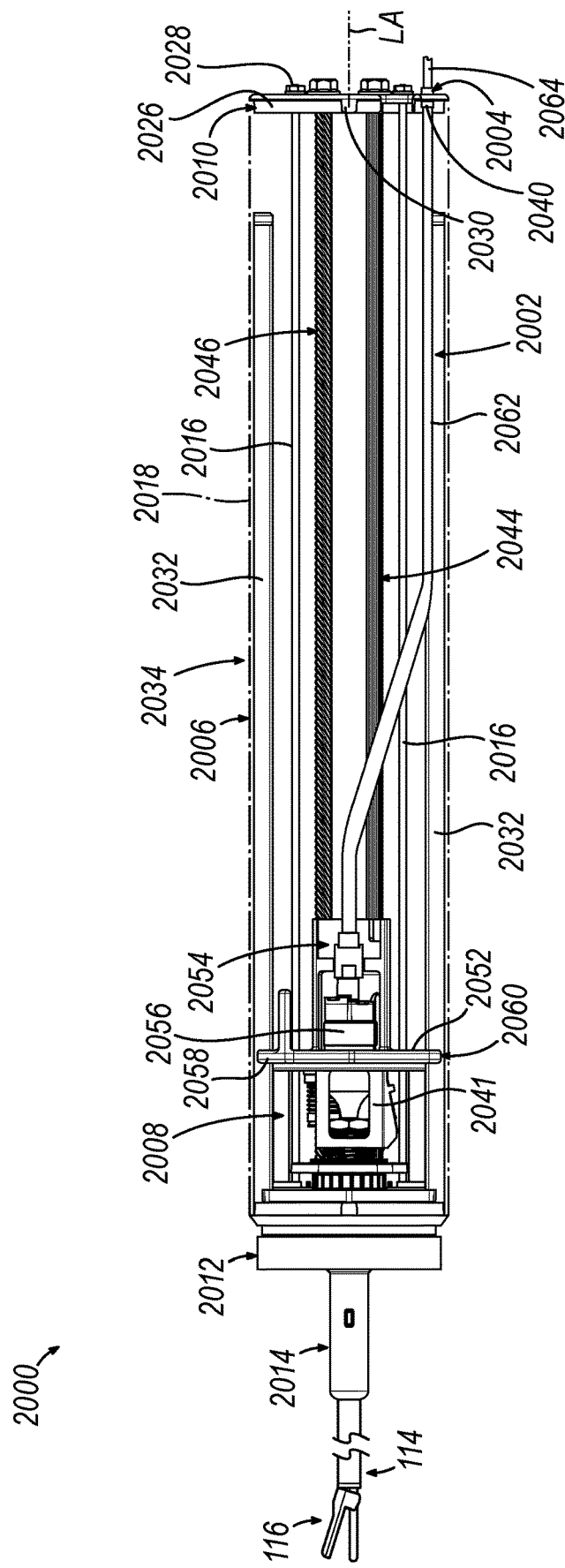
FIG. 39 depicts a side view of another exemplary surgical instrument with a tubular sidewall of a housing removed for added clarity having a carriage of a carrier KART distally positioned and an electrical cable attached to a proximal portion of the housing.
Figure 40:
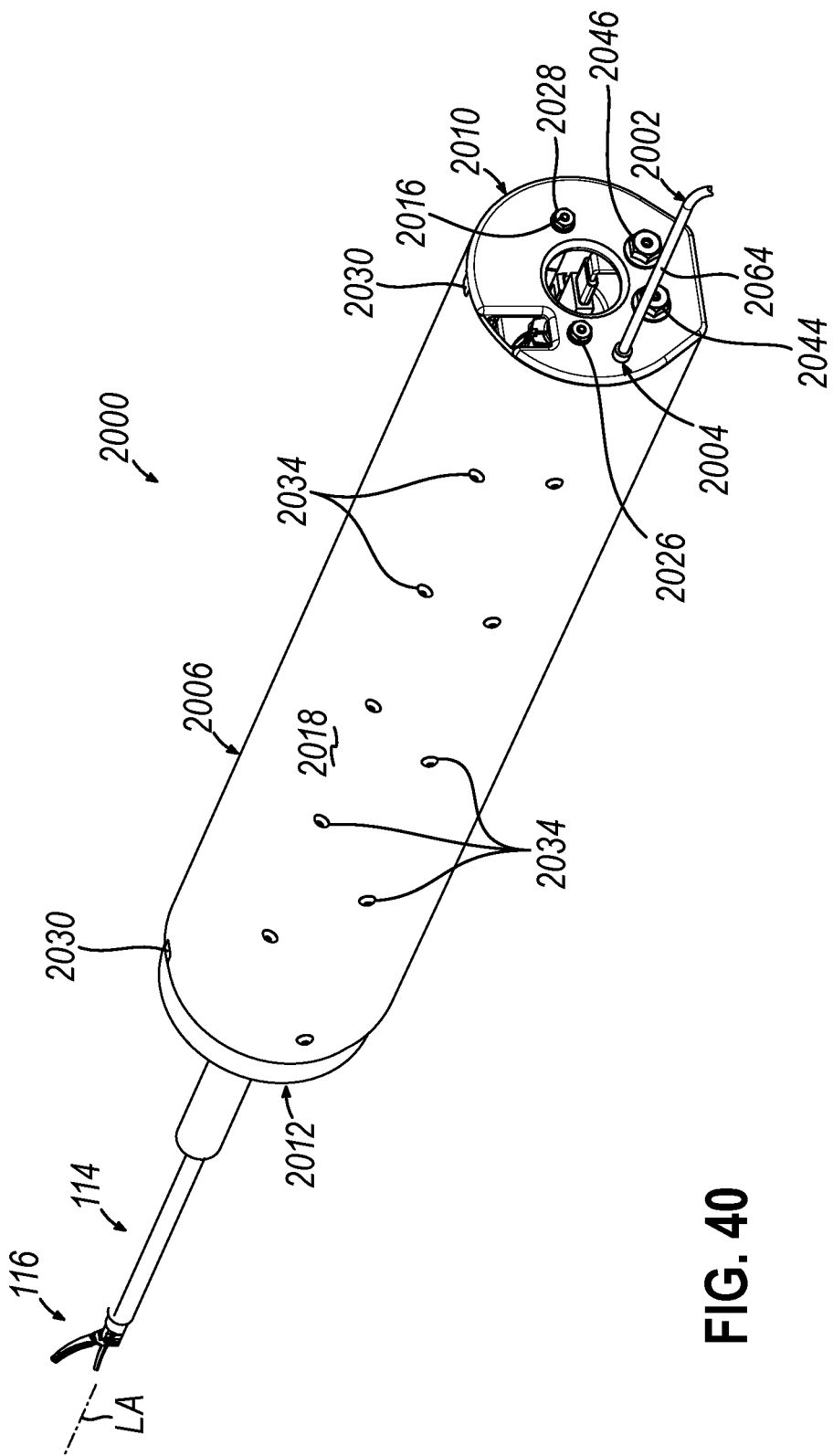
FIG. 40 depicts a perspective view of the surgical instrument of FIG. 39.

A. Carrier KART and Drive Housing with Electrical Cable Proximally Connected to Drive Housing As discussed briefly above, FIGS. 39-40 show exemplary ultrasonic surgical instrument (2000) including drive housing (2006), electrical cable (2002), carrier KART (2008), elongate shaft assembly (114), and end effector (116) such that like numbers below indicate like features discussed above in greater detail. Drive housing (2006) includes a proximal end cap (2010), a distal end cap (2012), a tubular guide (2014), a plurality of retention rods (2016), and a tubular sidewall (2018). Drive housing (2006) is configured to cover and generally transversely limit the movement of carrier KART (2008) along longitudinal axis (LA) of drive housing (2006). Tubular guide (2014) extends distally from a central portion of distal end cap (2012). Tubular guide (2014) is configured to support elongate shaft assembly (114) that extends distally to end effector (116) and allow elongate shaft assembly (114) to slide through tubular guide (2014) when end effector (116) transitions between a proximal position shown in FIG. 41B and a distal position shown in FIG. 41A.

Figure 46:
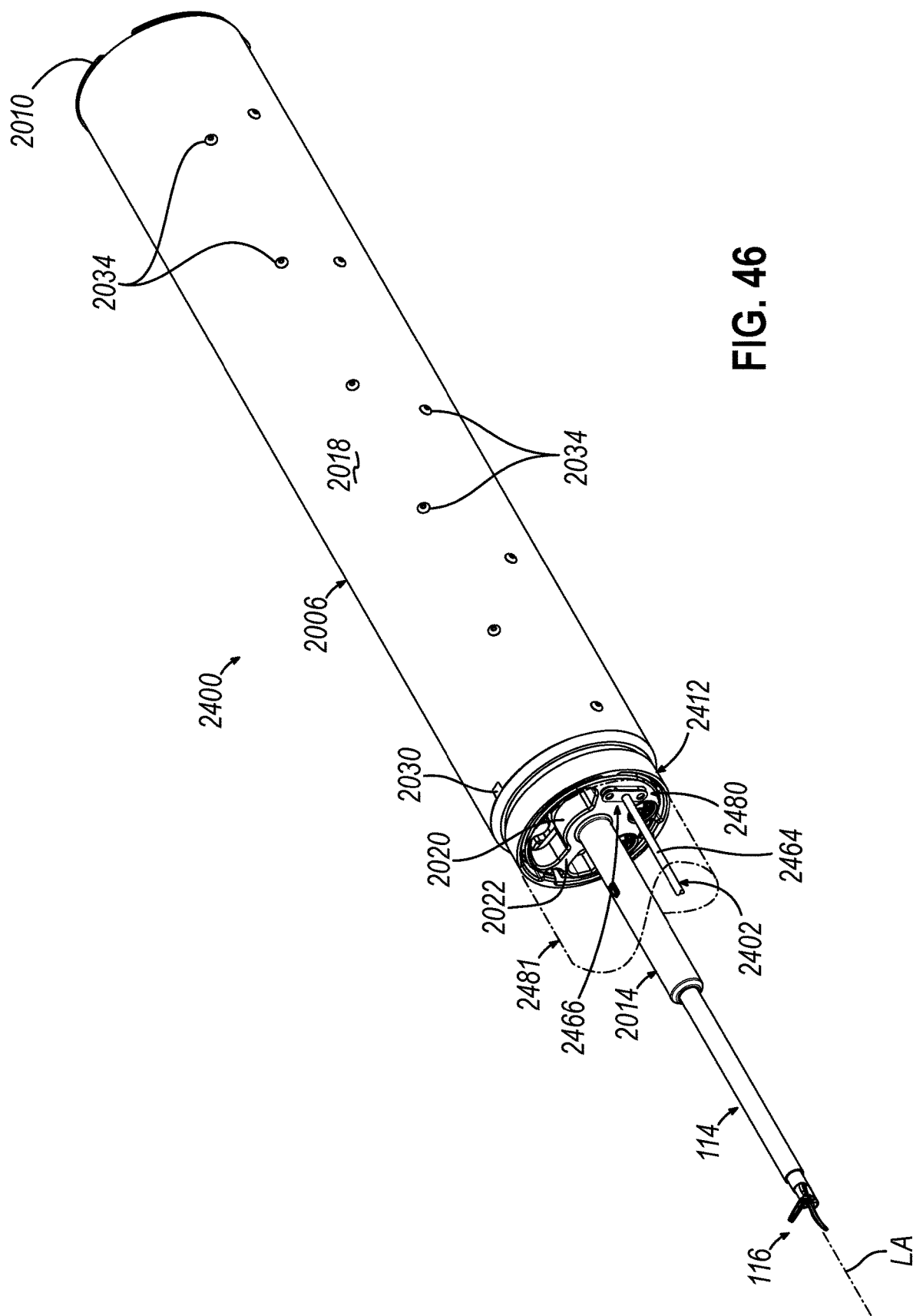
FIG. 46 depicts a perspective view of the surgical instrument of FIG. 45 viewing a distal portion of the housing fitted with a modular connector.

Distal end cap (2012) includes a central boss (2020) (see FIG. 46) located in central portion of distal end cap (2012), a plurality spokes (2022) (see FIG. 46) extending radially outwards from central boss (2020) (see FIG. 46), and a plurality of rotary drive inputs (2024) (see FIG. 46). Distal end cap (2012) is thus configured to be mated with input driver (66) so that drive housing (2006) may be rotated as discussed above.

Rods (2016) are threaded into distal end cap (2012) and extend longitudinally through a pair of bores (2026) in proximal end cap (2010). Each retention rod (2016) is secured with a nut (2028) on a distal face of proximal end cap (2010). While a pair of retention rods (2016) are shown in FIGS. 39-40, it will be appreciated that the number of retention rods (2016) may be any number sufficient to retain drive housing (2006) in a static position. Proximal and distal end caps (2010, 2012) include a plurality of tangs (2030) circumferentially locating tubular sidewall (2018). In this respect, tangs (2030) rotationally retain tubular sidewall (2018) relative to distal and proximal end caps (2010, 2012).

Tubular sidewall (2018) shown in FIG. 40 extends proximally from distal end cap (2012) as an exterior of drive housing (2006) and includes a pair translation rails (2032) configured to longitudinally align carrier KART (2008) within drive housing (2006). Translation rails (2032) are secured with a plurality of fasteners (2034) along the length of tubular sidewall (2018). Fasteners (2034) may include bolts, screws, rivets or any other such structure configured for such securement. Translation rails (2032) extend proximally from distal end cap (2012) towards proximal end cap (2010). In some versions, translation rails (2032) extend proximally to proximal end cap (2010). While the example shown in FIGS. 39-40 shows two such translations rails (2032) it will be appreciated that drive housing (2006) may have any desired number of such translation rails (2032) to longitudinally align carrier KART (2008) within drive housing (2006).

Proximal end cap (2010) is proximally located relative to tubular sidewall (2018). Electrical cable (2002) is secured to communication port (2004) in proximal end cap (2010) by a grommet (2040) and distally extends further to a movable portion of carrier KART (2008), such as a carriage (2041) discussed below in greater detail. Grommet (2040) is configured to inhibit electrical cable (2002) from chaffing or becoming degraded, such as by inhibiting direct contact with other surrounding wear-inducing surfaces.

Ultrasonic surgical instrument (2000) also generally includes a spline shaft (2044) and a threaded rod (2046). Rotary drive inputs (2024) (see FIG. 46) are rotatably secured in distal end cap (2012) and are configured to provide power transmission to spline shaft (2044) and threaded rod (2046). Rotary drive inputs (2024) (see FIG. 46) are rotatably driven by remotely mounted electric motor (not shown) or pneumatic motor (not shown). Threaded rod (2046) includes rotary drive input (2024) (see FIG. 46) located on distal end cap (2012) that is rotated to translate carriage (2041) of carrier KART (2008) proximally and distally relative to drive housing (2006). Threaded rod (2046) includes threads configured to translate carriage (2041) of carrier KART (2008) along the longitudinal axis (LA) of drive housing (2006) with precision and accuracy relative to the patient during use.

Carriage (2041) of carrier KART (2008) includes a frame (2052) and a carrier KART connector (2054) and is configured to movably support an ultrasonic transducer assembly (2056) thereon. Frame (2052) includes a transverse plate (2058) having a slots (2060) that respectively receive rails (2032) such that carriage (2041) is configured to slide longitudinally along translation rails (2032) when translating between the distal and proximal positions. Frame (2052) thus provides support for carrier KART connector (2054), and ultrasonic transducer assembly (2056). In the present example, carrier KART connector (2054) is fixedly mounted within frame (2052). Ultrasonic transducer assembly (2056) is fixedly mounted to frame (2052) and is configured to receive electricity via electrical cable (2002) and produce ultrasonic energy communicated to end effector (116) via shaft assembly (114).

With respect to FIG. 39, carriage (2041) of carrier KART (2008) is in the distal position within drive housing (2006). Carriage (2041) connects with electrical cable (2002) at carrier KART connector (2054). Electrical cable (2002) of the present example is fitted in grommet (2040) and enters from communication port (2004) located in proximal end cap (2010). In addition to providing electrical power to ultrasonic transducer assembly (2056), electrical cable (2002) may also communicate data via electrical signals, such as data to or from carrier KART (2008) or data to or from sensors (not shown). In this respect, electrical cable (2002) is not intended to be unnecessarily limited to communication of electrical power. Furthermore, electrical cable (2002) shown in the present example is flexible and may include braided conductors (not shown), insulation (not shown), and an armored covering (not shown). Electrical cable (2002), for example, may be a typical electrical cable, communication cable, a shielded cable, a twisted pair, a ribbon cable, a flex circuit ribbon cable (see FIGS. 41A-41B), a helical cable (see FIGS. 42A-42B), or any other suitable cables configured to communicating electrical power and/or data. Conductors may be solid or braided and may be constructed of any material known in the art for good conductivity such as, but not limited to copper or aluminum. Insulation may be constructed of PVC, Kapton, rubber like polymers, oil impregnated paper, Teflon, silicone, or modified ethylene tetrafluoroethylene, or any material known in the art to be an electrical insulator. Armored covering may be metallic or non-metallic. Electrical cable (2002) in the present example is constructed of a non-metallic armored covering such as plastic or vinyl that facilitates the movement of electrical cable (2002). In some versions, a metallic armored covering may be helical in shape and provide superior protection for conductors. Metallic armored covering is capable of being moved but is less flexible than non-metallic armored covering. Metallic armored covering (not shown) may be constructed of stainless steel or aluminum.

Electrical cable (2002) may be a continuous piece of electrical cable (2002) as shown in the present example. Continuous electrical cable (2002) extends through communication port (2004) without an additional adapter, which may also be referred to as a connector, in the present example, although such an adapter may be used in other examples. In some versions, electrical cable (2002) may be sectioned into multiple pieces and connected in succession for electrical communication therealong. In some versions, electrical cable (2002) may be sectioned into a first section (not shown) classified as being within a sterile environment and a second section (not shown) classified as not being within a sterile environment. First section may be removed from ultrasonic surgical instrument (2000) for sterilization or replacement after a surgical procedure. Second section may remain connected because second section is outside of the sterile environment. Electrical cable (2002) sections may be joined by various electrical connectors (2066) (see FIGS. 41A-42B) known in the art to connect electrical cables. Additionally, electrical cables (2002) may be joined with solder or crimp connectors. The term "cable" is thus not intended to necessarily be singular but may be comprised of a plurality of wires to form such cable in some examples such that the term "cable" is not intended to unnecessarily limit the invention described herein.

FIGS. 41A-41B show another exemplary ultrasonic surgical instrument (2100) similar to ultrasonic surgical instrument (2000) fitted with a sectioned electrical cable (2102). Electrical cable (2102) includes two sections defined as an interior cable (2062) and an exterior cable (2064). Interior cable (2062) is joined to exterior cable (2064) with an adapter, such as connector (2066), or by other methods known in the art to connect electrical cables. FIG. 41A shows ultrasonic surgical instrument (2100) with carriage (2041) of carrier KART (2008) located in the distal position and carrier KART connector (2054) fitted with interior cable (2062). Notably in the present example, interior cable (2062) includes a self-managing, ribbon cable (2068). As used herein, the term self-managing refers to the ability of any such cable to form and guide itself to allow for full and repeated travel between the proximal and distal positions. Ribbon cable (2068) extends proximally from carriage (2041) to communication port (2004) in proximal end cap (2010). Ribbon cable (2068) may otherwise be referred to as a flat, generally planar cable, which may include a series of wire conductors aligned in parallel and in a generally planar and flexible arrangement. Ribbon cable (2068) is connected to exterior cable (2064) with connector (2066) and may further define electrical cable (2102) as described further above. Ribbon cable (2068) is fully extended with carriage (2041) of carrier KART (2008) in the distal position. Ribbon cable (2068) provides the ability for cables to easily fold in one direction due to ribbon cable (2068) being flat and wide. In the present example, ribbon cable (2068) is more specifically a flex circuit ribbon, which is a flat printed circuit covered with a protective polymer coating.

FIG. 41B shows ultrasonic surgical instrument (2100) of FIG. 41A after carriage (2041) of carrier KART (2008) has been translated to proximal position. To this end, ribbon cable (2068) extends distally, and forms a proximal folded state (2069) thus managing itself upon movement of carriage (2041) to allow carriage (2041) full distal travel to the distal position while also being prepared to unfold in the event of proximal travel.

FIGS. 42A-42B show another exemplary ultrasonic surgical instrument (2200) similar to ultrasonic surgical instrument (2100) in many respects but having an electrical cable (2202) with a self-managing helical cable (2070). More particularly, FIG. 42A shows ultrasonic surgical instrument (2200) with carriage (2041) of carrier KART (2008) located in the distal position with carrier KART connector (2054) fitted with an interior cable (2062) that includes helical cable (2070) and an exterior cable (2064). Helical cable (2070) extends distally from proximal end cap (2010). Helical cable (2070) is connected to exterior cable (2264) with connector (2066). Helical cable (2070) is in a fully extended position, which also be referred to as an expanded state, with carrier KART (2008) in the distal position. Helical cable (2070) includes a plurality of coils (2072) defining a plurality of gaps (2074). Helical cable (2070) decompresses in an extended position. In the fully extended position, each of coils (2072) straighten and make each of gaps (2074) larger between respective coils (2072). This expansion and contraction self-manages helical cable (2070) thus inhibits tangling.

FIG. 42B shows ultrasonic surgical instrument of FIG. 42A after carriage (2041) of carrier KART (2008) has been translated to the proximal position. As carriage (2041) of carrier KART (2008) transitions from the distal position to the proximal position, helical cable (2070) compresses to progressively reduce the size of gaps (2074) between respective coils (2072) resulting in helical cable (2070) having a shorter overall defined length in a compressed state relative to the more elongated, expanded state.

Figure 43:
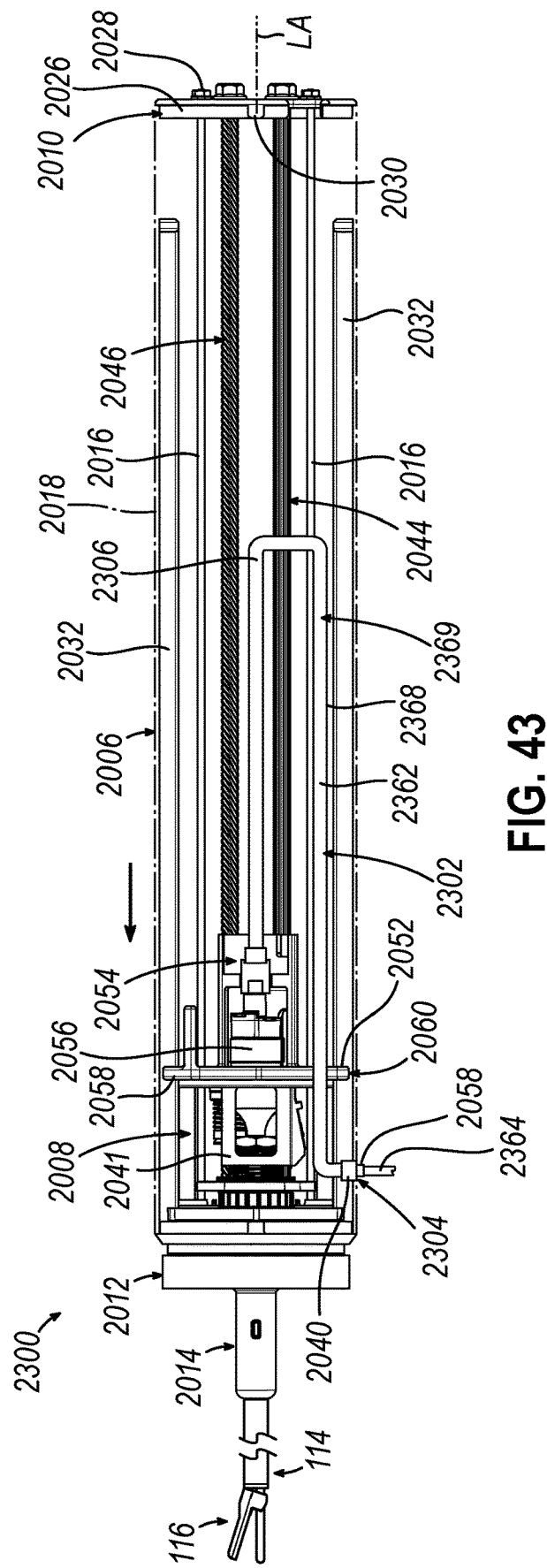
FIG. 43 depicts a side view of another exemplary surgical instrument with a tubular sidewall of a housing removed for added clarity having a carriage of a carrier KART distally positioned and an electrical cable attached to the tubular sidewall of the housing.
Figure 44:
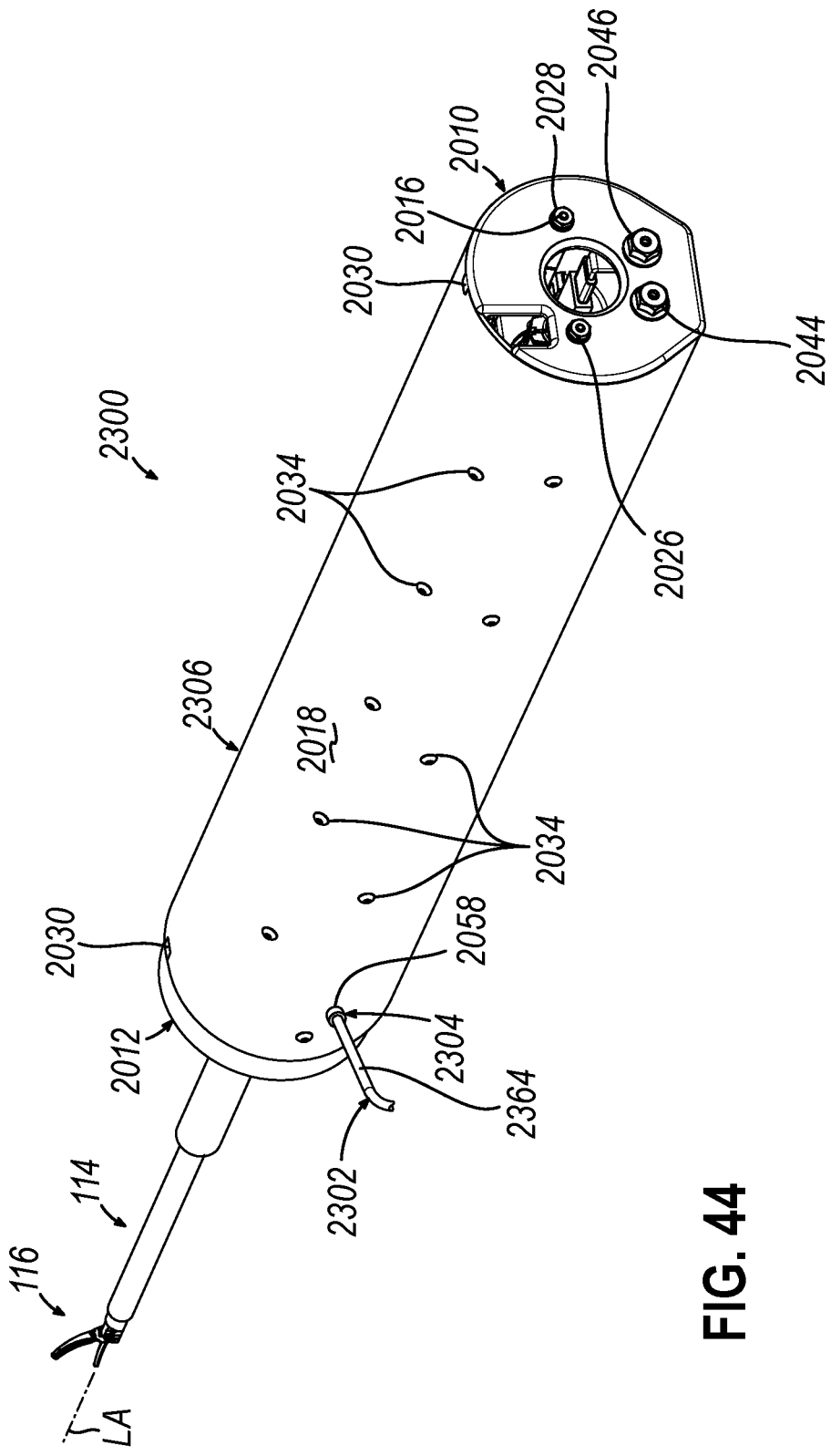
FIG. 44 depicts a perspective view of the surgical instrument of FIG. 43.

B. Carrier KART and Drive Housing with Electrical Cable Distally Connected to Tubular Sidewall of Housing FIGS. 43-44 shows another exemplary ultrasonic surgical instrument (2300) similar to ultrasonic surgical instrument (2000) but differs as discussed below. To this end, ultrasonic surgical instrument (2300) has an alternative example of a communication port (2304) on tubular sidewall (2018), more particularly shown at a relatively distal portion of tubular sidewall (2018) in the present example. An electrical cable (2302) penetrates through tubular sidewall (2018) of a drive housing (2306) and may include grommet (2040) or connector (2066). Electrical cable (2302) further extends to carriage (2041) of carrier KART (2008) and connects to carrier KART connector (2054). Electrical cable (2302) may be similar to other such cables discussed herein and may be continuous or sectioned as mentioned above.

With continued reference to FIGS. 43-44, carriage (2041) of carrier KART (2008) is in the distal position. Electrical cable (2302) includes an interior cable (2362) and an exterior cable (2364). Interior cable (2362) is a self-managing ribbon cable (2368) fitted with connector (2066) that connects to exterior cable (2364) at a communication port (2304). Ribbon cable (2368) forms a proximal folded state (2369) when carrier KART (2008) is in distal position. Ribbon cable (2368) extends towards the longitudinal axis (LA) from connector (2066) and bends proximally in the proximal folded state (2369) to define an elongated loop (2306) that changes the direction of cable (2368) from proximally extending, to distally extending, and connects to carrier KART connector (2054). Carriage (2041) of carrier KART (2008) may also be translated to the proximal position (not shown) similar to FIG. 41B. In the proximal position, ribbon cable (2368) will be in a fully extended position similar to ribbon cable (2068) shown in FIG. 41A but may have a relatively smaller loop (not shown) than elongated loop (2306) that diverts ribbon cable (2368) distally and connects ribbon cable (2068) to carrier KART connector (2054). In some versions, carrier KART connector (2054) may be distally facing so that ribbon cable (2368) is fully extended in the proximal position and thus may not include smaller loop (not shown).

Figure 45:
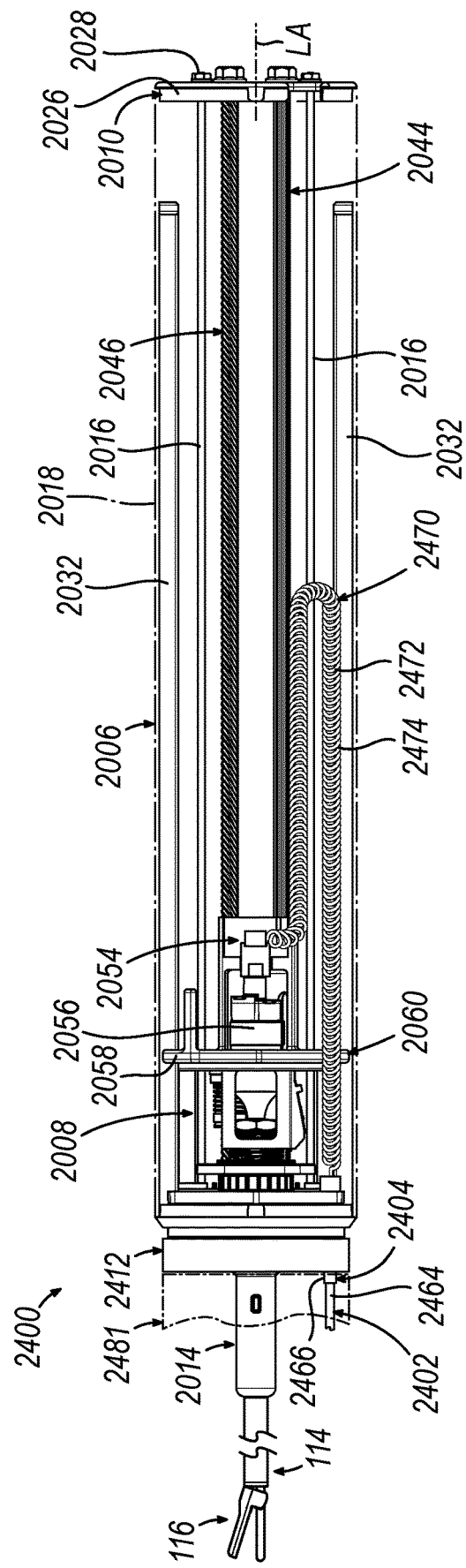
FIG. 45 depicts a side view of another exemplary surgical instrument with a tubular sidewall of a housing removed for added clarity having a carriage of a carrier KART distally positioned and an electrical cable attached to a distal portion of the housing.

C. Carrier KART and Drive Housing with Electrical Cable Distally Connected with a Modular Connector Through Distal End Cap FIGS. 45-46 show yet another exemplary ultrasonic surgical instrument (2400) similar to ultrasonic surgical instrument (2000) but differs as discussed below. Ultrasonic surgical instrument (2400) has another example of a communication port (2404) on distal end cap (2412) and an electrical cable (2402) including an interior cable (2462) and an exterior cable (2464) that are releasably connected at a modular connector (2466). Modular connector (2466) mechanically and electrically connects interior cable (2462) to exterior cable (2464) and facilitates removal of exterior cable (2464) for sterilization or replacement. Interior cable (2462) extends proximally to carriage (2041) of carrier KART (2008) and connects to carrier KART connector (2054).

FIGS. 45-46 shows carriage (2041) of carrier KART (2008) in the distal position. Electrical cable (2402) includes interior cable (2462) and exterior cable (2464) removably connected by modular connector (2466), which includes a distal coupling (2480) and a proximal coupling (2482) (see FIG. 47). Distal coupling (2480) is electrically and mechanically connected to exterior cable (2464) and proximal coupling (2482) (see FIG. 47) is electrically and mechanically connected to interior cable (2462). Proximal and distal couplings (2482, 2480) thus removably connect these interior and exterior cables (2462, 2464) together as discussed below in greater detail.

Interior cable (2462) includes a helical cable (2470) and carriage (2041) of carrier KART (2008) is shown in the distal position. Helical cable (2470) extends directly from proximal coupling (2482) (see FIG. 47) to carriage (2041) of carrier KART connector (2054) in a compressed state. In the compressed state, gaps (2474) between coils (2472) are relatively small to define a shorter overall defined length in the compressed state relative to an expanded state, which may be similar to expanded state of helical cable (2070) (see FIG. 42A) discussed above. More particularly, with carriage (2041) of carrier KART (2008) in the proximal position, helical cable (2470) elongates in the expanded state to straighten coils at least partially (2472) such that gaps (2474) are relatively larger in the expanded state.

Figure 47:
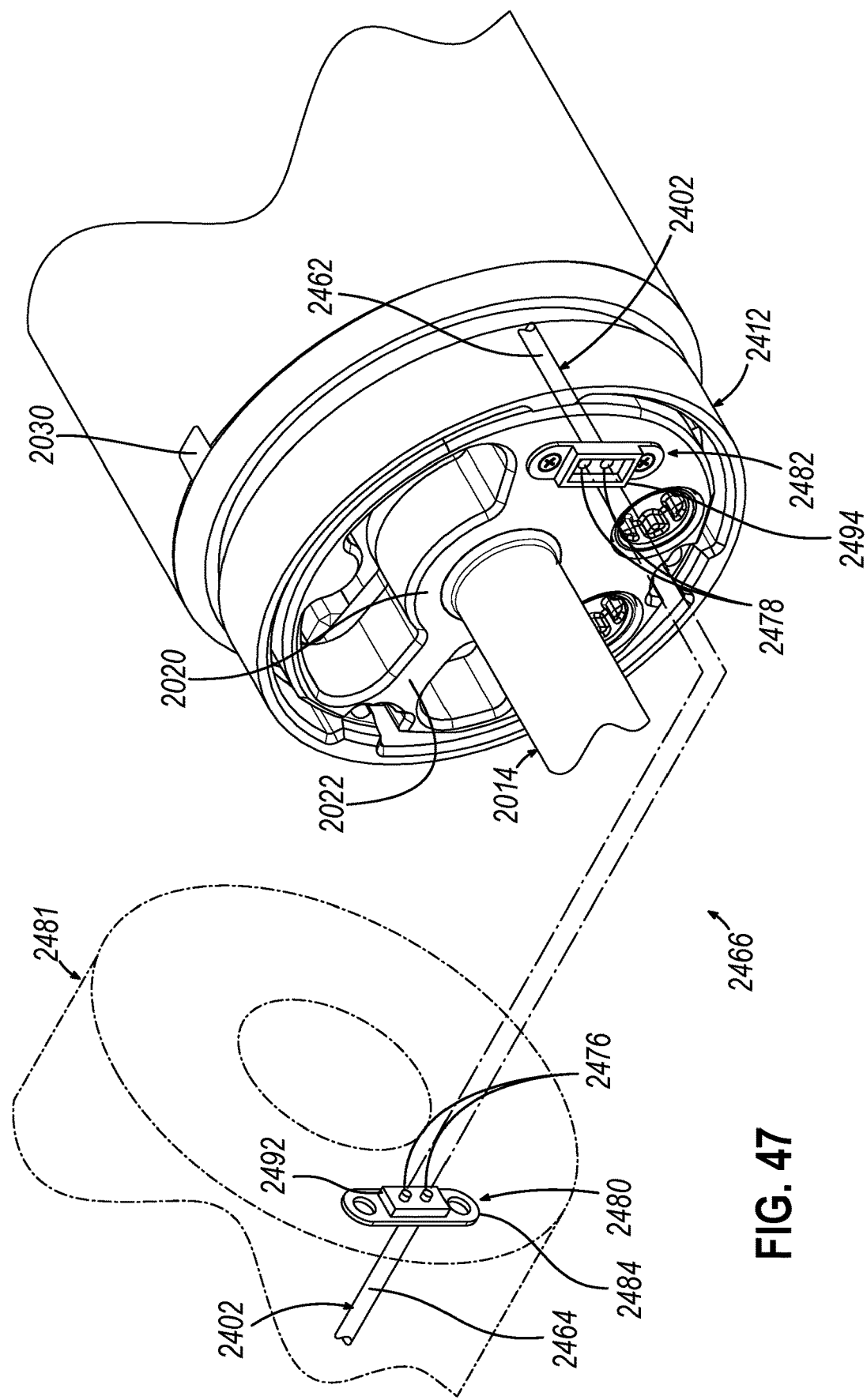
FIG. 47 depicts an enlarged, partially exploded section view of the modular connector shown in FIG. 16.

FIGS. 46-47 show a sterile adapter (2481) configured to connect at distal end cap (2412) via modular connector (2466) such that electrical cable (2402) effectively passes through a sterile field in use, although it will be appreciated that modular connector (2466) may be used at any ports discussed herein for removable connections. To this end, modular connector (2466) includes distal and proximal couplings (2480, 2482), which respectively have prong members (2476) and receptacles (2478) in the present example. Prong members (2476) electrically connect to exterior cable (2464), whereas receptacles (2478) electrically connected to interior cable (2462). Receptacles (2478) are configured to removably receive prong members (2470) thereagainst to communicate electrical power and/or data therethrough for electrical communication between interior and exterior cables (2462, 2464) while connected.

Distal and proximal couplings (2480, 2482) respectively include distal and proximal bodies (2484, 2482) constructed of a non-conductive material such as plastic, and respectively support prong members (2476) and receptacles (2478) thereon. Distal body (2484) has a first raised portion (2492) that encircles prong members (2470). Proximal connector (2482) has a second raised portion (2494) that fits around first raised portion (2492) to releasably retain securement between prong members (2476) and receptacles (2478). For example, first and second raised portions (2492, 2494) have an interference fit for frictional engagement therebetween. Alternatively or in addition, this interference fit may be caused by a barb (not shown) that corresponds with a recess (not shown) sized to grip barb. Modular connector (2466) may additionally include latches (not shown) to aid joining and retaining distal and proximal couplings (2480, 2482).

VI. CARRIER KART AND DRIVE HOUSING WITH CABLE GUIDE

In some instances, it may be desirable for any of surgical instruments (14, 2000, 2100, 2200, 2300, 2400) to include one or more active cable management features to further guide cables during use. Even self-managing cables, such as those discussed above, may benefit from additional guidance during use in some instances to further inhibit chaffing, tangling, or tearing. Thus, an active cable management system is configured to inhibit such chaffing, tangling, or tearing of one or more cables during use.

Another exemplary ultrasonic surgical instrument (2500) with an active cable management system, such as a cable guide (2502), is described below with respect to FIGS. 48A-48B and may be incorporated into table based robotic systems (10, 28) described above. To this end, a drive housing (2506) of ultrasonic surgical instrument (2500) is configured to attach to robotic arm (32) as discussed above. Ultrasonic surgical instrument (2500) further includes electrical cable (2002) statically attached at drive housing (2506), although any such cable described herein may be similarly used.

FIG. 48A shows ultrasonic surgical instrument (2500) similar to ultrasonic instrument (2000) with carriage (2541) of carrier KART (2508) located in a distal position fitted with an active cable management system in the form of a cable guide (2502). Cable guide (2502) includes a plurality of chain links (2504) pivotally coupled to each other in succession from a first end (2510) to a second end (2512). First end (2510) has a first link (2514) fixedly coupled with a proximal portion of drive housing (2506) and second end (2512) has a second link (2516) fixedly coupled with carriage (2541) of carrier KART (2508). First and second links (2514, 2516) may be secured in position with bolts, rivets, welds, or generally any method of securement for fixing one or both of chain links (2514, 2516) relative to a structure.

Each of chain links (2504) includes a channel (2518), a pair of pins (2520), and a pair of apertures (2522). Channel (2518) is configured to receive electrical cable (2002) through chain links (2504). Apertures (2522) are configured to laterally receive pins (2520) and facilitate the coupling together of chain links (2504). The coupled apertures and pins (2522, 2520) also facilitate the rotational movement of chain links (2504) in an arcuate path to create a loop (2524) when carriage (2041) of carrier KART (2508) is moved longitudinally. Chain links (2504) extend distally and form loop (2524) that proximally directs chain links (2504) to carriage (2041) of carrier KART (2508) where second link (2516) is secured to carrier KART (2508). Cable guide (2502) defines a predetermined path and receives electrical cable (2002) along the predetermined path such that cable guide (2502) is configured to retain electrical cable (2002) along the predetermined path as ultrasonic transducer assembly (2056) selectively moves from the proximal, retracted position to the distal, extended position. Cable guide (2502) also retains electrical cable (2002) within channel (2518) during rotation of ultrasonic surgical instrument (2500), such as during rotation by robotic arm (32).

FIG. 48B shows ultrasonic surgical instrument with carriage (2541) of carrier KART (2508) translated to the proximal position. During such translation, cable guide (2502) bends in a proximal direction as loop (2524) advances through chain links (2504) making a distally extending portion of chain links (2504) shorter relative to distally extending portion of chain links (2504) with carriage (2541) in the distal position (see FIG. 48A). A proximally extending portion of chain links (2504) that extends from loop (2524) to carriage (2541) of carrier KART (2508) becomes longer relative to the proximally extending portion of chain links (2504) with carriage (2541) in the distal position (see FIG. 48A).

VII. FLEX CIRCUIT WITH VARIOUS MOUNTINGS

In some instances, it may be desirable to provide another example of a carrier KART (2600) with a carriage (2641) incorporated into any of ultrasonic surgical instruments (14, 2000, 2100, 2200, 2300, 2400, 2500) discussed above. For example, ultrasonic transducer assembly (2056) is generally in electrical communication with a generator (not shown) and controller (not shown) to respectively provide and actuate electrical communication with ultrasonic transducer assembly (2056). A circuit that controls ultrasonic transducer assembly (2056) may be advantageous in some examples for reducing or eliminating one or more cables and/or providing alternative access to manually actuate electrical communication.

A. Flex Circuit Mounted to Carrier KART

Figure 49:
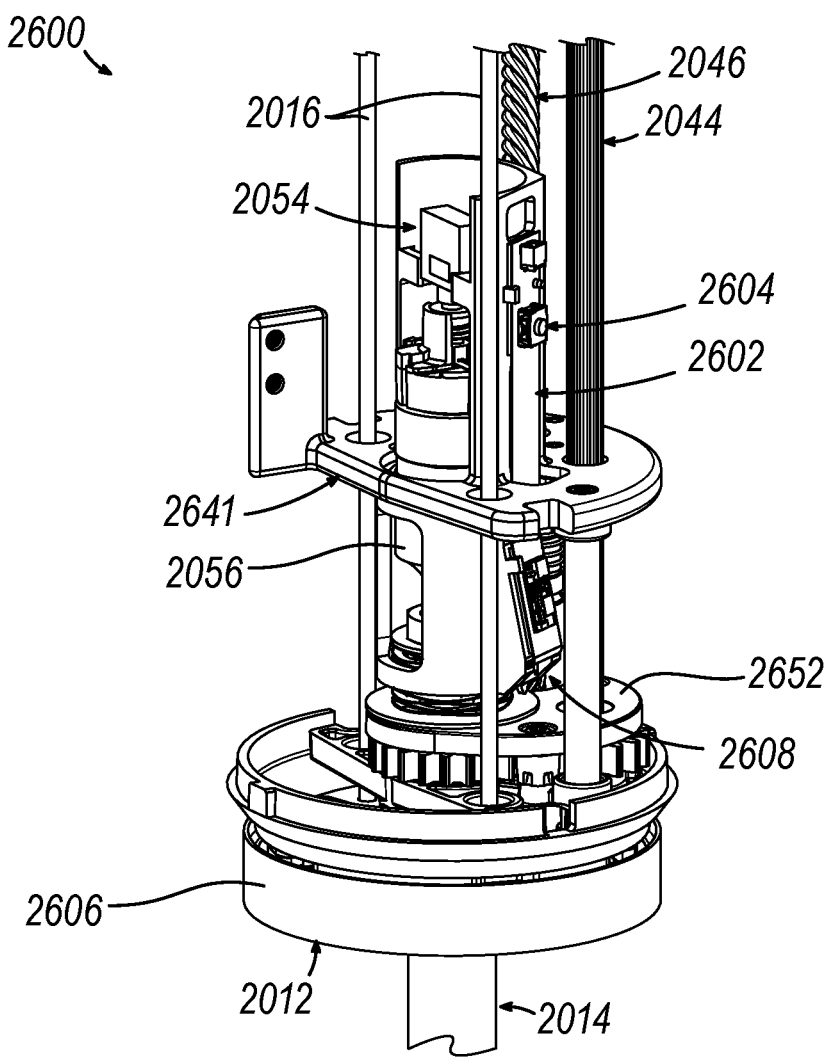
FIG. 49 depicts an enlarged perspective view of an alternative example of a carriage of a carrier KART fitted with a flex circuit.
Figure 50:
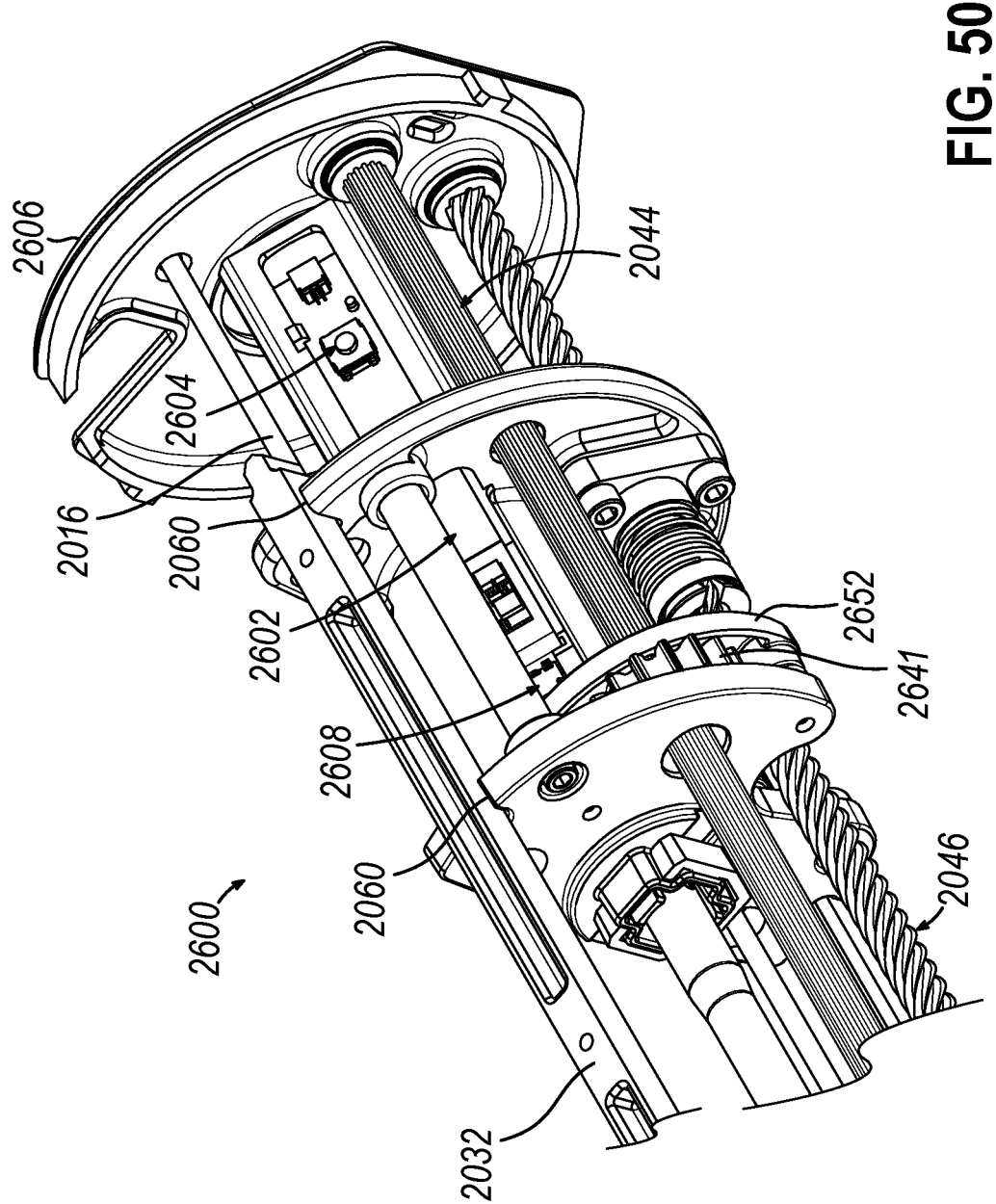
FIG. 50 depicts an enlarged perspective view of the carriage of the carrier KART of FIG. 49.

FIGS. 49-50 show carrier KART (2600) similar to carrier KART (2008) but including a flex circuit (2602) fixedly mounted to carriage (2641) of carrier KART (2600). Flex circuit (2602) is affixed to carriage (2641) of carrier KART (2600) and administers electricity to ultrasonic transducer assembly (2056) to thereby reduce associated complex wiring between remotely located sensors (not shown) and circuits (not shown) within carrier KART (2600) and end effector (116).

To this end, flex circuit (2602) includes a manual activation switch (2604) and a closure switch (2608). Flex circuit (2602) may also include other electronic features such as relays and sensors that are configured to provide feedback or activate additional features located on end effector (116).

Flex circuit (2602) is mounted onto carriage (2641) of carrier KART (2600) proximate to ultrasonic transducer assembly (2056) within drive housing (2606). Manual activation switch (2604) is configured to manually allow electricity to be supplied to ultrasonic transducer assembly (2056) and further supplied to ultrasonic blade (146). A drive housing (2606) may further include a bore (not shown), recess (not shown), or cutout (not shown) to allow an operator to access manual activation switch (2604) from outside of drive housing (2606). Additionally, manual activation switch (2604) may include additional pliable covers (not shown) or linkages (not shown) to allow selective access as desired.

In one example, closure switch (2608) is operatively connected to end effector (116) and receives feedback to operatively close closure switch (2608) when clamping force is achieved. Closure switch (2608) of the present example is closed by closure switch (2608) engaging a portion of frame (2652) when a predetermined clamping force is achieved. Closure switch (2608) sends feedback to flex circuit (2602) or controller to control the clamping force of end effector (116). Additionally, closure switch (2608) may send feedback to flex circuit (2602) or controller to increase or decrease the ultrasonic energy supplied to ultrasonic blade (146). Flex circuit (2602) may include circuits (not shown) or relays (not shown) that allow additional feedback to the user, or activate additional features located on end effector (116).

B. Flex Circuit Fitted to Proximal End Cap

Figure 51:
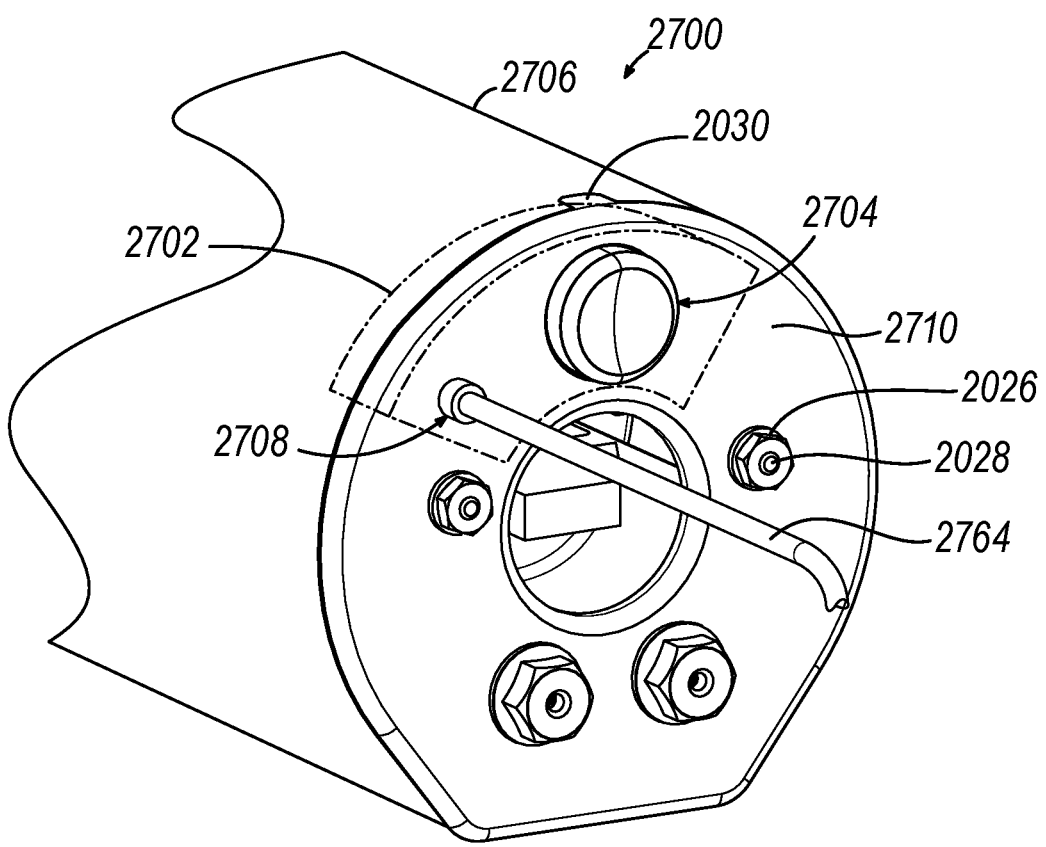
FIG. 51 depicts an enlarged perspective view of an alternative example of a housing fitted with a cord plug and a manual activation switch.

FIG. 51 shows another exemplary ultrasonic surgical instrument (2700) including a drive housing (2706) fitted with a flex circuit (2702). Flex circuit (2702) differs from flex circuit (2602) (see FIG. 50) in that flex circuit (2702) is fixedly mounted to a distal face of a proximal end cap (2710) and does not translate with carriage (2041) (see FIG. 39) of carrier KART (2008) (see FIG. 39). Flex circuit (2702) includes a manual activation switch (2704) that is accessible from outside of drive housing (2706) and maintains the same position relative to drive housing (2706) as carriage (2041) of carrier KART (2008) moves from the proximal position to the distal position. Flex circuit (2702) further includes a connection port (2708) configured to removably couple exterior cable (2764). Flex circuit (2702) may include other electronic features such as relays and sensors that are configured to provide feedback, or activate additional features located on end effector (116).

VIII. EXEMPLARY SURGICAL INSTRUMENT WITH SENSOR FEEDBACK

In some instances, it may be desirable to provide feedback relative to various operating conditions at a distal end of surgical instrument (14) (see FIG. 5). For instance, one or more sensors can be incorporated into surgical instrument (14) (see FIG. 5) that are configured to measure one or more operating conditions at a distal end of surgical instrument (14) (see FIG. 5), such as a position or angle of clamp arm (144) (see FIG. 7A) relative to blade (146) (see FIG. 7A), a force exerted on clamp arm (144) (see FIG. 7A) and/or blade (146) (see FIG. 7A), a temperature, tissue stiffness, and various other tissue conditions. The data measured by the one or more sensors can be transmitted and displayed by table-based robotic system (10) (see FIG. 1) to allow a user to operate surgical instrument (14) (see FIG. 5) based on the measured data for improved control of surgical instrument (14) (see FIG. 5).

A. Exemplary Clamping Sensor Feedback

Figure 52:
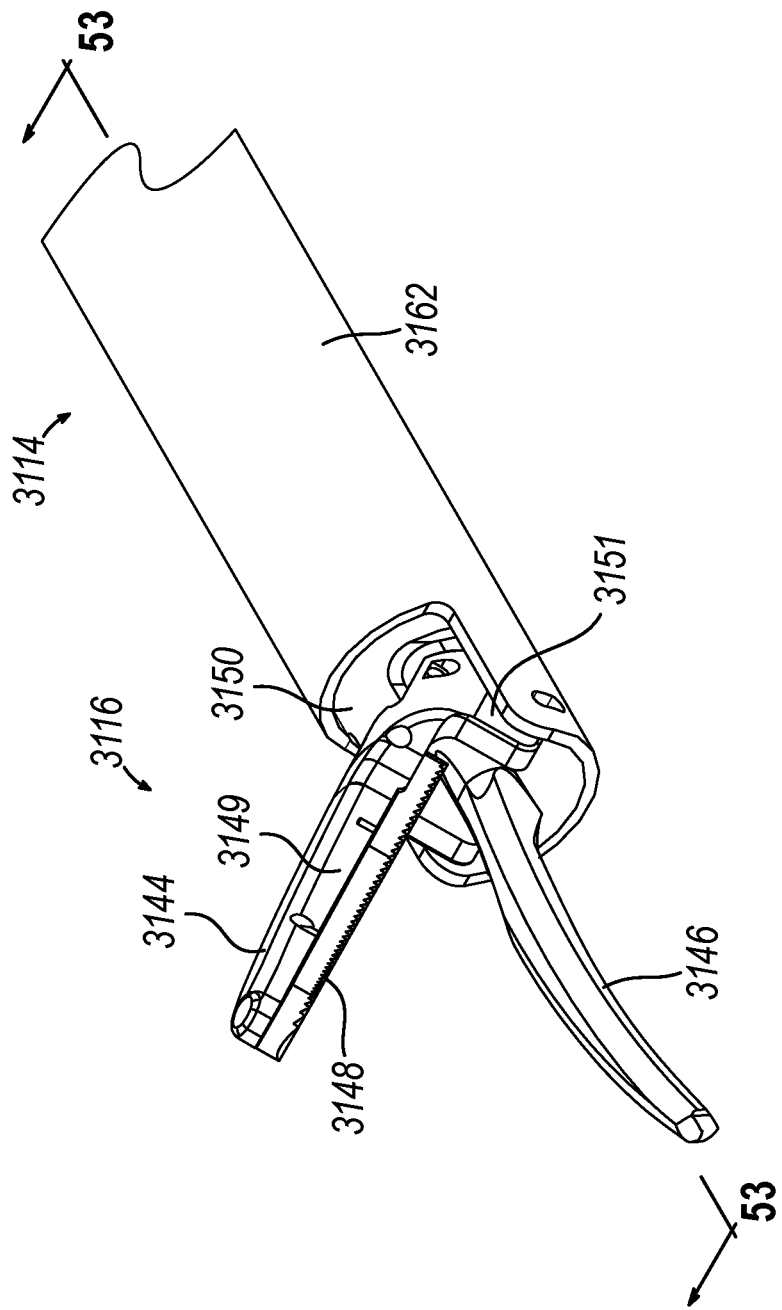
FIG. 52 depicts an enlarged perspective view of another exemplary end effector and shaft assembly for use with the surgical instrument of FIG. 5.
Figure 53:
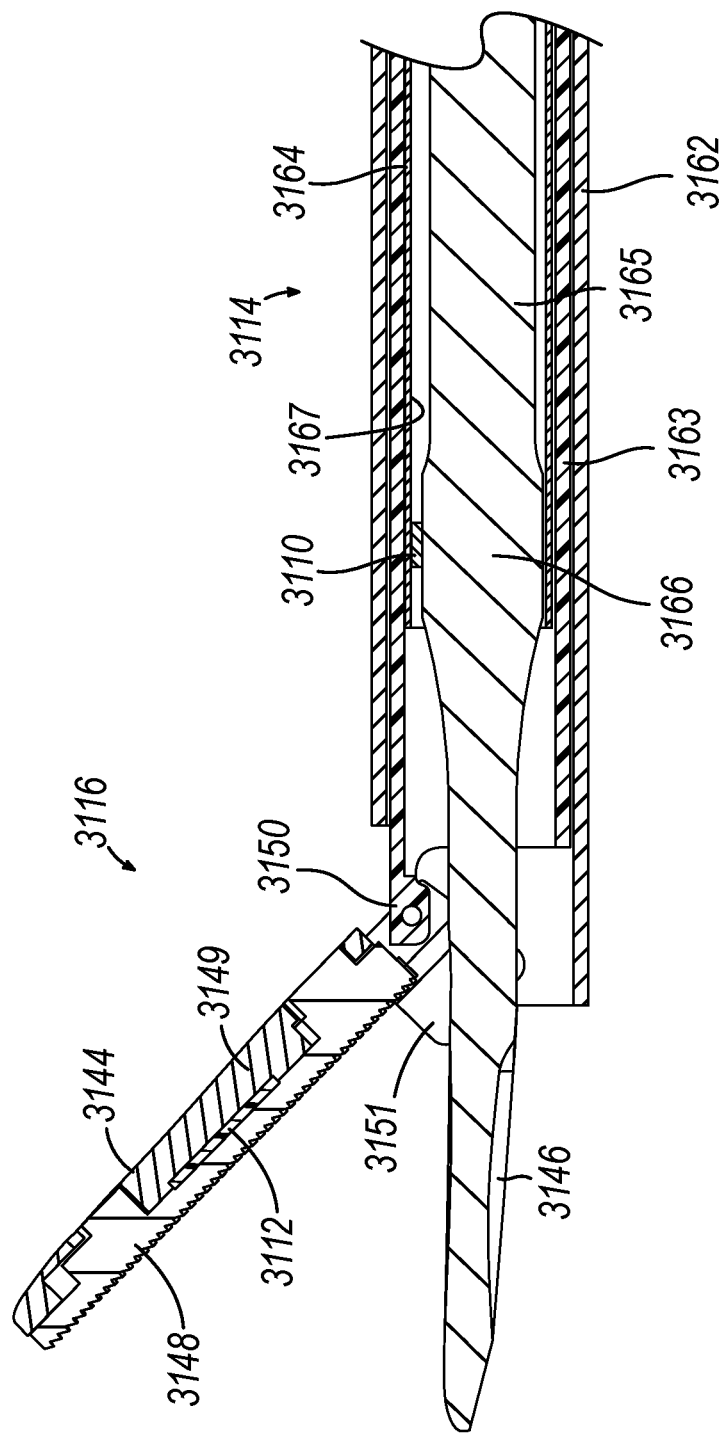
FIG. 53 depicts an enlarged cross-sectional view of the end effector and shaft assembly of FIG. 52 taken along section line 53-53 of FIG. 52.

FIGS. 52-53 show an exemplary end effector (3116) and a shaft assembly (3114) that can be incorporated into surgical instrument (14) (see FIG. 5) described above to provide feedback relative to various conditions at a distal end of surgical instrument (14) (see FIG. 5) such that like numbers below indicate like features discussed above in greater detail. End effector (3116) is similar to end effector (116) (see FIG. 7A) described above except that end effector (3116) includes sensors (3110, 3112). For instance, end effector (3116) includes a clamp arm (3144) and an ultrasonic blade (3146). Clamp arm (3144) has a clamp pad (3148) and an arm body (3149) such that the clamp pad is secured to an underside of arm body (3149), facing blade (3146). Clamp arm (3144) is pivotally secured to a distally projecting tongue (3150) of an inner tube (3163) of shaft assembly (3114). Shaft assembly (3114) further includes an outer tube (3162) that slidably receives inner tube (3163) as well as a sheath (3164) positioned coaxially within inner tube (3163) that coaxially receives an acoustic waveguide (3165). Sheath (3164) of the present example is formed from a polytetrafluoroethylene (PTFE) material for damping vibrations to inhibit damage to tubes (3162, 3163) as well as other portions of surgical instrument (14), although other materials for inhibiting such damage may be similarly used. Clamp arm (3144) is operable to selectively pivot toward and away from blade (3146) to selectively clamp tissue between clamp arm (3144) and blade (3146). A pair of arms (3151) extend transversely from clamp arm (3144) and are pivotally secured to an outer tube (3162) of shaft assembly (3114). Thus, inner tube (3163) is configured to longitudinally slide relative to outer tube (3162) to pivot clamp arm (3144) between a closed position and an open position. In some other versions, outer tube (3162) may be configured to slide relative to inner tube (3163) to pivot clamp arm (3144). Blade (3146) of the present example is operable to vibrate at ultrasonic frequencies in order to effectively cut through and seal tissue, particularly when the tissue is being compressed between clamp pad (3148) and blade (3146).

End effector (3116) of the present example further comprises one or more sensors (3110, 3112) for providing feedback of one or more conditions at the distal end of surgical instrument (14). For instance, sensors (3110, 3112) can be used to measure one or more of a position or angle of clamp arm (3144) relative to blade (3146), a force exerted on clamp arm (3144), a temperature, and various tissue conditions. Sensors (3110, 3112) can include one or more of a pressure sensor (e.g., a pressure transducer, a pressure transmitter, a piezometer, a manometer, a strain gage, an optical sensor, etc.), a linear travel sensor (e.g., a linear transducer, a potentiometer, an linear variable differential transformer, a hall effect sensor, etc.), and a temperature sensor (e.g., a thermocouple, a resistance temperature detector, a thermistor, etc.). Accordingly, a pressure sensor can be configured to detect a closure force between clamp arm (3144) and blade (3146) and/or a linear travel sensor can be configured to detect a position or angle between clamp arm (3144) and blade (3146). The closure force and/or clamp position feedback can improve hemostasis and/or to provide a safety mechanism to ensure end effector (3116) is sufficiently closed prior to ultrasonic energy being applied by blade (3146). A temperature sensor can be configured to detect a temperature at a distal end of surgical instrument (14) (see FIG. 5). This temperature feedback can indicate whether end effector (3116) exceeds a predetermined temperature limit, which may mitigate failures of end effector (3116).

In the illustrated version, a first sensor (3110) is positioned between sheath (3164) and an annular flange (3166) of waveguide (3165). For instance, first sensor (3110) is attached to an upper interior surface (3167) of sheath (3164) such that first sensor (3110) is proximally positioned from clamp arm in the longitudinally proximal direction and thus longitudinally aligned with clamp arm (3144). In addition, first sensor (3110) is positioned on annular flange (3166), such as a distal-most annular flange (3166), so as to be laterally aligned in a transverse direction with a node position of waveguide (3165). First sensor (3110) can be attached to sheath (3164) such as by an adhesive, a fastener, or other suitable configuration for securing first sensor (3110) to sheath (3164). In another example, one or more portions of first sensor (3110) are 3D printed to sheath (3164) as to as be formed with sheath (3164) A second sensor (3112) is shown positioned between clamp arm (3144) and clamp pad (3148). Second sensor (3112) can be attached to clamp arm (3144) and then clamp pad (3148) can be mounted over second sensor (3112). Second sensors (3112) can be attached to clamp arm (3144) such as by an adhesive, a fastener, or other suitable configuration for securing second sensor (3112) to clamp arm (3144) and/or clamp pad (3148). In another example, one or more portions of second sensor (3112) are 3D printed to clamp arm (3144) and/or clamp pad (3148) so as to as be formed with at least one of clamp arm (3144) and/or clamp pad (3148).

In some versions, first and second sensors (3110, 3112) include the same type of sensor such that first and second sensors (3110, 3112) are configured to measure the same type of condition (e.g., pressure, displacement, temperature, etc.). In some versions, first and second sensors (3110, 3112) differ from each other such that first and second sensors (3110, 3112) are configured to measure different types of condition (e.g., pressure, displacement, temperature, etc.). In some versions, one of first and second sensors (3110, 3112) can be omitted such that end effector (3116) includes one of first and second sensors (3110, 3112). Moreover, while one of each of first sensor (3110) and second sensor (3112) are shown in the illustrated version, any suitable number of sensors (3110, 3112) can be positioned in any suitable portion of end effector (3116) and/or shaft assembly (3114). Still other suitable configurations for sensors (3110, 3112) will be apparent to one with ordinary skill in the art in view of the teachings herein.

Figure 54:
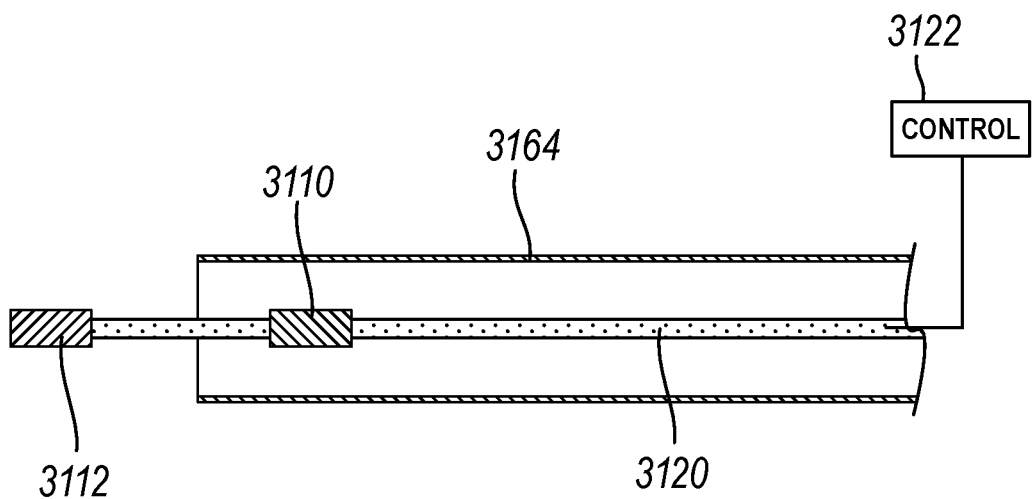
FIG. 54 depicts a sectional underside view of a sheath of the shaft assembly of FIG. 52, showing a coupling between sensors of the end effector and a control.

Referring to FIGS. 53 and 54, a coupling (3120) is shown extending between first and second sensors (3110, 3112) and a control (3122) such that coupling (3120) is configured to electrically couple first and second sensors (3110, 3112) with control (3122). Coupling (3120) is thereby configured to transmit data measured by first and second sensors (3110, 3112) to control (3122). Control (3122) is configured to receive, store, and/or analyze data received from sensors (3110, 3112). Coupling (3120) can include an electrical circuit, a wire, and/or a flat wire for coupling first and second sensors (3110, 3112) to control (3122). In addition, coupling (3120) may be secured to sheath (3164) such as by an adhesive, a fastener, or other suitable configuration for securing coupling to sheath (3164). In another example, one or more portions of coupling (3120) are 3D printed to sheath (3164) so as to as be formed with sheath (3164). Additionally or alternatively, blade (3146) and/or waveguide (3165) can be used to electrically transmit data from sensors (3110, 3112). Still other suitable configurations for transmitting data from sensors (3110, 3112) will be apparent to one with ordinary skill in the art in view of the teachings herein.

Figure 55:
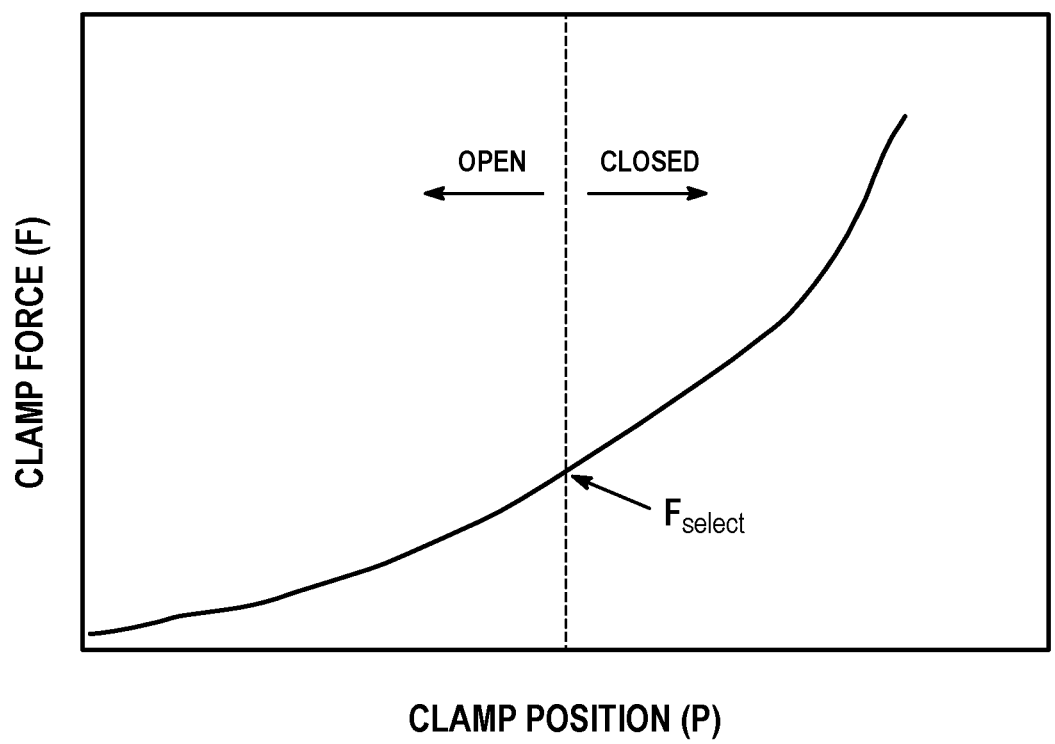
FIG. 55 depicts a graph of a clamp force relative to a clamp position of the end effector of FIG. 52.

Sensors (3110, 3112) can thereby provide real-time feedback on various data inputs at end effector (3116) that can be used to improve performance of surgical instrument (14) (see FIG. 5). Referring to FIGS. 53 and 55, a graph is shown of a clamp force (F) between clamp arm (3144) and blade (3146) relative to clamp position (P), such as the position of clamp arm (3144) relative to blade (3146). As illustrated, clamp force (F) increases as clamp position (P) increases when clamp arm (3144) is moved toward blade (3146). When clamp position (P) is moved such that clamp force (F) reaches a predetermined force ($F_{select}$), end effector (3116) is determined to have moved from an open position (see FIG. 7B) to a closed position (see FIG. 7A). Such a predetermined clamp force value ($F_{select}$) can include a particular level or a range of values to accommodate for noise of sensors (3110, 3112) and/or minor movements of clamp arm (3144). Accordingly, measuring clamp force (F) with one or more sensors (3110, 3112) can be used to drive the position of clamp arm (3144) based on the measured clamp force (F).

Figure 56:
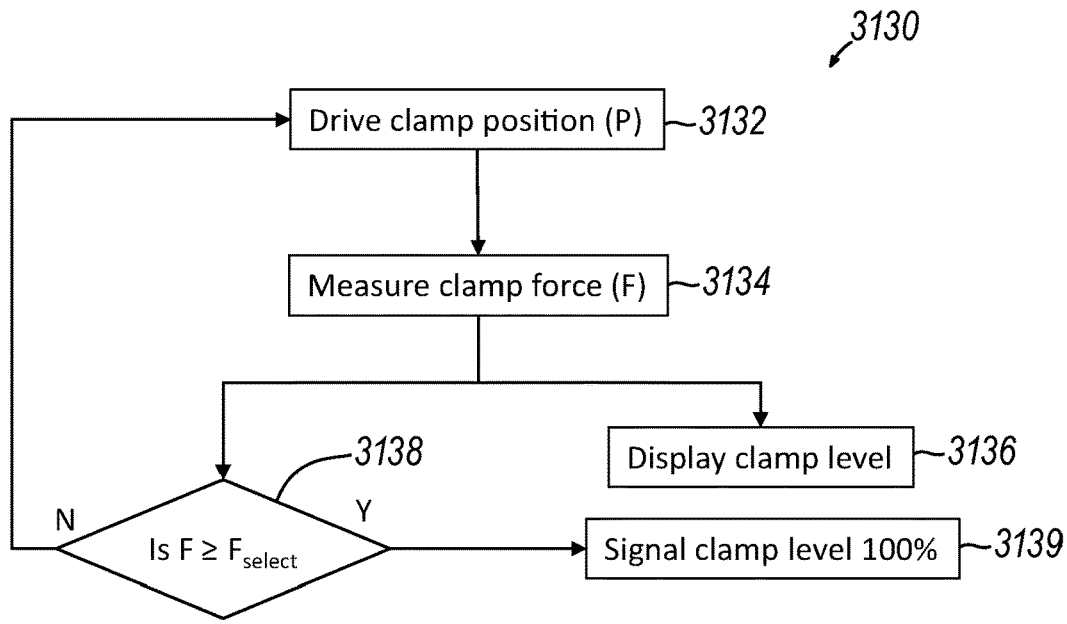
FIG. 56 depicts a flowchart of a method of providing feedback of the clamp position of the end effector of FIG. 52.
Figure 57:
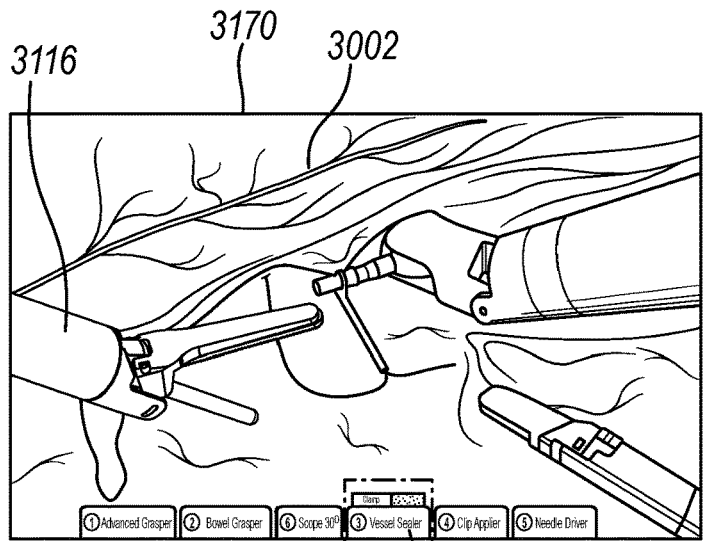
FIG. 57 depicts a schematic view of a user interface for displaying the clamp position of the end effector of FIG. 52.
Figure 57A:
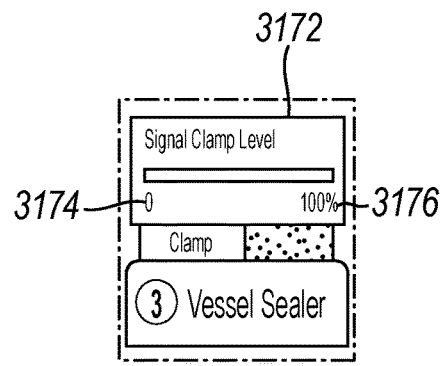
FIG. 57A depicts an enlarged schematic view of a graphic of the user interface of FIG. 14 encircled in FIG. 57.

Referring to FIGS. 53 and 56, an exemplary method (3130) is shown for providing feedback relative to the measured clamp force (F) by first and/or second sensors (3110, 3112) to drive clamp position (P). As clamp arm (3144) is driven relative to blade (3146) (step (3132)), sensors (3110, 3112) measure clamp force (F) between clamp arm (3144) and blade (3146) (step (3134)). This measured clamp force (F) can be displayed (step (3136)), as will be discussed in more detail below. The measured clamp force (F) can then be compared with the predetermined force ($F_{select}$) to determine whether end effector (3116) is in an open position or a closed position (step (3138)). If the measured clamp force (F) is less than the predetermined force ($F_{select}$), end effector (3116) is determined to be in an open position. The clamp position (P) can thereby continue to be driven. If clamp force (F) is greater than or equal to the predetermined force ($F_{select}$), end effector (3116) is determined to be in the closed position. When end effector (3116) reaches the closed position such that the measured clamp force (F) is greater than or equal to the predetermined force ($F_{select}$), a clamp force (F) of 100% can be displayed to indicate that end effector (3116) is closed (step (3139)). The clamp position (P) can thereby stop being driven, such as by control (3122) and/or user input.

Referring to FIGS. 53, 56, 57 and 57A, an exemplary user interface (3170) is shown for displaying data measured by sensors (3110, 3112). In the illustrated version, user interface (3170) includes a screen displaying end effector (3116) during operation, such as relative to tissue (3002). User interface (3170) further includes a graphic (3172) for displaying clamp force (F) to provide feedback to the user of the clamp force (F) for operating end effector (3116). In the illustrated version, graphic (3172) is positioned on a bottom portion of interface (3140) along a toolbar, but any other suitable configuration can be used. Graphic (3172) of the illustrated version includes a display of clamp force level (3174) configured to display the real-time measured clamp force (F) transmitted by sensors (3110, 3112) and a clamp force level percentage (3176) configured to display a percentage of the closure of clamp arm (3144). For instance, 0% may correspond to a fully open position and 100% may correspond to a fully closed position. Still other suitable configurations for graphic (3172) will be apparent to one with ordinary skill in the art in view of the teachings herein.

Accordingly, referring to FIGS. 52-57A, the feedback provided by sensors (3110, 3112) can be used to drive clamp position (P) of end effector (3116). For instance, the user may position end effector (3116) relative to tissue (3002) to be cut and/or sealed in the open position. Sensors (3110, 3112) can measure clamp force (F) in real time. In the open position, the measured clamp force (F) is less than the predetermined force ($F_{select}$) such that graphic (3172) can display the measured clamp force level (3174) and/or that the clamp force percentage (3176) as 0% to indicate that end effector (3116) is in the fully open position. Once end effector (3116) is in the desired position, the user and/or control (3122) can drive clamp position (P) to close clamp arm (3144) relative to blade (3146) to clamp tissue (3002) therebetween. While closing end effector (3116), sensors (3110, 3112) can measure clamp force (F). As end effector (3116) moves toward the closed position, interface (3170) can display the measured clamp force level (3174) and/or the clamp force percentage (3176) as increasing from 0% toward 100%. The measured clamp force (F) can then be compared with the predetermined force ($F_{select}$). The user and/or control (3122) can continue to drive clamp position (P) until the measured clamp force (F) becomes greater than or equal to the predetermined force ($F_{select}$). Graphic (3172) can thereby indicate the measured clamp force level (3174) and/or the clamp force percentage (3176) has reached 100% such that end effector (3116) is in the closed position. With end effector (3116) in the closed position, the user can apply ultrasonic energy with blade (3146) to cut and/or seal tissue (3002). Clamp position (P) can be driven to return end effector (3116) to the open position. In opening end effector (3116), the measured clamp force (F) can be compared with the predetermined force ($F_{select}$) to indicate when the measured clamp force (F) is less than the predetermined force ($F_{select}$). Graphic (3172) can display that the measured clamp force level (3174) and/or clamp force percentage (3176) is less than 100% such that end effector (3116) is in the open position. Still other suitable methods for operating end effector (3116) based on feedback from sensors (3110, 3112) will be apparent to one with ordinary skill in the art in view of the teachings herein.

For instance, a similar method can be used to control clamp position (P) based on measured clamp position and/or measured temperature. For instance, a clamp position (P) measured by sensors (3110, 3112) can be compared with a predetermined clamp position (P) to determine whether clamp arm (3144) is open or closed relative to blade (3146). Additionally or alternatively, a temperature measured by sensors (3110, 3112) can be compared with a predetermined temperature to determine whether a temperature of end effector (2116) has exceeded an operating limit. Such clamp position (P) and/or temperature can be displayed by a graphic (3172) on interface (3170).

B. Exemplary Non-Clamping Sensor Feedback

Figure 58:
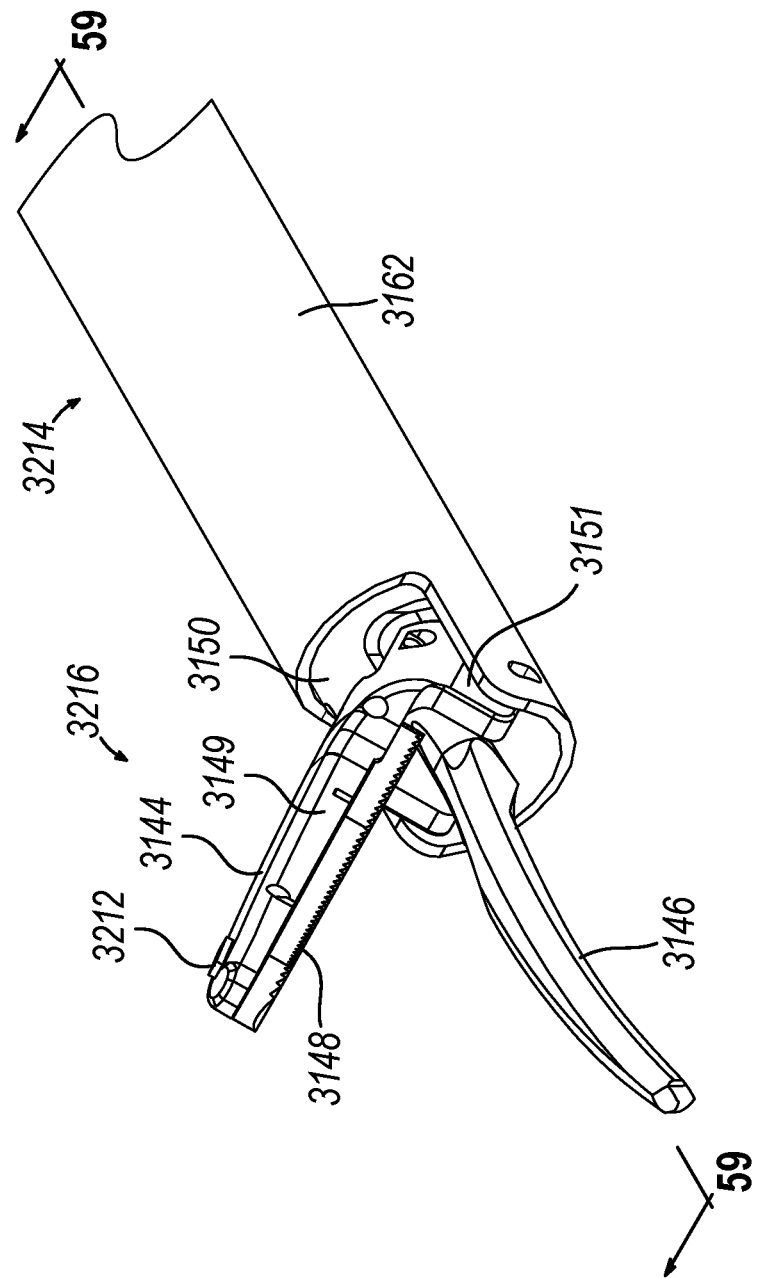
FIG. 58 depicts an enlarged perspective view of another exemplary end effector and shaft assembly for use with the surgical instrument of FIG. 5.
Figure 59:
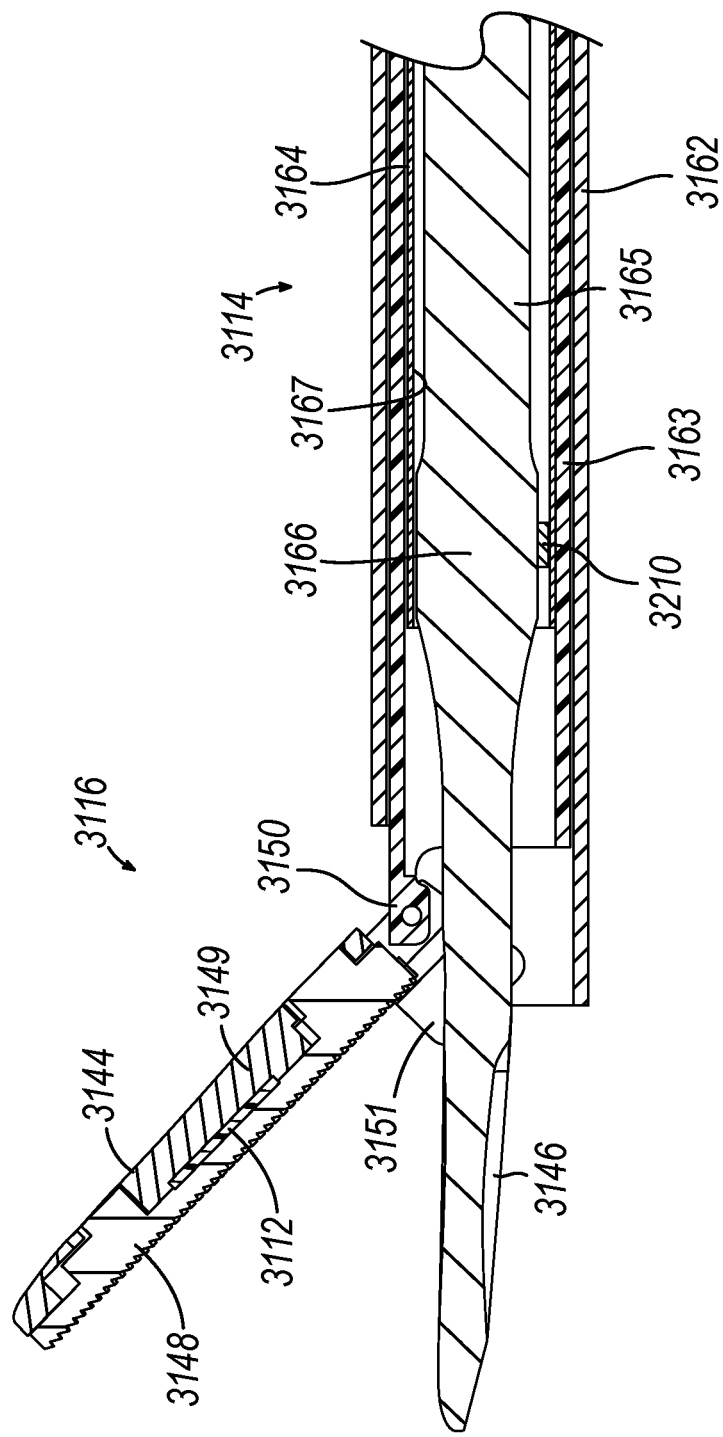
FIG. 59 depicts an enlarged cross-sectional view of the end effector and shaft assembly of FIG. 58 taken along section line 59-59 of FIG. 58.

FIGS. 58-59 show another exemplary end effector (3216) and shaft assembly (3214) that may be incorporated into surgical instrument (14) (see FIG. 5) described above to provide feedback relative to various conditions at a distal end of surgical instrument (14) (see FIG. 5), such as non-clamping tissue loads and/or stiffness of the tissue. In this respect, like numbers below indicate like features discussed above in greater detail. To this end, end effector (3216) and shaft assembly (3214) is similar to end effector (3116) (see FIG. 52) and shaft assembly (3114) (see FIG. 52) described above except that end effector (3216) and shaft assembly (3214) include sensors (3210, 3212) positioned at different portions of end effector (3216) and shaft assembly (3214). In the illustrated version, a first sensor (3210) is positioned between sheath (3164) and annular flange (3166) of waveguide (3165). For instance, first sensor (3210) is attached with interior surface (3167) of sheath (3164) on an underside of waveguide (3165) laterally opposite from clamp arm (3144) such that first sensor (3210) is aligned with annular flange (3166) of waveguide (3165) at a node position of blade (3146). A second sensor (3212) is shown positioned on an exterior surface of clamp arm (3144), such as a top portion of clamp arm (3144) away from blade (3146). First and second sensors (3210, 3212) can be attached to sheath (3164) and/or clamp arm (3144) by any suitable configuration, such as by 3D printing, adhesive, fasteners, etc. First and second sensors (3210, 3212) can be electrically coupled with control (3122) (see FIG. 54), such as by a coupling (3120) (see FIG. 54), such that sensors (3210, 3212) are configured to transmit data to control (3122) (see FIG. 54). Control (3122) (see FIG. 54) can be configured to receive, store, and/or analyze data received by sensors (3210, 3212). Additionally or alternatively, blade (3146) can be used to electrically transmit data from sensors (3210, 3212).

First and second sensors (3210, 3212) can be configured to measure the same condition or different conditions. In some versions, one of first and second sensors (3210, 3212) can be omitted such that end effector (3216) includes one of first and second sensors (3210, 3212). Moreover, while one of each of first sensor (3210) and second sensor (3212) are shown in the illustrated version, any suitable number of sensors (3210, 3212) can be positioned in any suitable portion of end effector (3216) and/or shaft assembly (3114). Still other suitable configurations for sensors (3210, 3212) will be apparent to one with ordinary skill in the art in view of the teachings herein.

Figure 60:
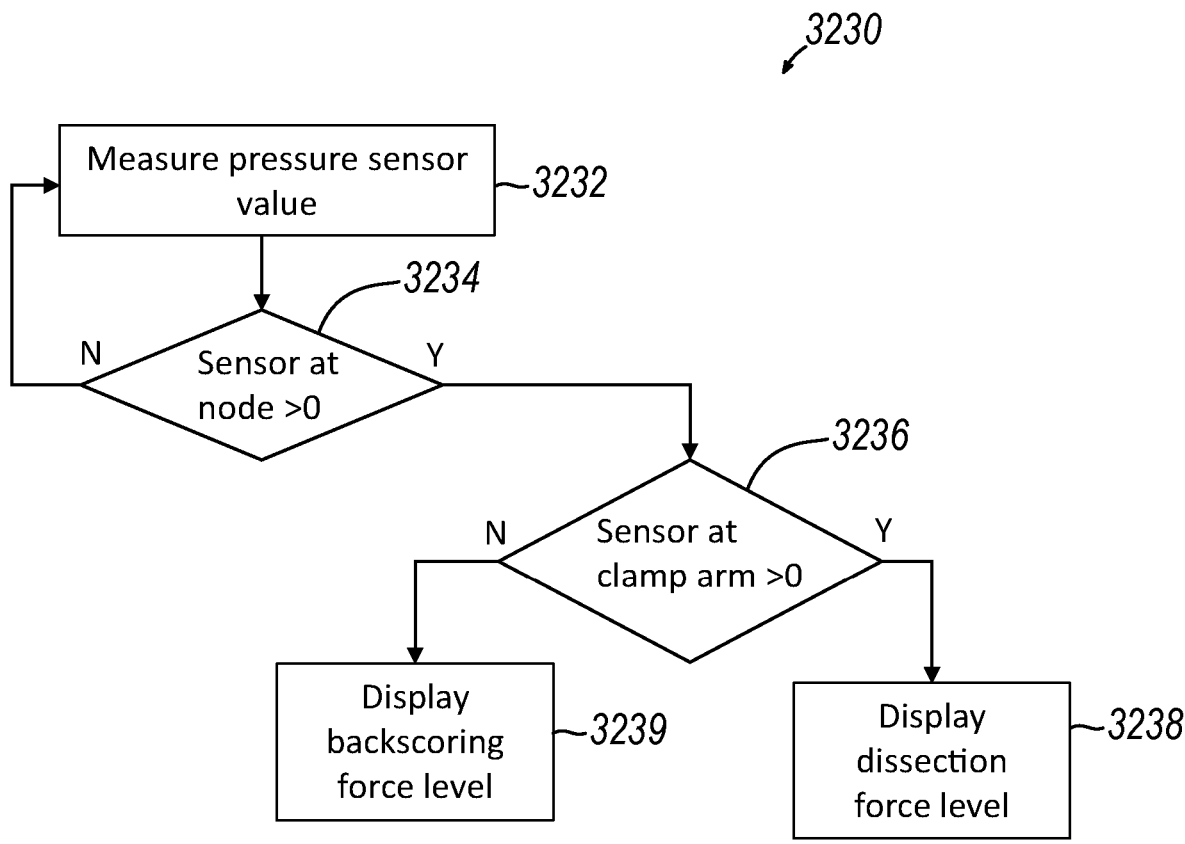
FIG. 60 depicts a flowchart of a method of providing feedback for a pressure value of the end effector of FIG. 58.

In the present example, sensors (3210, 3212) are configured to measure a non-clamping force applied to clamp arm (3144) and/or blade (3146), such as a dissection force when end effector (3216) is used to dissect tissue and/or a backscoring force when end effector (3216) is used to backscore tissue. Sensors (3210, 3212) can include one or more types of pressure sensors (e.g., pressure transducers, pressure transmitters, piezometers, manometers, strain gages, optical sensors, etc). Sensors (3210, 3212) can thereby be used to gain real-time feedback on various data inputs at end effector (3216) (that can be used to improve performance of surgical instrument (14) (see FIG. 5). Referring to FIGS. 59-60, an exemplary method (3232) is shown for providing feedback of the measured pressure sensor value from first and/or second sensors (3210, 3212) to detect non-clamping tissue loads. A pressure value at one or both of first and second sensors (3210, 3212) can be measured by the respective first and second sensors (3210, 3212) (step (3232)). The measured pressure value can be transmitted to control (3122), which may include a microprocessor and a computer memory for analysis and comparison, and can determine whether contact has been made with tissue by end effector (3216). For instance, the measured pressure value by first sensor (3210) at annular flange (3166) can be analyzed to determine whether the measured pressure is greater than 0 (step (3234)). If the measured pressure value is greater than 0, the measured pressure value by second sensor (3212) at clamp arm (3144) can be analyzed to determine whether the measured pressure is greater than 0 (step (3236)). If the measured pressure value is greater than 0, the measured pressure by second sensor (3212) can be displayed as a dissection force level (step (3238)). If the measured pressure value is less than 0, the measured pressure by first sensor (3210) can be displayed as a backscoring force level (step (3239)).

Figure 61:
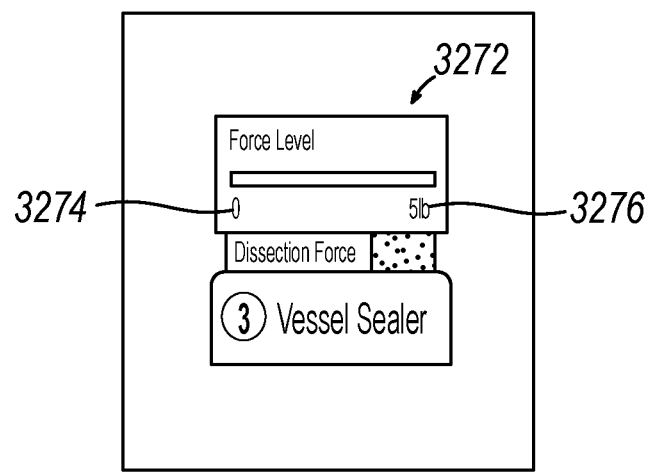
FIG. 61 depicts a schematic view of a graphic for displaying the pressure value of the end effector of FIG. 58.
Figure 63:
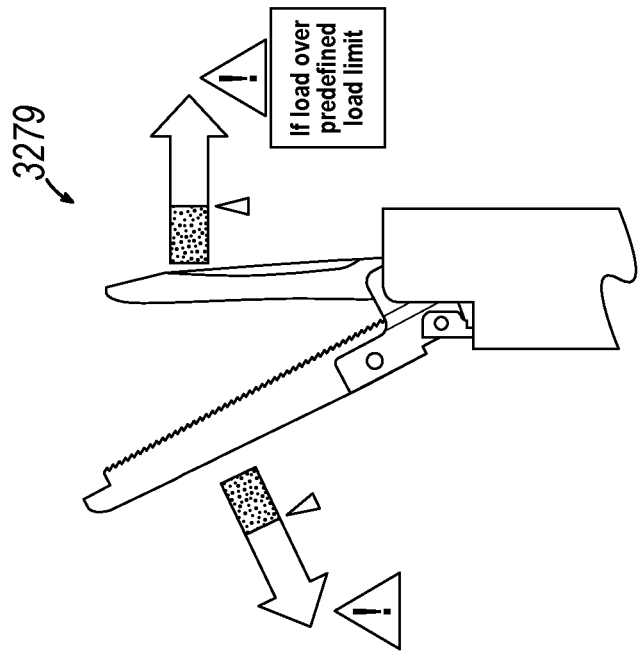
FIG. 63 depicts a schematic view of a second alert for displaying the pressure value of the end effector of FIG. 58.
Figure 62:
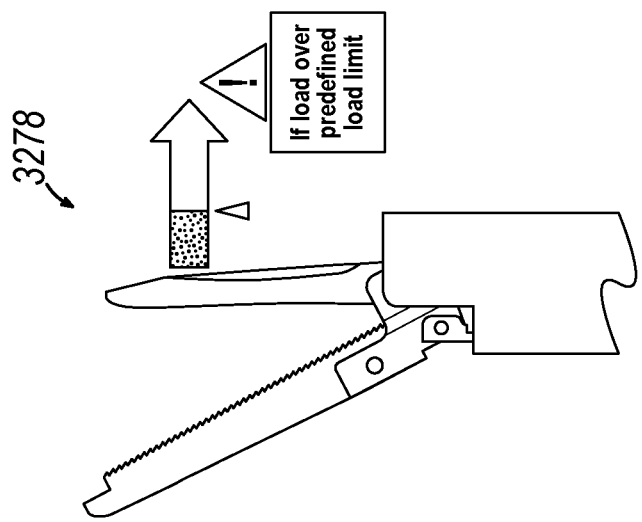
FIG. 62 depicts a schematic view of a first alert for displaying the pressure value of the end effector of FIG. 58.

Referring to FIGS. 59 and 61, an exemplary graphic (3272) is shown that can be incorporated into interface (3170) (see FIG. 57) that is configured to display the real-time measured force level (3274) measured by first and/or second sensors (3210, 3212). In some versions, the respective measured force level (3274) is compared with a predetermined force level limit (3276) to determine whether the respective measured force level (3274) exceeds force level limit (3276). Graphic (3272) of the illustrated version is configured to display force level limit (3276). If the respective measured force level (3274) exceeds force level limit (3274), an alert (3278, 3279) can be displayed on interface (3170) (see FIG. 57) as shown in FIGS. 59, 60, and 62-63. For instance, if the backscoring force level measured by first sensor (3210) exceeds force level limit (3276), a first alert (3278) can be displayed to indicate that the load is above the limit. If the dissection force measured by first and/or second sensors (3210, 3212) exceeds force level limit (3276), a second alert (3279) can be displayed to indicate the load is above the limit. Accordingly, the feedback provided by sensors (3210, 3212) allows the user to operate end effector (3216) based on the pressure measured by first and/or second sensors (3210, 3212) and/or alert the user if the feedback exceeds an operational limit of end effector (3216). Still other suitable methods for providing feedback based on sensors (3210, 3212) will be apparent to one with ordinary skill in the art in view of the teachings herein.

IX. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) an end effector including an ultrasonic blade; (b) a shaft assembly defining a longitudinal axis and proximally extending from the end effector, wherein the shaft assembly includes an acoustic waveguide in acoustic communication with the ultrasonic blade; (c) an ultrasonic transducer assembly proximally extending from and in acoustic communication with the acoustic waveguide; (d) a housing proximally projecting from the shaft assembly such that the ultrasonic transducer assembly is positioned within the housing; (e) a carrier movably supporting the ultrasonic transducer assembly along the longitudinal axis such that the ultrasonic transducer assembly, the acoustic waveguide, and the end effector are configured to collectively move relative to the housing from a proximal, retracted position on the longitudinal axis to a distal, extended position on the longitudinal axis for inserting the ultrasonic blade into a patient; and (f) an electrical cable extending through the housing at a cable port and electrically connected to the ultrasonic transducer assembly, wherein the electrical cable is configured to transmit electrical communication therealong for operating the ultrasonic transducer assembly.

Example 2

The ultrasonic surgical instrument of Example 1, wherein the housing includes a distal end, a proximal end, and a sidewall extending therebetween.

Example 3

The ultrasonic surgical instrument of Example 2, wherein the cable port is positioned on the proximal end of the housing.

Example 4

The ultrasonic surgical instrument of Example 2, wherein the cable port is positioned on the sidewall of the housing.

Example 5

The ultrasonic surgical instrument of Example 2, wherein the cable port is positioned on the distal end of the housing.

Example 6

The ultrasonic surgical instrument of Example 5, further comprising a sterile adapter assembly secured to the distal end of the housing, wherein the sterile adapter assembly includes a cable adapter connected to the electrical cable.

Example 7

The ultrasonic surgical instrument of any one of the preceding Examples, wherein the electrical cable includes a self-managing portion that is selected from the group consisting of: a helical cable and a ribbon cable.

Example 8

The ultrasonic surgical instrument of any one of the preceding Examples, further comprising a cable guide positioned in the housing and extending between the cable port and the ultrasonic transducer assembly, wherein the cable guide defines a predetermined path and receives the electrical cable along the predetermined path such that the cable guide is configured to retain the electrical cable along the predetermined path as the ultrasonic transducer assembly selectively moves from the proximal, retracted position to the distal, extended position.

Example 9

The ultrasonic surgical instrument of Example 8, wherein the cable guide includes a plurality of links pivotally connected in succession to define the predetermined path.

Example 10

The ultrasonic surgical instrument of any one of the preceding examples, wherein the end effector further includes a clamp arm pivotally connected relative to the ultrasonic blade and configured to selectively move from an open position for receiving a tissue and a closed position for clamping tissue against the ultrasonic blade.

Example 11

The ultrasonic surgical instrument of Example 10, further comprising a flex circuit operatively connected to the ultrasonic transducer assembly and having a closure switch and a manual activation switch, wherein the closure switch is configured to activate the ultrasonic transducer assembly with the clamp arm in the closed position with a predetermined clamping force, and wherein the manual activation switch is configured to allow manual activation of the ultrasonic transducer assembly.

Example 12

The ultrasonic surgical instrument of Example 11, wherein the flex circuit is mounted to the carrier.

Example 13

The ultrasonic surgical instrument of Example 11, wherein the flex circuit is mounted to a proximal end of the housing.

Example 14

The ultrasonic surgical instrument of Example 13, wherein the proximal end of the housing includes a manual activation switch configured to be accessed and manipulated by an operator to activate the ultrasonic transducer assembly.

Example 15

The ultrasonic surgical instrument of any one of the preceding examples, wherein the electrical cable includes a plurality of electrical conductors electrically connected in succession.

Example 16

A robotic surgical system, comprising: a patient support; (b) at least one robotic arm movable relative to the patient support; and (c) an ultrasonic surgical instrument, including: (i) an end effector including an ultrasonic blade, (ii) a shaft assembly defining a longitudinal axis and proximally extending from the end effector, wherein the shaft assembly includes an acoustic waveguide in acoustic communication with the ultrasonic blade, (iii) an ultrasonic transducer assembly proximally extending from and in acoustic communication with the acoustic waveguide, (iv) a housing proximally projecting from the shaft assembly such that the ultrasonic transducer assembly is positioned within the housing, (v) a carrier movably supporting the ultrasonic transducer assembly along the longitudinal axis such that the ultrasonic transducer assembly, the acoustic waveguide, and the end effector are configured to collectively move relative to the housing from a proximal, retracted position on the longitudinal axis to a distal, extended position on the longitudinal axis for inserting the ultrasonic blade into a patient, and (vi) an electrical cable extending through the housing at a cable port and electrically connected to the ultrasonic transducer assembly, wherein the electrical cable is configured to transmit electrical communication therealong for operating the ultrasonic transducer assembly.

Example 17

A method of managing an electrical cable in an ultrasonic surgical instrument, wherein the ultrasonic surgical instrument includes: an end effector including an ultrasonic blade, a shaft assembly defining a longitudinal axis and proximally extending from the end effector, wherein the shaft assembly includes an acoustic waveguide in acoustic communication with an acoustic blade, an ultrasonic transducer assembly proximally extending from and in acoustic communication with the acoustic waveguide, a housing proximally projecting from the shaft assembly such that the ultrasonic transducer assembly is positioned within the housing, a carrier movably supporting the ultrasonic transducer assembly along the longitudinal axis, and the electrical cable extending through the housing at a cable port and electrically connected to the ultrasonic transducer assembly, the method comprising: (a) moving the carrier through the housing; and (b) guiding movement of the electrical cable as at least a portion of the electrical cable remains connected with the carrier to thereby manage the electrical cable.

Example 18

The method of Example 17, further comprising urging at least a portion of the electrical cable along a path.

Example 19

The method of Example 18, further comprising urging a first portion of an electrical cable along a path with a second portion of the electrical cable such that the electrical cable is self-managed.

Example 20

The method of Example 18, further comprising urging at least a portion of the electrical cable along a path with a cable guide such that the electrical cable is actively managed with the cable guide.

V. MISCELLANEOUS

Any one or more of the teaching, expressions, embodiments, examples, etc. described herein may be combined with any one or more of the teachings, expressions, embodiments, examples, etc. described in U.S. patent application Ser. No. 17/077,067, entitled "Surgical Instrument and Carrier KART Supporting Ultrasonic Transducer," filed on Oct. 22, 2020, published as U.S. Pub. No. 2022/0125465 on Apr. 28, 2022; U.S. patent application Ser. No. 17/077,086, entitled "Carrier KART and Jaw Closure of an Ultrasonic Surgical Instrument," filed on Oct. 22, 2020, published as U.S. Pub. No. 2022/0125466 on Apr. 28, 2022; U.S. patent application Ser. No. 17/077,130, entitled "Surgical Instrument with Clamping Sensor Feedback and Related Methods," filed on Oct. 22, 2020, published as U.S. Pub. No. 2022/0125469 on Apr. 28, 2022; U.S. patent application Ser. No. 17/077,136, entitled "Surgical Instrument with Non-clamping Sensor Feedback and Related Methods," filed on Oct. 22, 2020, published as U.S. Pub. No. 2022/0125470 on Apr. 28, 2022; U.S. patent application Ser. No. 17/077, 250, entitled "Ultrasonic Surgical Instrument with a Carrier KART and Reusable Stage," filed on Oct. 22, 2020, published as U.S. Pub. No. 2022/0125472 on Apr. 28, 2022; U.S. patent application Ser. No. 17/077,139, entitled "Ultrasonic Surgical Instrument with a Fixed Transducer Grounding," filed on Oct. 22, 2020, published as U.S. Pub. No. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pub. No. 2022/0125460 on Apr. 28, 2022; U.S. patent application Ser. No. 17/077,152, entitled "Damping Rings for an Ultrasonic Surgical Instrument," filed on Oct. 22, 2020, issued as U.S. Pat. No. 11,806,037 on Nov. 7, 2023; U.S. patent application Ser. No. 17/077,110, entitled "Ultrasonic Surgical Instrument with a Mid-shaft Closure System and Related Methods," filed on Oct. 22, 2020, published as U.S. Pub. No. 2022/0125468 on Apr. 28, 2022; U.S. patent application Ser. No. 17/076,956, entitled "Surgical Instrument with an Articulatable Shaft Assembly and Dual End Effector Roll," filed on Oct. 22, 2020, issued as U.S. Pat. No. 11,890,030 on Feb. 6, 2024; U.S. patent application Ser. No. 17/076,959, entitled "Ultrasonic Surgical Instrument with a Distally Grounded Acoustic Waveguide," filed on Oct. 22, 2020, published as U.S. Pub. No. 2022/0125464 on Apr. 28, 2022; and/or U.S. patent application Ser. No. 17/077,098, entitled "Ultrasonic Surgical Instrument with a Multiplanar Articulation Joint," filed on Oct. 22, 2020, published as U.S. Pub. No. 2022/0125467 on Apr. 28, 2022. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) an end effector including an ultrasonic blade;
   (b) a shaft assembly defining a longitudinal axis and proximally extending from the end effector, wherein the shaft assembly includes an acoustic waveguide in acoustic communication with the ultrasonic blade;
   (c) an ultrasonic transducer assembly proximally extending from and in acoustic communication with the acoustic waveguide;
   (d) a housing proximally projecting from the shaft assembly such that the ultrasonic transducer assembly is positioned within the housing, wherein the housing includes a distal end, a proximal end, and a sidewall extending therebetween;
   (e) a carrier movably supporting the ultrasonic transducer assembly along the longitudinal axis such that the ultrasonic transducer assembly, the acoustic waveguide, and the end effector are configured to collectively move relative to the housing from a proximal, retracted position on the longitudinal axis to a distal, extended position on the longitudinal axis for inserting the ultrasonic blade into a patient;
   (f) an electrical cable extending through the housing at a cable port and electrically connected to the ultrasonic transducer assembly, wherein the electrical cable is configured to transmit electrical communication therealong for operating the ultrasonic transducer assembly, and wherein the cable port is positioned on the distal end of the housing; and
   (g) a sterile adapter assembly secured to the housing, wherein the sterile adapter assembly includes a cable adapter connected to the electrical cable, wherein the sterile adapter assembly is secured to the distal end of the housing.

2. The ultrasonic surgical instrument of claim 1, wherein the electrical cable includes a self-managing portion that is selected from the group consisting of: a helical cable and a ribbon cable.

3. The ultrasonic surgical instrument of claim 1, further comprising a cable guide positioned in the housing and extending between the cable port and the ultrasonic transducer assembly, wherein the cable guide defines a predetermined path and receives the electrical cable along the predetermined path such that the cable guide is configured to retain the electrical cable along the predetermined path as the ultrasonic transducer assembly selectively moves from the proximal, retracted position to the distal, extended position.

4. The ultrasonic surgical instrument of claim 3, wherein the cable guide includes a plurality of links pivotally connected in succession to define the predetermined path.

5. The ultrasonic surgical instrument of claim 1, wherein the end effector further includes a clamp arm pivotally connected relative to the ultrasonic blade and configured to selectively move from an open position for receiving a tissue and a closed position for clamping tissue against the ultrasonic blade.

6. The ultrasonic surgical instrument of claim 5, further comprising a flex circuit operatively connected to the ultrasonic transducer assembly and having a closure switch and a manual activation switch, wherein the closure switch is configured to activate the ultrasonic transducer assembly with the clamp arm in the closed position with a predetermined clamping force, and wherein the manual activation switch is configured to allow manual activation of the ultrasonic transducer assembly.

7. The ultrasonic surgical instrument of claim 6, wherein the flex circuit is mounted to the carrier.

8. The ultrasonic surgical instrument of claim 6, wherein the flex circuit is mounted to the proximal end of the housing.

9. The ultrasonic surgical instrument of claim 8, wherein the proximal end of the housing includes the manual activation switch configured to be accessed and manipulated by an operator to activate the ultrasonic transducer assembly.

10. The ultrasonic surgical instrument of claim 1, wherein the electrical cable includes a plurality of electrical conductors electrically connected in succession.

11. An ultrasonic surgical instrument, comprising:
(a) an end effector including an ultrasonic blade;
(b) a shaft assembly defining a longitudinal axis and proximally extending from the end effector, wherein the shaft assembly includes an acoustic waveguide in acoustic communication with the ultrasonic blade;
(c) an ultrasonic transducer assembly proximally extending from and in acoustic communication with the acoustic waveguide;
(d) a housing proximally projecting from the shaft assembly such that the ultrasonic transducer assembly is positioned within the housing;
(e) a carrier movably supporting the ultrasonic transducer assembly along the longitudinal axis such that the ultrasonic transducer assembly, the acoustic waveguide, and the end effector are configured to collectively move relative to the housing from a proximal, retracted position on the longitudinal axis to a distal, extended position on the longitudinal axis for inserting the ultrasonic blade into a patient;
(f) an electrical cable extending through the housing at a cable port and electrically connected to the ultrasonic transducer assembly, wherein the electrical cable is configured to transmit electrical communication therealong for operating the ultrasonic transducer assembly; and
(g) a cable guide positioned in the housing and extending between the cable port and the ultrasonic transducer assembly, wherein the cable guide defines a predetermined path and receives the electrical cable along the predetermined path such that the cable guide is configured to retain the electrical cable along the predetermined path as the ultrasonic transducer assembly selectively moves from the proximal, retracted position to the distal, extended position,
wherein the cable guide includes a plurality of links pivotally connected in succession to define the predetermined path.

12. The ultrasonic surgical instrument of claim 11, further comprising a sterile adapter assembly secured to the housing, wherein the sterile adapter assembly includes a cable adapter connected to the electrical cable.

13. An ultrasonic surgical instrument, comprising:
(a) an end effector including an ultrasonic blade and a clamp arm pivotally connected relative to the ultrasonic blade, wherein the clamp arm is configured to selectively move from an open position for receiving a tissue and a closed position for clamping tissue against the ultrasonic blade;
(b) a shaft assembly defining a longitudinal axis and proximally extending from the end effector, wherein the shaft assembly includes an acoustic waveguide in acoustic communication with the ultrasonic blade;
(c) an ultrasonic transducer assembly proximally extending from and in acoustic communication with the acoustic waveguide;
(d) a housing proximally projecting from the shaft assembly such that the ultrasonic transducer assembly is positioned within the housing;
(e) a carrier movably supporting the ultrasonic transducer assembly along the longitudinal axis such that the ultrasonic transducer assembly, the acoustic waveguide, and the end effector are configured to collectively move relative to the housing from a proximal, retracted position on the longitudinal axis to a distal, extended position on the longitudinal axis for inserting the ultrasonic blade into a patient;
(f) an electrical cable extending through the housing at a cable port and electrically connected to the ultrasonic transducer assembly, wherein the electrical cable is configured to transmit electrical communication therealong for operating the ultrasonic transducer assembly; and
(g) a flex circuit operatively connected to the ultrasonic transducer assembly,
wherein the flex circuit has a manual activation switch, and wherein the manual activation switch is configured to allow manual activation of the ultrasonic transducer assembly, and
wherein the flex circuit has a closure switch configured to activate the ultrasonic transducer assembly with the clamp arm in the closed position with a predetermined clamping force.

14. The ultrasonic surgical instrument of claim 13, further comprising a sterile adapter assembly secured to the housing, wherein the sterile adapter assembly includes a cable adapter connected to the electrical cable.

15. The ultrasonic surgical instrument of claim 13, wherein the flex circuit is mounted to the carrier.

16. The ultrasonic surgical instrument of claim 13, wherein the flex circuit is mounted to a proximal end of the housing.

17. The ultrasonic surgical instrument of claim 16, wherein the proximal end of the housing includes the manual activation switch configured to be accessed and manipulated by an operator to activate the ultrasonic transducer assembly.

* * * * *